(12) United States Patent
Anderson et al.

(10) Patent No.: US 8,511,304 B2
(45) Date of Patent: Aug. 20, 2013

(54) MEDICAMENT DISPENSER

(75) Inventors: Gregor John McLennan Anderson, Ware (GB); Stanley George Bonney, Ware (GB); Michael Birsha Davies, Ware (GB); Daniel Thomas De Sansmarez Lintell, Ware (GB); Alan Anthony Wilson, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1024 days.

(21) Appl. No.: 10/502,519

(22) PCT Filed: Jan. 22, 2003

(86) PCT No.: PCT/EP03/00598
§ 371 (c)(1),
(2), (4) Date: Jan. 14, 2005

(87) PCT Pub. No.: WO03/061743
PCT Pub. Date: Jul. 31, 2003

(65) Prior Publication Data
US 2005/0154491 A1   Jul. 14, 2005

(30) Foreign Application Priority Data
Jan. 25, 2002  (GB) .................................. 0201677.2

(51) Int. Cl.
*A61M 16/00* (2006.01)
*F16K 11/00* (2006.01)
*G05D 1/02* (2006.01)

(52) U.S. Cl.
USPC ............ 128/203.25; 128/203.15; 128/203.21; 128/200.14; 128/200.12; 221/25; 221/225; 221/71; 221/27; 221/72; 221/70

(58) Field of Classification Search
USPC ...... 221/25, 225, 71, 27, 72, 70; 128/203.15, 128/203.21, 200.14
See application file for complete search history.

(56) References Cited

U.S. PATENT DOCUMENTS
3,269,389 A   8/1966 Meurer et al.
3,704,725 A   12/1972 Marand
(Continued)

FOREIGN PATENT DOCUMENTS
DE   1461280   2/1969
DE   4305277   8/1995
(Continued)

OTHER PUBLICATIONS

EP Search Report issued Nov. 18, 2010 for EP Application No. 10178947.7.
Office Action dated Apr. 30, 2009 for U.S. Appl. No. 10/523,121.
European Search Report dated Nov. 18, 2010 for EP Application No. 10178947.7.
Claims Set as of Jun. 29, 2011 for EP Application No. 10178947.7.
Examination Report dated Aug. 25, 2011 for EP Application No. 10178947.7.

(Continued)

*Primary Examiner* — Gene O. Crawford
*Assistant Examiner* — Rakesh Kumar
(74) *Attorney, Agent, or Firm* — James P. Riek

(57) ABSTRACT

There is provided a medicament dispenser for use with plural elongate form medicament carriers, each having multiple distinct medicament dose portions carried thereby, the dispenser having a dispensing mechanism for dispensing the distinct medicament dose portions carried by each of the plural medicament carriers. The mechanism comprises a receiving station for receiving each of the plural medicament carriers; a release for releasing a distinct medicament dose portion from each of the plural medicament carriers on receipt thereof by the receiving station; an outlet, positioned to be in communication with the distinct medicament dose portions releasable by said a release; and an indexer for individually indexing the distinct medicament dose portions of each of the plural medicament carriers.

74 Claims, 27 Drawing Sheets

(56) References Cited

U.S. PATENT DOCUMENTS

| | | |
|---|---|---|
| 3,908,866 A | 9/1975 | Brown |
| 4,330,835 A | 5/1982 | Gehm |
| 4,627,432 A | 12/1986 | Newell et al. |
| 4,778,054 A | 10/1988 | Newell et al. |
| 4,811,731 A | 3/1989 | Rand et al. |
| 4,823,982 A * | 4/1989 | Aten et al. ............... 221/3 |
| 4,940,966 A | 7/1990 | Pettigrew et al. |
| 5,002,048 A * | 3/1991 | Makiej, Jr. ............ 128/200.23 |
| 5,007,419 A | 4/1991 | Weinstein et al. |
| 5,169,029 A | 12/1992 | Behar et al. |
| 5,427,267 A * | 6/1995 | Willman ............ 229/117.34 |
| 5,437,267 A * | 8/1995 | Weinstein et al. ...... 128/200.23 |
| 5,437,270 A | 8/1995 | Braithwaite |
| 5,462,205 A | 10/1995 | Keller |
| 5,497,765 A | 3/1996 | Praud et al. |
| 5,505,704 A | 4/1996 | Pawelka et al. |
| 5,524,613 A | 6/1996 | Haber et al. |
| 5,552,438 A | 9/1996 | Christensen, IV |
| 5,582,162 A * | 12/1996 | Petersson ............ 128/203.15 |
| 5,590,645 A | 1/1997 | Davies et al. |
| 5,664,557 A * | 9/1997 | Makiej, Jr. ............ 128/200.23 |
| 5,743,252 A | 4/1998 | Rubsamen et al. |
| 5,772,085 A | 6/1998 | Bryant et al. |
| 5,778,873 A | 7/1998 | Braithwaite |
| 5,830,490 A | 11/1998 | Weinstein et al. |
| 5,860,419 A | 1/1999 | Davies et al. |
| 5,873,360 A * | 2/1999 | Davies et al. ............ 128/203.15 |
| 5,901,883 A | 5/1999 | Ritsche |
| 5,941,241 A | 8/1999 | Weinstein et al. |
| 5,998,428 A | 12/1999 | Barnette et al. |
| 6,029,663 A | 2/2000 | Eisele et al. |
| 6,116,237 A | 9/2000 | Schultz et al. |
| 6,125,844 A | 10/2000 | Samiotes |
| 6,234,167 B1 | 5/2001 | Cox et al. |
| 6,382,205 B1 | 5/2002 | Weinstein et al. |
| 6,502,783 B1 * | 1/2003 | Smith et al. ............ 242/530.3 |
| 6,523,536 B2 | 2/2003 | Fugelsang et al. |
| 6,543,443 B1 | 4/2003 | Klimowicz et al. |
| 6,559,168 B2 | 5/2003 | Marfat et al. |
| 6,571,790 B1 | 6/2003 | Weinstein |
| 6,640,804 B2 | 11/2003 | Ivri et al. |
| 6,684,880 B2 | 2/2004 | Trueba |
| 6,698,422 B2 | 3/2004 | Fugelsang et al. |
| 6,698,425 B1 * | 3/2004 | Widerstrom ............ 128/203.25 |
| 6,810,873 B1 | 11/2004 | Haikarainen et al. |
| 6,810,874 B1 | 11/2004 | Koskela et al. |
| 6,845,772 B2 | 1/2005 | Braithwaite et al. |
| 6,880,722 B2 * | 4/2005 | Anderson et al. ............ 221/71 |
| 6,889,690 B2 | 5/2005 | Crowder et al. |
| 6,971,383 B2 | 12/2005 | Hickey et al. |
| 7,219,665 B1 * | 5/2007 | Braithwaite ............ 128/203.21 |
| 7,234,464 B2 | 6/2007 | Goede et al. |
| 2001/0020147 A1 | 9/2001 | Staniforth et al. |
| 2001/0027789 A1 | 10/2001 | Goede et al. |
| 2002/0128612 A1 | 9/2002 | Andersson et al. |
| 2002/0189612 A1 | 12/2002 | Rand |
| 2003/0018019 A1 | 1/2003 | Meade et al. |
| 2003/0075172 A1 | 4/2003 | Johnson et al. |
| 2004/0025877 A1 | 2/2004 | Crowder et al. |
| 2004/0050864 A1 | 3/2004 | Stradella |
| 2004/0099676 A1 | 5/2004 | Anderson et al. |
| 2005/0154491 A1 | 7/2005 | Anderson et al. |
| 2005/0247312 A1 | 11/2005 | Davies |
| 2005/0251289 A1 | 11/2005 | Bonney et al. |
| 2005/0268908 A1 | 12/2005 | Bonney et al. |
| 2005/0268909 A1 | 12/2005 | Bonney et al. |
| 2005/0274378 A1 | 12/2005 | Bonney et al. |
| 2007/0044795 A1 * | 3/2007 | Casper et al. ............ 128/203.15 |
| 2007/0062425 A1 * | 3/2007 | Auer et al. ............ 111/57 |
| 2007/0062525 A1 | 3/2007 | Bonney et al. |
| 2007/0181124 A1 | 8/2007 | Casper et al. |
| 2008/0308102 A1 * | 12/2008 | Davies et al. ............ 128/203.15 |
| 2009/0308102 A1 * | 12/2009 | Miller ............ 63/15 |

FOREIGN PATENT DOCUMENTS

| | | |
|---|---|---|
| DE | 3348370 C2 | 10/2001 |
| EP | 0321434 A2 | 6/1989 |
| EP | 0372777 B1 | 6/1990 |
| EP | 0469814 | 2/1992 |
| EP | 469814 A1 * | 2/1992 |
| EP | 521434 | 1/1993 |
| EP | 751077 | 1/1997 |
| EP | 1300171 | 4/2003 |
| EP | 2266650 A1 | 12/2010 |
| GB | 1387954 | 3/1975 |
| GB | 2242134 | 9/1991 |
| GB | 2327408 | 1/1999 |
| IN | 200300224 | 2/2005 |
| JP | 4220266 A | 11/1992 |
| JP | 2001161788 A | 6/2001 |
| WO | WO 92/12402 | 7/1992 |
| WO | WO 96/31790 | 10/1996 |
| WO | WO 98/30332 | 7/1998 |
| WO | WO 98/34664 | 8/1998 |
| WO | WO 98/51257 | 11/1998 |
| WO | 9942154 A1 | 8/1999 |
| WO | WO 99/39991 | 8/1999 |
| WO | 9947505 A1 | 9/1999 |
| WO | WO 00/00411 | 1/2000 |
| WO | WO 00/45879 | 8/2000 |
| WO | 0051599 A1 | 9/2000 |
| WO | WO 00/64519 | 11/2000 |
| WO | WO 00/64520 | 11/2000 |
| WO | 0117595 A1 | 3/2001 |
| WO | WO 01/24690 | 4/2001 |
| WO | WO 01/26020 | 4/2001 |
| WO | WO 01/26021 | 4/2001 |
| WO | 0131578 A1 | 5/2001 |
| WO | 0143801 A2 | 6/2001 |
| WO | WO 01/39823 | 6/2001 |
| WO | WO 01/41849 | 6/2001 |
| WO | 0168169 A1 | 9/2001 |
| WO | WO 01/98176 | 12/2001 |
| WO | 0205878 A1 | 1/2002 |
| WO | 0205879 A1 | 1/2002 |
| WO | WO 02/04055 | 1/2002 |
| WO | 0236190 A2 | 5/2002 |
| WO | WO 02/053294 | 7/2002 |
| WO | 03035137 A2 | 5/2003 |
| WO | 03043684 A1 | 5/2003 |
| WO | 03061743 A1 | 7/2003 |
| WO | 03061744 A1 | 7/2003 |
| WO | 03095010 A2 | 11/2003 |
| WO | 2004011070 A1 | 2/2004 |

OTHER PUBLICATIONS

File History for U.S. Appl. No. 10/502,405, filed Feb. 7, 2005.
Office Action dated Aug. 5, 2008 for U.S. Appl. No. 10/502,405.
File History for U.S. Appl. No. 10/522,319, filed Jan. 25, 2005.
Office Action dated Aug. 5, 2008 for U.S. Appl. No. 10/522,319.
File History for U.S. Appl. No. 10/522,324, filed Jan. 25, 2005.
Office Action dated Aug. 5, 2008 for U.S. Appl. No. 10/522,324.
File History for U.S. Appl. No. 10/523,121, filed Jan. 24, 2005.
Office Action dated Apr. 3, 2007 for U.S. Appl. No. 10/523,121.
Amendment filed Oct. 2, 2007 in response to Office Action dated Apr. 3, 2007 for U.S. Appl. No. 10/523,121.
Office Action dated Dec. 21, 2007 for U.S. Appl. No. 10/523,121.
Amendment filed Apr. 21, 2008 in response to Office Action dated Dec. 21, 2007 for U.S. Appl. No. 10/523,121.
Office Action dated Jul. 7, 2008 for U.S. Appl. No. 10/523,121.
Amendment filed Dec. 8, 2008 in response to Office Action dated Jul. 7, 2008 for U.S. Appl. No. 10/523,121.
Notice of Non-Compliant Amendment dated Dec. 18, 2008 for U.S. Appl. No. 10/523,121.
Compliant Amendment filed Jan. 14, 2009 in response to Office Action dated Jul. 7, 2008 for U.S. Appl. No. 10/523,121.

* cited by examiner

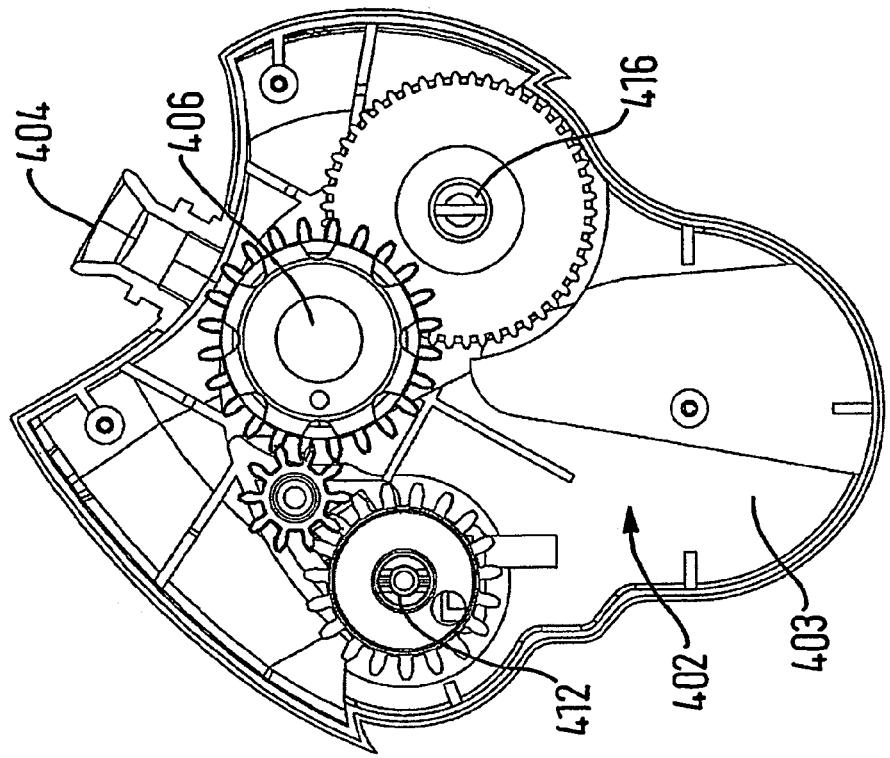
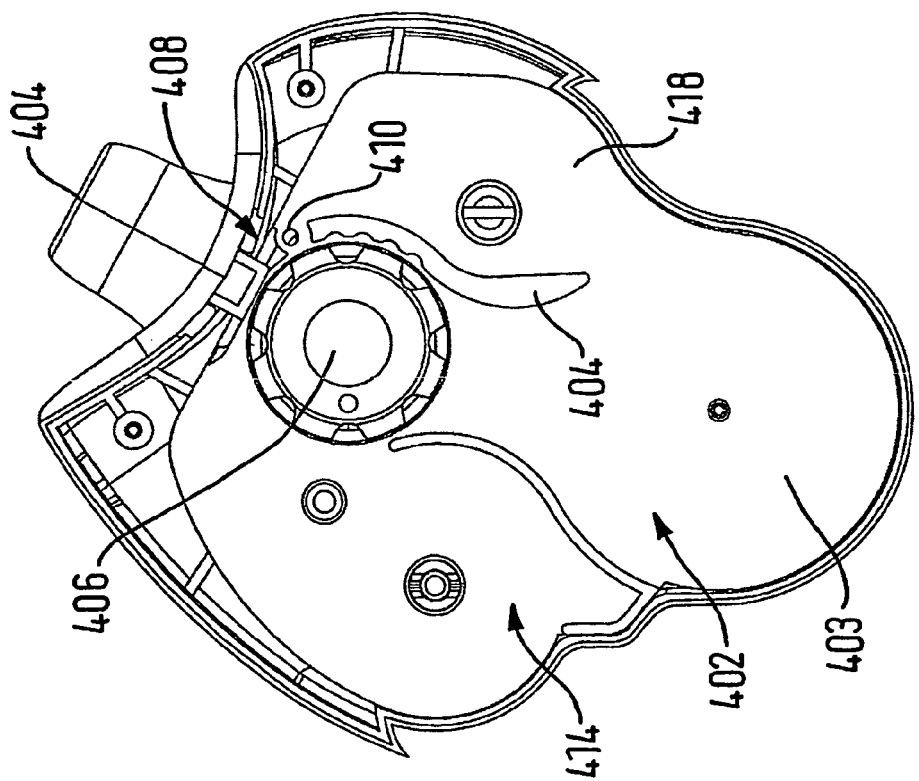
FIG. 4e
FIG. 4d

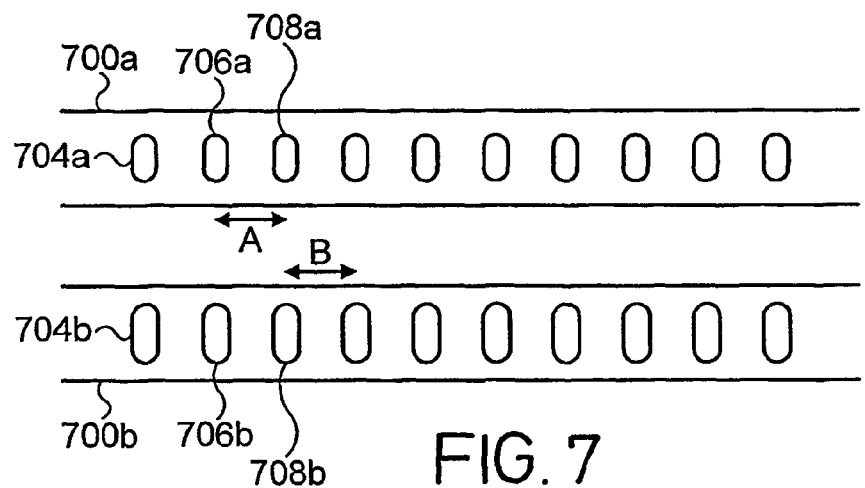
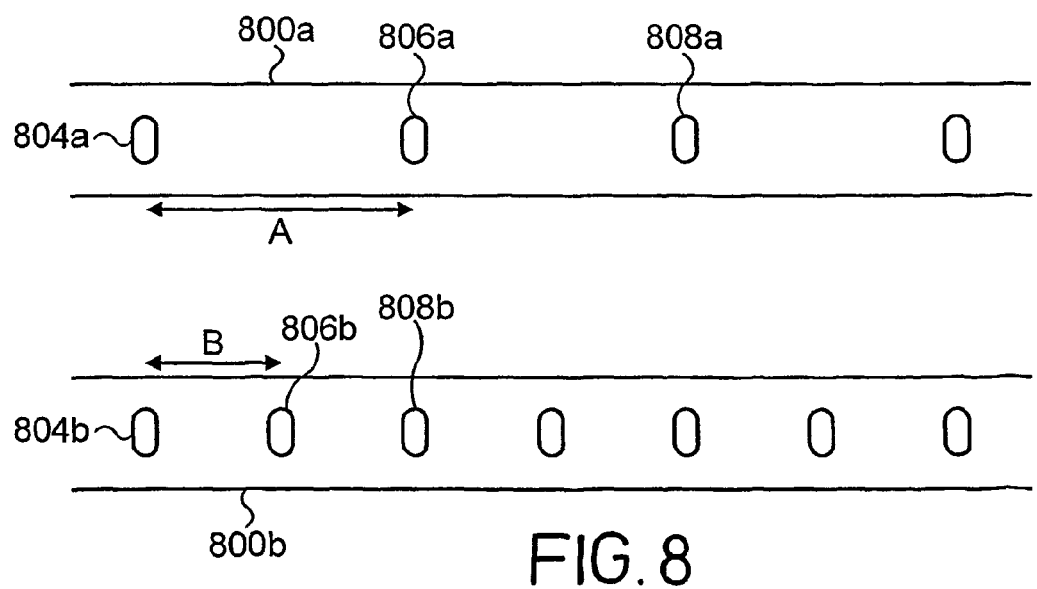

MEDICAMENT DISPENSER

This application is filed pursuant to 35 USC 371 as a United States National Phase Application of International Patent Application Serial No. PCT/EP03/00598 filed on Jan. 22, 2003, which claims priority from GB 021677.2 filed on Jan. 25, 2002 in the United Kingdom.

TECHNICAL FIELD

The present invention relates to a medicament dispenser for dispensing medicament. The invention particularly relates to a dispenser for use in dispensing medicament in powder or tablet form.

BACKGROUND TO THE INVENTION

The use of inhalation devices in the administration of medicaments, for example in bronchodilation therapy is well known. Such devices generally comprise a body or housing within which a medicament carrier is located. Known inhalation devices include those in which the medicament carrier is a blister strip containing a number of discrete doses of powdered medicament. Such devices usually contain a mechanism of accessing these doses, usually comprising either piercing means or means to peel a lid sheet away from a base sheet. The powdered medicament can then be accessed and inhaled. Such a mechanism may also be used for dispensing medicament in tablet form wherein peeling away the lid sheet from the base sheet reveals a tablet for removal and subsequent consumption.

Therapies involving combinations of different and complementary active medicaments are known. These can be administered either as distinct combination (i.e. multi-active) medicament products, which comprise a defined mixture of each component medicament, or as groups of single active medicament products, which are designed to be taken in combination or sequentially. Whilst combination products offer added convenience for the patient, certain medicament actives are difficult to formulate as distinct combination products. For example, the actives may interact chemically with each other in an undesirable way when formulated together.

It is thus, desirable in certain circumstances, to have a medicament dispenser that separately (i.e. in isolated fashion) contains each active component (or mixture thereof) of a combination product, but which enables the delivery of a combined dose in response to a minimum number of patent actions. In particular, it is desirable that all active components of the combined dose are delivered to the patient in a single, combined dose in response to a single patient dosing action. For example, it is desirable that a combination inhaled medicament product be delivered in response to a single actuation of an inhaler, even where the active components of that combined product are separately stored within the inhaler device.

The Applicants have now found that a particularly effective way to meet the above described desiderata is provided by a medicament dispenser which comprises plural, separate elongate form medicament carriers (e.g. blister strips), each containing in isolated fashion, a different medicament active (or mixture thereof), wherein the dispenser enables release of the medicament actives from each separate blister strip to provide a combined dose for administration to a patient.

SUMMARY OF THE INVENTION

According to one aspect of the invention there is provided a medicament dispenser for containing plural elongate form medicament carriers, each having multiple distinct medicament dose portions carried thereby, said dispenser having a dispensing mechanism for dispensing the distinct medicament dose portions carried by each of said plural medicament carriers, said mechanism comprising, a) at least one receiving station for receiving each of the plural medicament carriers;
b) a release for releasing in combination a distinct medicament dose portion from each of the plural medicament carriers on receipt thereof by said receiving station;
c) an outlet, positioned to be in communication with the distinct medicament dose portions releasable by said release; and
d) at least one indexer for individually indexing the distinct medicament dose portions of each of the plural medicament carriers.

In combination, the distinct medicament dose portions releasable from each of the plural medicament carriers comprise a defined dose of combination product. That is to say, that when combined together (e.g. on release) the distinct active medicament dose portions form a single dose of a 'multi-active' medicament treatment The medicament dispenser is designed to receive plural elongate form medicament carriers. Preferably, the medicament dispenser is designed to receive from two to four such elongate form medicament carriers, more preferably two such carriers.

Each medicament carrier has multiple distinct dose portions carried thereby. The distinct dose portions are typically arranged in spaced fashion, more preferably In progressive arrangement (e g. series progression) on the carrier such that each dose portion is separately accessible.

The term medicament carrier herein is used to define any suitable form of carrier. Suitably, each elongate form medicament carrier is in the form of a strip or tape. In one preferred aspect, the earner has a blister pack form, but it could also, for example, comprise a carrier onto which medicament has been applied by any suitable process including printing, painting and vacuum occlusion.

In one aspect, the medicament carrier comprises a blister pack in laminate form. Suitably, the laminate comprises material selected from the group consisting of metal foil, organic polymeric material and paper. Suitable metal foils include aluminium or tin foil having a thickness of from 5 to 100 μm, preferably from 10 to 50 μm, such as 20 to 30 μm. Suitable organic polymeric materials include polyethylene, polypropylene, polyvinyl chloride and polyethylene terephthalate.

Access to the medicament dose portions comprised within the pockets of the elongate strip form carrier is by any suitable access means including tearing, piercing or peeling apart the relevant pockets.

One suitable blister pack form medicament carrier comprises a peelable blister strip. Suitably, the peelable blister strip comprises a base sheet in which blisters are formed to define pockets therein for containing distinct medicament dose portions and a lid sheet which is hermetically sealed to the base sheet except in the region of the blisters in such a manner that the lid sheet and the base sheet can be peeled apart. The base and lid sheets are typically sealed to one another over their whole width except for the forward end portions where they are typically not sealed to one another at all. Thus, separate base and lid sheet forward end portions are presented at the end of the strip. The respective base and lid sheets are peelably separable from each other to (e.g. separately) release the contents of each pocket.

Suitably, the lid sheet comprises at least the following successive layers: (a) paper; adhesively bonded to (b) polyester; adhesively bonded to (c) aluminium foil; that is coated with a heat seal lacquer for bonding to the base sheet. The thickness of each layer may be selected according to the desired properties but is typically of the order of from 5 to 200 micron, particularly from 10 to 50 micron.

Suitably, the base sheet comprises at least the following successive layers: (a) oriented polyamide (OPA); adhesively bonded to (b) aluminium foil; adhesively bonded to (c) a third layer comprising a polymeric material (e.g. polyvinyl chloride).

Various known techniques can be employed to join the lid and base sheet and hence to seal the blisters of the peelable blister strip. Such methods include adhesive bonding, hot metal bonding, hot metal welding, radio frequency welding, laser welding, ultrasonic welding and hot bar sealing. The lid sheet and base sheet of the peelable blister strip are particularly sealable by 'cold form' sealing methods, which are conducted at lower temperatures than conventional heat sealing methods. Such 'cold form' sealing methods are of particular utility where the medicament or medicament formulation for containment within the blister is heat sensitive (e.g. degrades or denatures on heating). Suitable 'cold form' sealing methods are conducted at a temperature in the range of 150-250° C., more preferably, 210-240° C.

Each medicament carrier has multiple distinct (i.e. separate) medicament dose portions carried thereby. The term 'dose portion' is employed because in the context of the invention the distinct 'portions' are brought together to form a combination (i.e. multi-active) product dose.

In one aspect, each 'dose portion' comprises a single active (i.e. mono-active) medicament component. Each mono-active component is therefore brought together only at the time of release to form the overall combination product.

In another aspect, one or more of the 'dose portions' comprise plural active medicament components (e.g. as a formulated mixture thereof). Typically, these plural components will be 'co-formulation compatible' wherein that term is used to mean compatible in the sense of being amenable to co-formulation, perhaps even displaying synergetic co-formulation characteristics.

In one particular aspect, a first elongate form medicament carrier has multiple distinct mono-active medicament dose portions carried thereby and a second elongate form medicament carrier has multiple distinct plural-active (particularly, bi-active dose portions i.e. comprising two active components) medicament dose portions carried thereby. In combination, the mono-active and plural-active medicament components comprise a defined combination product. That is to say, that when combined together the distinct mono- and bi-active medicament dose portions released by actuation of the dispenser form a dose of a 'multi-active' medicament treatment.

In one aspect, each of the elongate form medicament carriers is sized and shaped to carry equivalent dose portions, that is to say each carrier is suitable for carrying dose portions of equivalent dose volume or dose weight. In one particular example, each medicament carrier of a bi-carrier dispenser is arranged to carry plural 12 mg (or 25 mg) dose portions.

In another aspect, each of the elongate form medicament carriers is sized and shaped to carry non-equivalent dose portions, that is to say each carrier is arranged to carry dose portions of non-equivalent dose volume or dose weight to the other. In one specific example, a first medicament carrier of a bi-carrier dispenser is arranged to carry plural 12 mg dose portions and the second carrier thereof is arranged to carry 25 mg dose portions.

In one aspect, the multiple distinct dose portions are provided to each carrier in uniform series. In particular, the spacing (i.e. pitch) between each dose portion is uniform throughout the series. In other aspects however, the spacing (i.e. pitch) may vary throughout the series (i.e. be non-uniform). In specific examples, the pitch may progressively decrease or progressively increase throughout the series. Such variation may in aspects, be required to compensate for non-uniform indexing by the carrier indexing and/or advancement mechanism of a particular dispenser.

In one aspect, the spacing (i.e. pitch) between each dose portion is equivalent for each carrier of the dispenser. That is to say, each medicament carrier is equivalently pitched. In other aspects, the spacing between each dose portion is non-equivalent for each carrier of the dispenser. Such variation of the spacing (i.e. pitch) from carrier to carrier can be used to enable flexibility in (combination) dosage patterns.

In one particular example, the spacing (i.e. pitch) of a first carrier is arranged to be half that of a second carrier. This arrangement is beneficially employed where the dose interval (i.e. time between doses) of the medicament carried by the first carrier is twice that of the medicament carrier by the second carrier (e.g. in a twice daily/once daily type dosage regime).

The plural elongate form medicament carriers may be provided to the dispenser in any suitable configuration. One preferred configuration is the 'side-by-side' configuration, in which for example, two carriers (e.g. two coiled blister strips) are arranged to lie in sideways alignment with each other in the dispenser. Another preferred configuration is the 'double-decker' configuration, in which for example, two carriers (e.g. two coiled blister strips sharing the same coiling axis) are arranged to lie one on top of each other in the dispenser.

The plural carriers are typically provided to the dispenser as separate entities. Alternative embodiments are however, envisaged in which the separate plural elongate carriers are joined together in some appropriate fashion. Thus, for example in a variation of an embodiment comprising two separate elongate strip form carriers each carrying multiple distinct medicament dose portions arranged in series along the respective strip and mountable in the dispenser in 'double-decker' configuration there might be provided a single strip comprising two separate series of multiple distinct medicament dose portions arranged in 'double decker' configuration (i.e. parallel to each other) as if the two strips of the first embodiment had simply been joined together along adjoining elongate sides thereof.

In a particular 'joined together' configuration, two elongate strip form carriers are arranged in 'back-to-back' configuration (i.e. one strip backs onto the other with the pockets of each facing outwards). In this embodiment, the 'back-to-back' conjoined strip typically has pockets arranged to alternate—one on its first side, then one on the other side. It will be appreciated that when so joined together, each component foil strip of the conjoined whole effectively acts as a 'lid foil' for the other.

In one aspect, the elongate form carrier is arranged to have a continuous loop form such as may be achieved by joining the lead end of the strip to the tail end. The loop may be linearly formed or it may be formed as a Mobius strip.

In a particular aspect where the elongate form carrier is in the form of a peelable strip, the base sheet is formed as a continuous loop. In variations, the lid sheet, which forms a peelable sealing lid to the base sheet, may either have continuous loop or non-continuous loop form.

The dispenser has a dispensing mechanism for dispensing the distinct medicament dose portions carried by each of said plural medicament carriers for administration as a single, combination product dose by the patient.

In aspects, some or all components of the dispensing mechanism are common for each of the medicament carriers. The advantage of having common components is that the number of separate parts in the dispenser may be minimised.

In other aspects, the action of those components that are not common may in aspects, be suitably coupled. Coupling is achieved by any suitable fashion including mechanical linkages (e.g. co-gearing or via the use of coupling arms/rods) or electromechanical coupling controls. The advantage of coupling is that the indexing/advancement of each medicament carrier may be achieved in coupled fashion.

In other aspects, most or even all of the components of the dispensing mechanism are distinct. In one particular aspect, the dispenser is arranged such that each of the plural medicament carriers can be indexed/advanced separately thereby providing the opportunity for complex dosing patterns in which any combination, or indeed any one, of the plural strips may be accessed. Where separate indexing/advancement is envisaged separate actuation means (e.g. levers or buttons) may be provided to the dispenser to enable separate actuation thereof.

The mechanism comprises a receiving station for receiving each of the plural medicament carriers. Embodiments are envisaged both in which there is a single receiving station which is capable of receiving plural medicament carriers and also those in which each medicament carrier is received by a distinct (i.e. individual) receiving station. In the latter case, the individual receiving stations may either be coupled or not.

The mechanism further comprises a release for releasing a distinct medicament dose portion from each of the plural medicament carriers on its receipt by the receiving station. The release can have any suitable form. Where the elongate carrier is in the form of a blister strip, the release may for example, comprise means to rupture, puncture, tear or otherwise access the blister. In a particular preferred aspect, where the medicament carrier is in the form of a peelable blister strip the release comprises means for peeling apart the blister strip. In one aspect herein, each blister strip is peeled apart about a defined beak or wedge form feature of the dispenser.

An outlet is positioned to be in communication with the distinct medicament dose portions releasable by said a release to enable their dispensing to the patient. The outlet may have any suitable form. In one aspect, it has the form of a mouthpiece. In another aspect, it has the form of a nozzle for insertion into the nasal cavity of a patient.

The outlet is preferably a single outlet, which communicates with all of the distinct medicament dose portions on their release by said release. Communication is for example, via a common air channelling means (e.g. formed as an airpipe or common manifold). The patient may therefore breathe in through a single outlet, and that breath be transferred through the common air channelling means to (all of) the released medicament dose portions, thereby enabling their inhalation as a combined product. The outlet and/or channelling device may be shaped to encourage mixing of drug as a result of the airflow created by inhalation by the patient. For example, baffles or other mechanical aids to mixing may be incorporated. Venturi channelling of the airflow is also envisaged in embodiments. Helical form channels are envisaged.

The mechanism also comprises an indexer for indexing (e.g. individually) the distinct medicament dose portions of each of the plural medicament carriers. Said indexing typically happens In sequential fashion, for example accessing dose portions sequentially arranged in series along the length of the elongate carrier. The indexing of each carrier may be arranged to occur in coupled fashion, that is to say each is indexed concurrently.

In a preferred aspect, the medicament carrier comprises a peelable blister strip. In this aspect, the release suitably comprises a peeler for peeling apart a base sheet and lid sheet of each peelable strip to open a pocket. Suitably, the peeler includes lid driver for pulling apart a lid sheet from a base sheet of a pocket that has been received at the opening station.

Preferably, there is provided a medicament dispenser for containing plural blister strip form medicament carriers, each having multiple distinct pockets for containing medicament dose portions, wherein said pockets are spaced along the length of and defined between two peelable sheets secured to each other, said dispenser having a dispensing mechanism for dispensing the medicament dose portions contained within said plural medicament carriers, said mechanism comprising, a) an opening station for receiving a pocket of each of said medicament carriers;
b) at least one peeler positioned to engage a base sheet and a lid sheet of a pocket which has been received in said opening station for peeling apart such a base sheet and lid sheet, to open such a pocket;
c) an outlet, positioned to be in communication with an opened pocket through which a user can access a medicament dose portion from such an opened pocket; and
d) at least one indexer for individually indexing the distinct pockets of each of the plural medicament carriers.

In one aspect, a common opening station is provided for receiving a pocket of each of said medicament carriers. In another aspect, distinct opening stations are provided for receiving a pocket of each medicament carrier. Suitably, the distinct opening stations are linking by a communicating passageway or other means for enabling the coming together of the separately released medicaments.

Generally, the opening station(s) are located at a fixed position within the dispenser. In one aspect however, the opening station(s) are movable within the dispenser. The positioning of the opening station(s) may therefore be varied during the course of operation of the dispenser e.g. to act as a compensating means to ensure uniform accessing of pockets over the entire length of a strip form medicament carrier.

In one aspect, each movable opening station comprises a chamber (e.g. of cruciform shape) that in use, moves to locate adjacent respective opened leading pockets of each blister strip. The chamber is suitably provided to a carrier (e.g. bobbin-shaped) that is movably mountable within the dispenser e.g. along a sprung axis.

In the dispenser, each peelable strip form medicament carrier is acted on by a peeler (i.e. peeling means). The peeler engages a base sheet and a lid sheet of a pocket that has been received at the opening station(s) for peeling apart the base sheet and lid sheet to open a pocket. In one aspect, each peelable strip form medicament carrier is acted on by common peeler. In other aspects, each peelable strip is acted on by its own (i.e. separate) peeler.

Suitably, the peeler includes a lid driver for pulling apart a lid sheet and a base sheet of a pocket that has been received at the opening station.

In one aspect, the lid driver comprises a wheel on which the lid sheet is wound up, said wheel having a effective winding surface which remains approximately constant when tension in the lid sheet increases. In one aspect, this is achievable by fashioning the lid driver in 'collapsible wheel' form wherein the wheel collapses (i.e. the diameter of the wheel itself decreases) as lid sheet becomes wound around it to give it an overall approximately constant effective winding diameter (as defined by the diameter of the wheel and the strip wound around it). Suitably, said 'collapsible wheel' comprises a plurality of resiliently flexible arms each extending there from at an angle with respect to a radius. The leading end of the lid sheet is looped over one of said resiliently flexible arms to secure the lid sheet to the wheel initially.

Alternatively, the lid driver comprises a wheel on which the lid sheet is wound up, said lid sheet wheel having an effective winding surface, the effective diameter of which increases after every use of the dispenser as the lid sheet winds around the wheel. Compensation means are then provided to compensate for this increase, which would otherwise lead to a variation in the tension experienced by the lid sheet over its length and hence a variation in its indexing over time.

In one aspect, there is provided a controller comprising means to limit the extent of movement of said lid driver, in order to control the length of medicament carrier peeled by said peeler. Hence, the medicament carrier is indexed by the same amount each time.

In another aspect, the dispenser comprises compensating means positioned between said opening station and said lid sheet wheel for reducing the length of said lid sheet therebetween to compensate for any increase in the diameter of the effective winding surface of the lid sheet wheel during use of the dispenser.

Suitably, the compensating means takes the form of a flexible member. The flexible member may take the form of a flexible elongate arm about which the lid sheet is fed. The arm may flex inwards as tension in the lid sheet increases, and thus shorten the length of lid sheet between the opening station and the lid driver.

Suitably, the flexible member is resilient so that on removal of tension from the lid sheet, the flexible member returns to its rest position. Thus, the internal mechanism can be reloaded with a new medicament carrier after the used carrier is removed.

In one aspect, the compensating means takes the form of a spring that reduces in length as tension increase in the lid sheet between the opening station and the lid driver. Typically a piston head is mounted on one end of the spring about which the lid sheet is fed. The other end of the spring may be fixed. As tension in the lid sheet increases the piston is driven down onto the spring. Preferably, the compensating means takes the form of a sprung-loaded tensioner.

In another aspect, the compensating means takes the form of a torsion spring mounted at the lid driver that provides compensating torsional force to the lid driver such that the tension provided at the lid sheet remains approximately constant over the length of the blister strip.

Alternatively, or in addition, the dispenser comprises a clutch to adjust for any increase in the diameter of the effective winding surface of the lid driver during use of the dispenser. In one aspect, the clutch communicates with the an indexer and the lid driver, and comprises a gearing surface defining plural gear engagement positions; and plural gear teeth for engaging said plural gear engagement positions, wherein the plural gear teeth are arranged such that at any one time only a single gear tooth engages a single gear engagement position.

In use, the clutch acts to compensate for the increase in diameter of said effective winding surface of the lid driver. The clutch allows for slippage when the tension in the lid sheet is greater than the force required to peel apart the lid sheet and the base sheet.

It will be appreciated that in total, the clutch effectively defines a number of individual gear positions that is greater than the number of gear engagement positions. This is therefore advantageous over a traditional slipping clutch arrangement comprising intermeshing gear wheels, where the effective number of individual gear positions defined is either equal to, or no more than, the number of gear engagement positions defined by one of the gear wheels.

Suitably, the gearing surface and plural gear teeth are arranged such that the number of individual gear positions defined is equal to the number of gear engagement positions multiplied by the number of gear teeth. In one example, if the gearing surface defines 60 gear engagement positions and there are 6 gear teeth, then up to 360 individual gear positions are definable (e.g. 1° resolution on a rotating gear system).

Suitably, the gearing surface defines from 20 to 100, preferably from 40 to 80 gear engagement positions. Suitably, the number of gear teeth is from 2 to 20, preferably from 3 to 10.

In one aspect, the gear engagement positions are equally spaced (e.g. equidistantly spaced) and the gear teeth are offset (e.g. non-equidistantly spaced) relative thereto. Such offset arrangement maximises the number of effective individual gear positions that are capable of definition. An example of this aspect, is a Vernier spring arrangement.

In another aspect, the gear engagement positions are also equally spaced (e.g. equidistantly spaced) and the gear teeth are located on a wobbling element capable of wobbling the gear teeth to plural offset (e.g. non-equidistantly spaced) positions. Such a wobbling offset arrangement also maximises the number of effective individual gear positions that are capable of being defined. An example of this aspect, is the wobbling wheel arrangement described herein.

In aspects, the clutch is non-integral with either of the lid driver or the indexer, but forms a separate interconnecting component.

Suitably, the gearing surface comprises a gear wheel. As used herein, the term gear wheel encompasses, for example, a wheel, spindle or spool. Suitably, the gear teeth may be arranged to be in ratchet form (i.e. enabling movement in one direction only). Suitably, the gearing surface and gear teeth are in biased (e.g. sprung) engagement.

In another aspect, the lid driver comprises a mangle. The lid sheet passes through two rotating wheels that act as a mangle and is gripped at the point of contact with the wheels. The used portion of the lid sheet is collected in a chamber after it has passed through the mangle.

In another aspect, the lid driver comprises a roller. Suitably said roller is composed of a polymeric rubber and is positioned next to a guide wall. Suitably said roller has a smooth surface. Alternatively said roller has a knurled surface. The roller grips the lid sheet as it passes from the point at which it is separated from the base sheet through the space between the roller and the guide wall and the used portion of the lid sheet is then collected in a chamber. The roller has the advantage over the mangle described above in that a greater degree of contact between the roller wheel and the lid sheet occurs— the lid sheet is squeezed through the roller and may pass around about ⅓ of the roller wheel. This provides a higher level of grip and pulling force than with a mangle. The force required to turn the roller is constant throughout the use of the device and does not vary according to how much of the lid sheet has been peeled away from the base sheet. This is in contrast to the wheel described above where the forces required to turn the wheel may vary due to the fact that the lid sheet is wound around the wheel. The lid sheet is not wound around the roller. The roller also has the advantage that the lid sheet does not have to be looped around or fixed to the roller before use of the device, therefore simplifying assembly of the device and reducing costs.

In another aspect, the lid driver comprises a lid spool. Suitably, the lid spool comprises a toothed wheel with a central upward cylindrical projection on which the lid sheet may be wound when it has been separated from the base sheet. The lid spool may have a mechanical gearing mechanism which is driven on actuation of the dispenser; the lid sheet is pulled away from the base sheet and wound onto the lid spool, causing the rotatable indexing wheel to turn and index the base sheet by one dose. An interlock coupling, as described supra, may be moved along the base of the rotatable indexing wheel until it fits into the next base recess. The positioning of the interlock coupling in this recess limits the movement of the lid spool to the distance between two pockets on the base sheet and therefore prevents the amount of lid sheet which is wound around the lid spool from increasing as the diameter of the lid spool is increased.

In another aspect, the lid driver comprises a spiked wheel. As the spiked wheel turns, the lid sheet is pulled over it and the spikes perforate parts of the lid sheet to improve the grip on the lid sheet. The lid sheet then passes out into a chamber where it collects.

In another aspect, the lid driver comprises a clamp system. The clamp system comprises at least one angled spring that is pivotable at one end and grips the lid sheet at the other end. The clamp system is moved in the direction that the lid sheet is to be pulled and grips the lid sheet, pulling it and therefore peeling it away from the base sheet. The clamp system is then moved back to its rest position. This results in the spring pivoting and clamping the lid sheet, therefore preventing the lid sheet from being further peeled from the base sheet.

In another aspect, the used portion of the lid sheet may be passed around rollers and fed back onto the used portion of the base sheet after the medicament has been accessed to join back onto the base sheet. The lid sheet may be coated with a sticky substance to aid resealing. The use of this mechanism saves space, as the used portions of the blister strip will be collected in the same area.

In another aspect, the unopened medicament carrier (e.g. coiled blister strip) may be surrounded by a constant force spring. Alternatively, the unused blister strip may be surrounded by an elastomeric band or band comprising a contractible material. The constant force spring, elastomeric band or band comprising a contractible material contracts as the coil reduces in size.

Suitably, the dispenser comprises a guide for guiding the lid sheet and base sheet along separate paths at the opening station. The lid sheet is passed around the guide portion onto the lid driver. In one aspect, the guide comprises a roller mechanism. The lid sheet is fed over the rollers onto the lid driver.

The mechanism includes an indexer for individually indexing the distinct pockets of each of the plural medicament carriers. Suitably, the an indexer comprises a rotatable index wheel having recesses therein, said index wheel being engageable with a medicament carrier in use with said medicament dispenser such that said recesses each receive a respective pocket of the base sheet of a blister strip in use with said medicament dispenser.

Suitably, the rotatable index wheel additionally comprises a series of indentations located at its base and spaced in between the recesses.

Suitably, the indexer additionally comprises an interlock coupling to couple actuation of the dispenser to the index wheel. The interlock coupling reversibly locks the index wheel in place. Preferably, said interlock coupling comprises a foot portion having a toe and a heel, and a tail section. Preferably, said interlock coupling is pivotally mountable to the dispenser at its foot portion. Preferably, said toe fits into one of the indentations on the rotatable index wheel. Preferably, the interlock coupling is sprung to bias it towards location of the toe in one of the indentations.

Alternatively, the indexer comprises a gear and sprocket wherein teeth on the wheel fit into apertures or holes formed on one or both edges of a medicament carrier. The mechanism therefore resembles that of photographic film being advanced through a camera.

Alternatively, the indexer comprises an index ratchet that is moveable between a locked position whereby said ratchet engages a pocket on said medicament carrier and prevents further peeling thereof, and a release position allowing free movement of said medicament carrier. In this embodiment, actuation of said medicament dispenser actuates said lid driver and releases said index ratchet from a medicament carrier to allow peeling thereof.

Suitably, the dispenser additionally comprises a first chamber in which at least one medicament carrier is initially housed and from which it is dispensed and a second chamber to receive the used portion of the base sheet after it has been indexed around the index wheel and separated from the lid sheet. Suitably, said first chamber and said second chamber are separable by a wall. In one aspect, said wall is movable to adjust the size of said first and second chambers. In another aspect, the wall is pivotally mountable. Alternatively the wall is slidably mountable.

Suitably, the internal mechanism further comprises a third chamber to receive the used portion of the lid sheet and a fourth chamber which houses the index ratchet. The fourth chamber may communicate via a slit, which in turn extends upwardly within a mouthpiece and communicates with air inlets.

Suitably, the dispenser additionally comprises a crushing wheel to crush the base sheet after the medicament has been removed from the pockets thereof. The crushing wheel therefore reduces the space that the used portion of the base sheet takes up.

Any or all components of the dispensing mechanism may be driven by either an electronic or mechanical drive system or combination thereof.

Suitably electronic drive means typically comprise a motor, preferably an electrically powered motor. The motor may provide linear or rotary drive, but in general, rotary motors are most suitable. The motor may for example, comprise a DC electric motor, a piezoelectric (PZ) motor, an ultrasonic motor, a solenoid motor or a linear motor. Preferably, the electronic drive system comprises a DC motor, a PZ motor or an ultrasonic motor.

The use of ultrasonic motors is particularly preferred since they offer advantages over conventional motors in terms of weight, size, noise, cost and torque generated. Ultrasonic motors are well known in the art and are commercially available (e.g. BMSTU Technological Cooperation Centre Ltd, Moscow, Russia; Shinsei Corporation, Tokyo, Japan).

Ultrasonic motors do not use coils or magnets but comprise a piezo-electric ceramic stator that drives a coupled rotor. The stator generates ultrasonic vibrations, which in turn causes rotation of the rotor. While regular DC motors are characterised by high speed and low torque, requiring reduction gearing to increase torque, ultrasonic motors attain low speed and high torque, thus eliminating the need for reduction gearing. Furthermore, these motors are lightweight and compact, lacking coils and magnets, and are noiseless as the ultrasonic frequencies used are not audible to the human ear.

Suitably, the dispenser further comprises actuating means for actuating a manual or electronic drive system. Said actuating means may take the form of a switch, push-button, or lever.

In one particular aspect, the dispenser herein is configured to be reloadable. In particular, each medicament carrier is suitably provided within a reloadable cassette.

In particular, the dispenser herein is configured to comprise a body; a holder, shaped to fit within said body and movable relative to said body; and receivable by said holder, a cassette containing plural elongate form medicament carriers.

Suitably, any drive system (e.g. electronic) is located in either the body or the holder part, and the cassette comprises the minimum number of component (i.e. internal mechanism) parts. In embodiments, the body/holder including the (e.g. electronic) drive is retainable by the user and the cassette is sold as a refill/reload component that is discarded after use. By locating an electronic drive system in the body/holder, the amount of electronic components that are discarded is minimised which is advantageous from an environmental standpoint.

Suitably, the cassette of the reloadable form medicament dispenser herein comprises
a) an opening station for receiving a pocket of each of the plural form medicament carriers;
b) a peeler positioned to engage a base sheet and a lid sheet of a pocket which has been received in said opening station for peeling apart such a base sheet and lid sheet, to open such a pocket;
c) an outlet, positioned to be in communication with an opened pocket through which a user can access a medicament dose portion from such an opened pocket; and
d) an indexer for individually indexing the distinct pockets of each of the plural medicament carriers.

Suitably, movement of the holder relative to the body results in movement of the cassette between a first position and a second position such that the cassette is reversibly removable from the holder when the cassette is in the second position.

Suitably the first position comprises a dispensing position. Preferably the second position comprises a non-dispensing position. The cassette is therefore only removable from the holder when the cassette is in the non-dispensing position.

Suitably, the holder and body include attaching means to attach the holder to the body. Preferably, said attaching means comprise a snap fit mechanism. Suitably said snap fit mechanism comprises a pin and hole system.

Suitably, the holder is pivotally movable relative to the body. Alternatively the holder is rotationally movable relative to the body.

Suitably the holder additionally comprises a stop to limit movement of the holder relative to the body. The stop abuts against the edge of the body at two points when it is rotated. At these points the holder may be designed to click into place. Therefore when the stop abuts one body edge then it is clicked into the dispensing position and when the stop abuts the other body edge then it is clicked into the non-dispensing position. Alternatively the holder is slidably movable relative to the body.

Suitably, the holder additionally comprises a catch to retain the cassette. The catch may for example comprise a sprung pin which fits into a hole or an integral catch which deforms when pressed allowing removal of the cassette.

Suitably, the catch is child resistant. Child resistance may be realised by having a system which forces the user to perform two actions at once to remove the cassette.

Other features of the catch may include shock or impact resistance, the ability to lock the catch and orientation features to ensure that the cassette can only be inserted one way. The catch should also be easy to manufacture and assemble, be robust, be composed of a minimal number of components and intrude minimally into the space into which the cassette is inserted.

Suitably, the holder includes guide means to guide the cassette into the holder. Preferably said guide means comprise guide rails. Alternatively the guide means comprise grooves, indentations or other shaping or surface details to define a 'lock and key' relationship between the holder and the cassette. Colour guides, arrows and any other surface markings may also be employed.

Suitably, the cassette additionally comprises means to actuate the dispenser. The actuating means may take the form of a switch, push-button or lever.

Suitably, the cassette additionally comprises a mouthpiece. Suitably, said mouthpiece is extendable. The mouthpiece extends as the cassette and holder are moved from the non-dispensing position to the dispensing position. Alternatively the mouthpiece is retractable. The mouthpiece retracts as the cassette and holder are moved from the dispensing position to the non-dispensing position. In one aspect, the mouthpiece is telescopic. In another aspect, the mouthpiece is fixed.

The medicament dispenser may also be designed for nasal inhalation of a powdered medicament and may therefore incorporate a nozzle as an alternative to a mouthpiece. If the medicament is in solid form, the dispenser may incorporate an exit channel for tablet release.

Suitably, the body covers the mouthpiece and an indexer (and any actuator therefor) when the cassette is in the non-dispensing position. This avoids the need for a separate cover and protects the mouthpiece from the ingress of dirt and contaminants during storage.

Suitably, the cassette additionally comprises a raised portion to fit against the holder. The raised portion is located at the opposite end of the cassette to the mouthpiece/nosepiece/exit and indexing lever and prevents the incorrect insertion of the cassette into the holder since it is too wide to fit into the holder. The raised portion is shaped such that it fits against a cut away part of the holder. Preferably said raised portion includes a section which is raised to define a grip portion.

Suitably, at least a portion of the holder and body is shaped for ease of grip by the user.

The medicament dispenser in reloadable form may be supplied as a kit of parts. A first part of the kit comprises a body; a holder, shaped to fit within said body and movable relative to said body; and within said holder a receiving station for receipt of a cassette. A second part of the kit comprises a cassette containing plural elongate form medicament carriers and a dispensing mechanism for indexing said plural elongate forms medicament carriers, wherein the cassette is receivable by the receiving station and movement of the holder relative to the body results in movement of the cassette between a first position and a second position such that the cassette is reversibly removable from the receiving station when the cassette is in the second position. Suitably, the holder also comprises an electronic drive system for driving the indexing mechanism of the cassette.

In one aspect, the reloadable dispenser is assembled as follows. The holder is snap fitted into the body. The cassette is assembled separately. The body of the cassette is formed, preferably in two sections with any necessary spindles or integral components formed into the base. Individual components such as indexing wheels, lid winding mechanisms, guide portions etc are then assembled into the base. Finally the plural elongate form medicament carriers (e.g. blister strips) are inserted into the cassette. These may be wound into the dispenser before the lid is attached to the cassette and the cassette sealed. Alternatively, the cassette may be formed completely apart from a hole left in its side for insertion of the medicament carriers. The hole may then be sealed to complete the cassette. This second method of inserting the medicament carriers into the device has the advantage that it is much simpler.

Suitably, the medicament dispenser herein comprises an actuation or dose counter for counting the number of actuations of the indexing lever or releases of dose from the cassette. The dose counter may count the number of doses left to be taken or the number of doses taken. In one aspect, the dose counter is electronic. Alternatively said dose counter is mechanical.

In one aspect, the blister strip has printed numbers on it corresponding to the doses in the pockets. Preferably, said printed numbers are visible through a window in the body of the dispenser or any cassette reload therefor.

Suitably, the medicament dispenser additionally comprises an electronic data management system. The electronic data management system has input/output capability and comprises a memory for storage of data; a microprocessor for performing operations on said data; and a transmitter for transmitting a signal relating to the data or the outcome of an operation on the data.

Suitably, the electronic data management system is arranged to be responsive to or activated by the voice of a user. Thus, for example the system may be switched on or off in response to a voice command.

The electronic data management system may be integral with the body of the dispenser. Alternatively, the electronic data management system forms part of a base unit which is reversibly associable with the body.

Suitably, the medicament dispenser additionally comprises a data input system for user input of data to the electronic data management system. Preferably, the data input system comprises a man machine interface (MMI) preferably selected from a keypad, voice recognition interface, graphical user interface (GUI) or biometrics interface.

Energy may be conserved by a variety of means to enable the dispenser to operate for longer on a given source of energy, such as a battery. Energy conservation or saving methods have additional advantages in terms of reducing the size requirements of the power source (e.g. battery) and thus the weight and portability of the medicament dispenser.

A variety of energy saving methods is available which generally involve reducing power consumption. One such method is to use a clock or timer circuit to switch the power on and off at regular or predetermined intervals. In another method the system can selectively switch on/off specific electronic devices, such as visual display units or sensors, in order to power these devices only when they are required to perform a particular sequence of events. Thus different electronic devices may be switched on and off at varying intervals and for varying periods under control of the system. The power sequencing system may also respond to a sensor, such as a motion or breath sensor, which is activated on use of the device.

Low power or "micropower" components should be used within the electronics where possible and if a high power device is required for a particular function this should be put into a low power standby mode or switched off when not required. Similar considerations apply in the selection of transducers. Operation at low voltage is desirable since power dissipation generally increases with voltage.

For low power digital applications complementary metal oxide semi-conductor (CMOS) devices are generally preferred and these may be specially selected by screening for low quiescent currents. Clock speeds of processors and other logic circuits should be reduced to the minimum required for computational throughput as power consumption increases with frequency. Supply voltages should also be kept at minimal values consistent with reliable operation because power dissipation in charging internal capacitance's during switching is proportional to the square of the voltage. Where possible, supply voltages should be approximately the same throughout the circuit to prevent current flowing through input protection circuits. Logic inputs should not be left floating and circuits should be arranged so that power consumption is minimised in the most usual logic output state. Slow logic transitions are undesirable because they can result in relatively large class-A currents flowing. Resistors may be incorporated in the power supply to individual devices in order to minimise current in the event of failure.

In some control applications, devices that switch between on and off states are preferred to those that allow analog (e.g. linear) control because less power is dissipated in low resistance on states and low current off states. Where linear components are used (e.g. certain types of voltage regulators) then types with low quiescent currents should be selected. In some circuit configurations it is preferable to use appropriate reactive components (i.e. inductors and capacitors) to reduce power dissipation in resistive components.

Suitably, the system additionally comprises a visual display unit for display of data from the electronic data management system to the user. The display may for example, comprise a screen such as an LED or LCD screen. More preferably the visual display unit is associable with the body of the medicament dispenser.

Suitably, the medicament dispenser additionally comprises a datalink for linking to a local data store to enable communication of data between the local data store and the electronic data management system. The datastore may also comprise data management, data analysis and data communication capability.

The datastore may itself form part of a portable device (e.g. a handheld device) or it may be sized and shaped to be accommodated within the patient's home. The datastore may also comprise a physical storage area for storage of replacement cassettes. The datastore may further comprise a system for refilling medicament from a reservoir of medicament product stored therewithin. The datastore may further comprise an electrical recharging system for recharging any electrical energy store on the medicament dispenser, particularly a battery recharging system.

The datalink may for example enable linking with a docking station, a personal computer, a network computer system or a set-top box by any suitable method including a hardwired link, an infrared link or any other suitable wireless communications link.

Suitably, the medicament dispenser additionally comprises an actuation detector for detecting actuation of the dispensing mechanism wherein said actuation detector transmits actuation data to the electronic data management system.

The medicament dispenser may additionally comprise a safety mechanism to prevent unintended multiple actuations of the dispensing mechanism. The patient is thereby protected from inadvertently receiving multiple doses of medicament in a situation where they take a number of short rapid breaths. More preferably, the safety mechanism imposes a time delay between successive actuations of the release. The time delay is typically of the order of from three to thirty seconds.

Suitably, the medicament dispenser additionally comprises a release detector for detecting release of medicament from the cassette, wherein said release detector transmits release data to the electronic data management system.

Suitably, the medicament dispenser additionally comprises a shake detector for detecting shaking of the medicament container (e.g. prior to actuation of the dispensing mechanism), wherein said shake detector transmits shake data to the electronic data management system.

Suitably, any actuation detector, release detector, or shake detector comprises a sensor for detecting any suitable parameter such as movement. Any suitable sensors are envisaged including the use of optical sensors. The release detector may sense any parameter affected by release of the medicament such as pressure, temperature, sound, moisture, carbon dioxide concentration and oxygen concentration.

Suitably, the medicament dispenser additionally comprises a breath trigger for triggering the dispensing mechanism, said breath trigger being actuable in response to a trigger signal from the electronic data management system. Preferably, the electronic data management system includes a predictive algorithm or look-up table for deriving from the breath data when to transmit the trigger signal. For example, a real-time analysis of the patient breath waveform may be made and the trigger point derived by reference to that analysed waveform.

Suitably, the electronic data management system includes a predictive algorithm or look-up table for calculating the optimum amount of medicament to dispense.

Suitably, the memory on the electronic data management system includes a dose memory for storing dosage data and reference is made to the dose memory in calculating the optimum amount of medicament to dispense.

Suitably, the medicament dispenser additionally comprises a selector for selecting the amount of medicament to dispense from said dispensing mechanism. In one aspect, the selector is manually operable. In another aspect, the selector is operable in response to a signal from the transmitter on the electronic data management system.

Suitably, the medicament dispenser comprises in association with a body or housing thereof, a first transceiver for transmitting and receiving data and in association with the medicament container, a second transceiver for transmitting and receiving data, wherein data is transferable in two-way fashion from the first transceiver to the second transceiver. The data is preferably in digital form and suitable for transfer by electronic or optical means.

One advantage of embodiments of this type is the ability to store many types of information in different parts of the memory structure of the transceivers. The information is furthermore stored in a form which is readily and accurately transferable. The information could for example, include manufacturing and distribution compliance information written to the memory at various points in the manufacturing or distribution process, thereby providing a detailed and readily accessible product history of the dispenser. Such product history information may, for example, be referred to in the event of a product recall. The compliance information could, for example, include date and time stamps. The information could also include a unique serial number stored in encrypted form or in a password protectable part of the memory which uniquely identifies the product and therefore may assist in the detection and prevention of counterfeiting. The information could also include basic product information such as the nature of the medicament and dosing information, customer information such as the name of the intended customer, and distribution information such as the intended product destination.

On loading or reloading the medicament dispenser with a cassette the second transceiver may, for example, read the unique serial number, batch code and expiry date of the medicament and any other information on the second transceiver. In this way the nature and concentration of the medicament, together with the number of doses used or remaining within the cassette, may be determined. This information can be displayed to the patient on a visual display unit. Other information, such as the number of times the medicament dispenser has been reloaded with a cassette, may also be displayed.

Similarly, should the cassette be removed from the holder before the supply of medicament is exhausted, the same data can be read from the second transceiver and the number of doses remaining or used determined. Other information, such as the date and time of administration of the drug, or environmental exposure data such as the minimum/maximum temperatures or levels of humidity the cassette has been exposed to, may also be read and displayed to the user.

In the event that the supply of medicament within the container becomes exhausted, or that the shelf life of the medicament has expired, or that the first transceiver does not recognise the batch code on the second transceiver, activation of the dispenser may be prevented to safeguard the user. Activation may also be prevented if the medicament has been exposed to extreme environmental conditions for periods outwith the manufacturer's guidelines.

Data may be transferred to and from any transceiver during the period of use of the medicament dispenser by the patient. For example, the medicament dispenser may include an electronic data management system having various sensors associated therewith. Any data collected by the sensors or from any data collection system associated with the electronic data management system including a clock or other date/time recorder is transferable.

Data may be transferred each time the patient uses the dispenser. Or alternatively, data may be stored in a database memory of the electronic data management system and periodically downloaded to any transceiver. In either case, a history of the usage of the dispenser may be built up in the memory of a transceiver.

In one embodiment herein, a history of the usage of the medicament dispenser is transferred to the second transceiver. When the medicament carriers in the cassette are exhausted, the cassette is exchangeable by the patient for a new refill cassette. At the point of exchange, which will typically occur at the pharmacy, data may be transferred from the exhausted cassette to the refill and vice-versa. Additionally, usage history data may be read from the refill and transferred to a healthcare data management system for example comprising a network computer system under the control of a healthcare data manager.

Methods are envisaged herein whereby the patient is given some sort of reward for returning the refill and making available the data comprised within the second transceiver. Methods are also envisaged herein whereby the healthcare data manager is charged for either receipt of the data from the second transceiver or for its use for commercial purposes. Any rewards or charging may be arranged electronically. The methods may be enabled by distributed or web-based computer network systems in which any collected data is accessible through a hub on the network. The hub may incorporate various security features to ensure patient confidentiality and to allow selective access to information collected dependent upon level of authorisation. The level of user authorisation may be allocated primarily to safeguard patient confidentiality. Beyond this the level of user authorisation may also be allocated on commercial terms with for example broader access to the database being authorised in return for larger commercial payments.

Suitably, the first and second transceiver each comprise an antenna or equivalent for transmitting or receiving data and connecting thereto a memory. The memory will typically comprise an integrated circuit chip. Either transceiver may be configured to have a memory structure which allows for large amounts of information to be stored thereon. The memory structure can be arranged such that parts of the memory are read-only, being programmed during/after manufacture, other parts are read/write and further parts are password protectable. Initial transfer of information (e.g. on manufacture or one dispensing) to or from any transceiver can be arranged to be readily achievable by the use of a reader which is remote from the medicament dispenser, thereby minimising the need for direct product handling. In further aspects, the reader can be arranged to simultaneously read or write to the memory of multiple transceivers on multiple medicament dispensers.

A suitable power source such as a battery, clockwork energy store, solar cell, fuel cell or kinetics-driven cell will be provided as required to any electronic component herein. The power source may be arranged to be rechargeable or reloadable.

Suitably, data is transferable in two-way fashion between the first and second transceiver without the need for direct physical contact therebetween. Preferably, data is transferable wirelessly between the first and second transceiver.

Suitably, the first transceiver is an active transceiver and the second transceiver is a passive transceiver. The term active is used to mean directly-powered and the term passive is used to mean indirectly-powered.

Suitably, the second transceiver comprises a label or tag comprising an antenna for transmitting or receiving energy; and an integrated circuit chip connecting with said antenna, and the first transceiver comprises a reader for said label or tag. In this case the label or tag is a passive transceiver and the reader is an active transceiver. Preferably, the reader will not need to be in direct contact with the tag or label to enable the tag or label to be read.

The tag may be used in combination and/or integrated with other traditional product labelling methods including visual text, machine-readable text, bar codes and dot codes.

Suitably, the integrated circuit chip has a read only memory area, a write only memory area, a read/write memory area or combinations thereof.

Suitably, the integrated circuit chip has a one-time programmable memory area. More preferably, the one-time programmable memory area contains a unique serial number.

Suitably, the integrated circuit chip has a preset memory area containing a factory preset, non-changeable, unique data item. The preset memory item is most preferably in encrypted form.

Suitably, the integrated circuit chip has plural memory areas thereon. Suitably, any memory area is password protected.

Suitably, any memory area contains data in encrypted form. Electronic methods of checking identity, error detection and data transfer may also be employed.

In one aspect, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

Suitably, the tag is on a carrier and the carrier is mountable on the body or holder of the medicament dispenser or on the cassette.

In one aspect, the carrier is a flexible label. In another aspect, the carrier is a rigid disc. In a further aspect, the carrier is a rectangular block. In a further aspect, the carrier is a collar ring suitable for mounting to the neck of an aerosol container. Other shapes of carrier are also envisaged.

Suitably, the carrier is mouldable or weldable to the cassette or housing. Suitably, the carrier encases the tag. More preferably, the carrier forms a hermetic seal for the tag. In one aspect, the carrier comprises an insulating material such as a glass material or, a paper material or an organic polymeric material such as polypropylene. Alternatively, the carrier comprises a ferrite material.

The energy may be in any suitable form including ultrasonic, infrared, radiofrequency, magnetic, optical and laser form. Any suitable channels may be used to channel the energy including fibre optic channels.

In one aspect, the second transceiver comprises a radiofrequency identifier comprising an antenna for transmitting or receiving radiofrequency energy; and an integrated circuit chip connecting with said antenna, and the first transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or label to be read.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

Suitably, the antenna of the RFID tag is capable of transmitting or receiving radiofrequency energy having a frequency of from 100 kHz to 2.5 GHz. Preferred operating frequencies are selected from 125 kHz, 13.56 MHz and 2.4 GHz.

In one aspect, the second transceiver comprises a magnetic label or tag comprising an antenna for transmitting or receiving magnetic field energy; and an integrated circuit chip connecting with said antenna, and the first transceiver comprises a reader for said magnetic label or tag. In this case the magnetic label or tag is a passive transceiver and the reader is an active transceiver.

A suitable magnetic label or tag comprises plural magnetic elements in mutual association whereby the magnetic elements move relative to each other in response to an interrogating magnetic field. A magnetic label or tag of this type is described in U.S. Pat. No. 4,940,966. Another suitable magnetic label or tag comprises a magnetorestrictive element which is readable by application of an interrogating alternating magnetic field in the presence of a magnetic bias field which results in resonance of the magnetorestrictive elements at different predetermined frequencies. A magnetic label of this type is described in PCT Patent Application No. WO92/12402. Another suitable magnetic label or tag comprising plural discrete magnetically active regions in a linear array is described in PCT Patent Application No. WO96/31790. Suitable magnetic labels and tags include those making use of Programmable Magnetic Resonance (PMR) (trade name) technology.

In another aspect, the second transceiver comprises a microelectronic memory chip and the first transceiver comprises a reader for said microelectronic memory chip. The microelectronic memory chip may comprise an Electrically Erasable Programmable Read Only Memory (EEPROM) chip or a SIM card-type memory chip. In this case the microelectronic memory chip is a passive transceiver and the reader is an active transceiver.

Any transceiver herein, particularly a passive transceiver may be mounted on or encased within any suitable inert carrier. The carrier may comprise a flexible sheet which may in embodiments be capable of receiving printed text thereon.

In one aspect, the first transceiver is integral with the body such that a single unit is comprised. The first transceiver may for example be encased within or moulded to the body.

In another aspect, the first transceiver forms part of a base unit which is reversibly associable with the body. The base unit may for example, form a module receivable by the body such as a snap-in module.

Suitably, the medicament dispenser additionally comprises a communicator for wireless communication with a network computer system to enable transfer of data between the network computer system and the electronic data management system. Dispensers employing such communicators are described in pending PCT Applications No.s PCT/EP00/09291 (PG3786), PCT/EP00/09293 (PG4029) and PCT/EP00/09292 (PG4159). Preferably, the communicator enables two-way transfer of data between the network computer system and the electronic data management system.

Suitably, the data is communicable between the network computer system and the electronic data management system in encrypted form. All suitable methods of encryption or partial encryption are envisaged. Password protection may also be employed. Suitably, the communicator employs radiofrequency or optical signals.

In one aspect, the communicator communicates via a gateway to the network computer system. In another aspect, the communicator includes a network server (e.g. a web server) such that it may directly communicate with the network.

In a further aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

In one aspect, the network computer system comprises a public access network computer system. The Internet is one suitable example of a public access network computer system, wherein the point of access thereto can be any suitable entrypoint including an entrypoint managed by an Internet service provider. The public access network computer system may also form part of a telecommunications system, which may itself be either a traditional copper wire system, a cellular system or an optical network.

In another aspect, the network computer system comprises a private access network computer system. The private access network system may for example, comprise an Intranet or Extranet that may for example, be maintained by a health service provider or medicament manufacturer. The network may for example include password protection; a firewall; and suitable encryption means.

Preferably, the communicator enables communication with a user-specific network address in the network computer system.

The user-specific network address may be selected from the group consisting of a web-site address, an e-mail address and a file transfer protocol address. Preferably, the user-specific network address is accessible to a remote information source such that information from said remote information source can be made available thereto. More preferably, information from the user-specific network address can be made available to the remote information source.

In one aspect, the remote information source is a medicament prescriber, for example a doctors practice. Information transferred from the medicament prescriber may thus, comprise changes to prescription details, automatic prescription updates or training information. Information transferred to the medicament prescriber may comprise compliance information, that is to say information relating to the patient's compliance with a set prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

In another aspect, the remote information source is a pharmacy. Information transferred from the pharmacy may thus, comprise information relating to the medicament product. Information sent to the pharmacy may thus include prescription requests which have been remotely pre-authorised by the medicament prescriber.

In a further aspect, the remote information source is an emergency assistance provider, for example a hospital accident and emergency service or an emergency helpline or switchboard. The information may thus, comprise a distress or emergency assist signal which requests emergency assistance.

In a further aspect, the remote information source is a manufacturer of medicament or medicament delivery systems. Information transferred to the system may thus, comprise product update information. The system may also be configured to feed information back to the manufacturer relating to system performance.

In a further aspect, the remote information source is a research establishment. In a clinical trial situation, information may thus be transferred relating to the trial protocol and information relating to patient compliance fed back to the research establishment.

In a further aspect, the remote information source is an environmental monitoring station. Information relating to weather, pollen counts and pollution levels may thus be made accessible to the system.

Suitably, the medicament dispenser additionally comprises a geographic positioning system such as a global positioning system or a system that relies on the use of multiple communications signals and a triangulation algorithm.

According to another aspect of the present invention there is provided the use of the dispenser herein for dispensing a combination medicament product.

BRIEF DESCRIPTION OF THE DRAWINGS

The invention will now be described with reference to the accompanying drawings in which:

FIGS. 4b and 4c show side views of the inner workings of the holder of the holder//body shown in FIG. 4a;

FIGS. 4d and 4e show side views of the inner workings of the cassette shown in FIG. 4a;

FIG. 6b shows a perspective view of a detail of the dispenser of FIG. 6a;

FIG. 7 shows a dual strip arrangement for use in accord with the invention in which the pockets of one strip form medicament carrier are enlarged in comparison to those of another strip form medicament carrier;

FIG. 8 shows another dual strip arrangement for use in accord with the invention in which the pockets of one strip form medicament carrier are double-spaced in comparison to those of another strip form medicament carrier;

FIG. 25a shows a sectional plan view of a further medicament dispenser in accord with the invention and FIG. 25b shows a close up view of a feature of the dispenser of FIG. 25a.

DETAILED DESCRIPTION OF THE DRAWINGS

Figure 1:
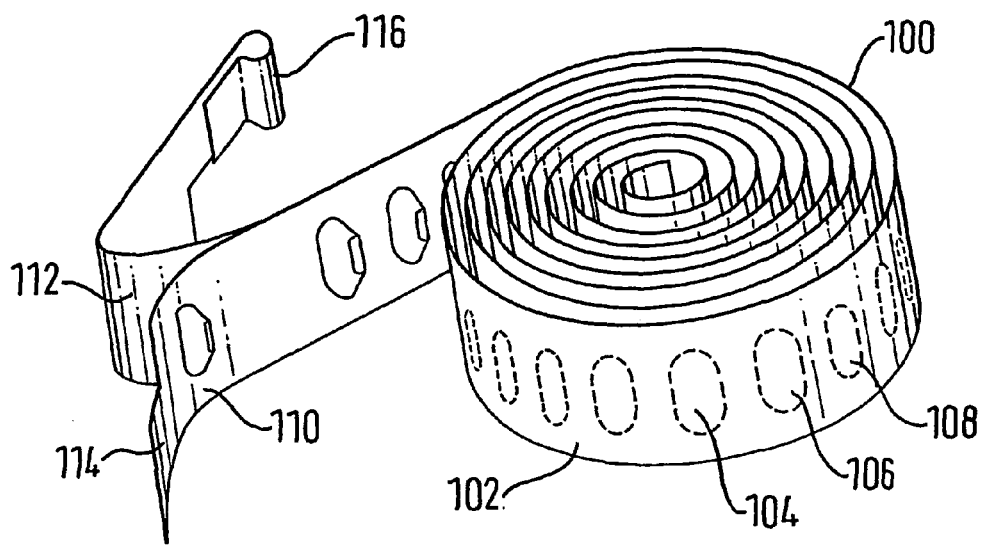
FIG. 1 shows a perspective view of a medicament carrier suitable for use in accord with the dispenser of the present invention.

FIG. 1 shows a medicament carrier 100 suitable for use in accord with the present invention. The medicament carrier comprises a flexible strip 102 defining a plurality of pockets 104, 106, 108 each of which contains a portion of a dose of medicament of a form suitable for inhalation and in the form of powder. In accord with the present invention, plural such strips 102 are typically employed in a single medicament dispenser, wherein each strip provides the component medicament dose portions of a combination medicament product. Each strip may be of the same size and/or contain the same dose amount (e.g. volume or mass) or in alternative embodiments, strips of different sizes and/or containing different dose amounts may be employed in combination.

The strip comprises a base sheet 110 in which blisters are formed to define the pockets 104, 106, 108 and a lid sheet 112 which is hermetically sealed to the base sheet except in the region of the blisters in such a manner that the lid sheet 112 and the base sheet 110 can be peeled apart. The sheets 110, 112 are sealed to one another over their whole width except for the leading end portions 114, 116 where they are preferably not sealed to one another at all.

The lid 112 and base 110 sheets are each formed of a plastics/aluminium laminate and are suitably adhered to one another by heat sealing. The lid sheet 112 comprises at least the following successive layers: (a) paper; adhesively bonded to (b) polyester; adhesively bonded to (c) aluminium foil; that is coated with a heat seal lacquer for bonding to the base sheet. The base sheet 110 comprises at least the following successive layers: (a) oriented polyamide (OPA); adhesively bonded to (b) aluminium foil; adhesively bonded to (c) a third layer comprising a polymeric material (e.g. polyvinyl chloride).

The strip 102 is shown as having elongate pockets 104, 106, 108 which run transversely with respect to the length of the strip 102. This is convenient in that it enables a large number of pockets 104, 106, 108 to be provided in series arrangement along a given strip 102 length. The strip 102 may, for example, be provided with sixty or one hundred pockets but it will be understood that the strip 102 may have any suitable number of pockets.

Figure 2:
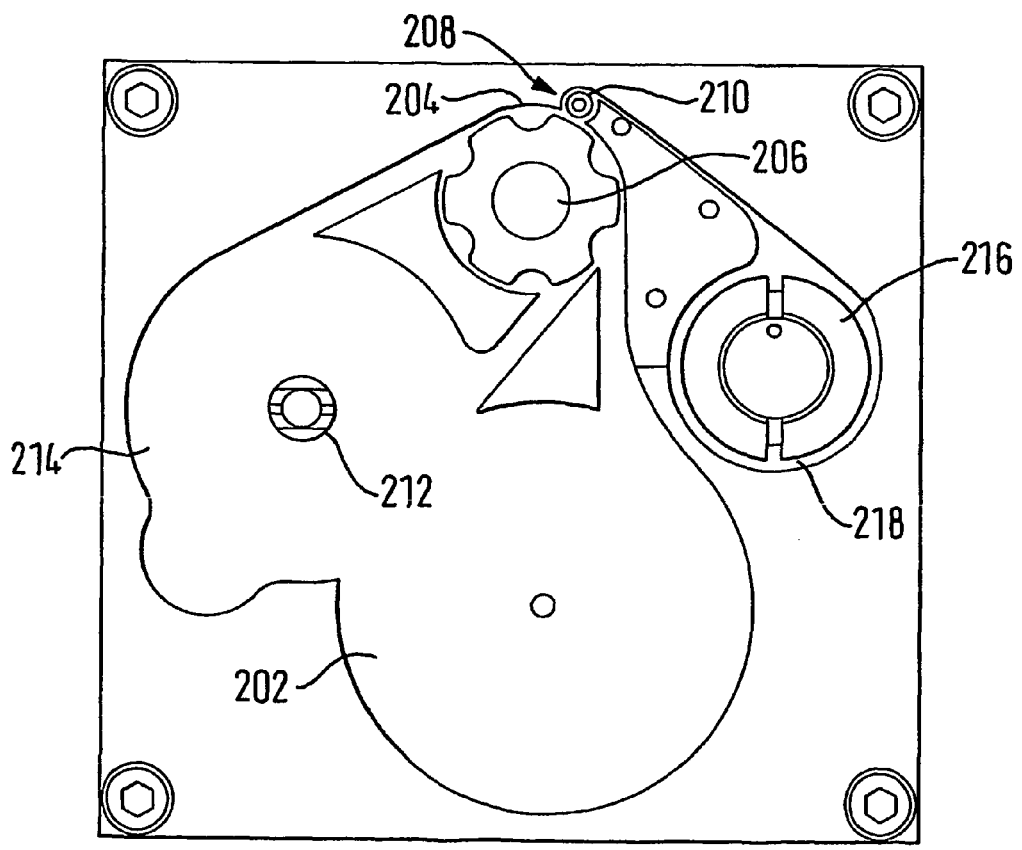
FIG. 2 shows a base unit of a medicament dispenser in accord with one aspect of the invention.

FIG. 2 illustrates a base unit 200 of a medicament dispenser according to one aspect of the invention. In use, plural blister strips (not shown for clarity) are positioned, one on top of each other, in chamber 202 of the base unit 200. The blister strips are pre-fed through a guide member 204 within the manifold component and each engaged in a six-pocket index wheel 206. The first pocket of each blister strip is positioned one pocket away from the opening station 208. The lid foil and base foil are separable about a beak 210. The resulting empty base foil is coiled about a base take-up spindle 212 in the base take-up chamber 214. The used lid foil is fed over the beak 210 and coiled about a lid take-up spindle 216 in the lid take-up chamber 218.

The dispenser is actuated by pressing a button on the side of the dispenser (not shown) that activates a DC motor (not shown for clarity) to index the internal mechanism by one pocket of medicament. The DC motor thus indexes each strip and coils up the waste foils.

Initially, the gearing between the index wheel 206 and the lid take-up foil spindle 216 is one-to-one. However, as the lid take up spindle 216 winds on more foil, its effective winding diameter increases. An increase in diameter would cause the lid take-up spindle 216 to pull more strip than the index wheel 206 releases. Thus, in this particular example, compensation is provided for the increase in lid spool diameter by adjusting the amount the lid spool rotates over time.

Figure 3:
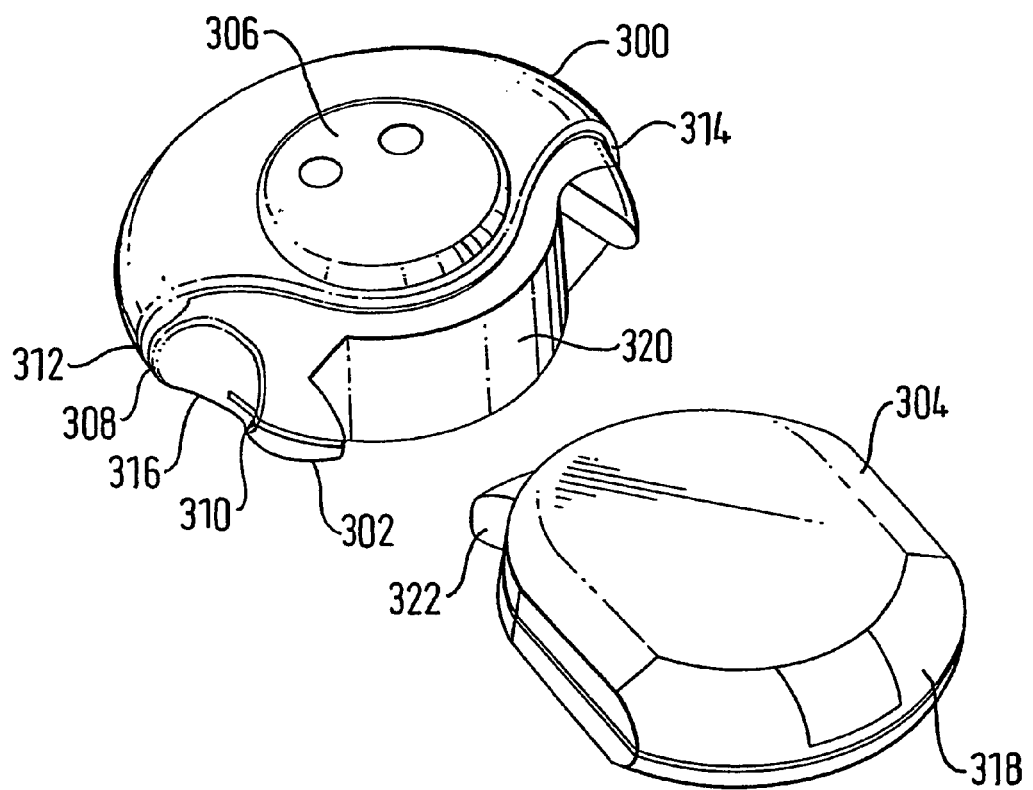
FIG. 3 shows a perspective view of a medicament dispenser, in the form of a holder/body and a refill cassette, according to the invention with the cassette removed from the holder/body.

FIG. 3 shows an external view of a medicament dispenser in accord with the present invention, comprising a body 300, a holder 302, refill cassette 304 and electronic display 306. The holder 302 is shaped to fit snugly inside body 300 and is fixed to a point on the body (not shown) about which it rotates. Stops 308, 310 protrude from the holder 302 and prevent the holder 302 from rotating more than about 180° relative to the body 300. The stops 308, 310 also provide two defined positions of the holder 302 within the body 300. One position is defined by stop 308 meeting with body edge 312 and the other position defined by stop 310 meeting with body edge 314 when the holder has been rotated relative to the body. The area between stops 308 and 310 is shaped to form a thumb or finger grip 316 for the user of the device. The holder 302 forms a shell into which the refill cassette 304 snugly fits.

The refill cassette 304 comprises a shell containing plural medicament carriers stacked one on top of the other (not visible) and a mechanism for opening each of the carriers (not visible) for the medicament to be accessed. The refill cassette 304 has a raised portion 318 at one end on both sides along its width so that this part of the refill cassette 304 is at least the same depth as the part of the holder 320 which receives the refill cassette 304. This allows the position of the cassette 304 within the holder 302 to be fixed such that the ridge 318 protrudes from the holder 302 but the rest of the cassette 304 is contained within the holder 302.

The refill cassette 304 also has a mouthpiece (not visible) and an actuating push button 322 for actuating a mechanism for indexing the medicament carriers held within the cassette 304.

FIGS. 4a to 4e illustrate a medicament dispenser according to another aspect of the present invention. The dispenser comprises a body 400 in the form of a cassette holder which receives a cassette 402. The cassette has a mouthpiece 404 that is covered by a rotating lid 406 when the cassette 402 is received by the body 400.

Figure 4A:
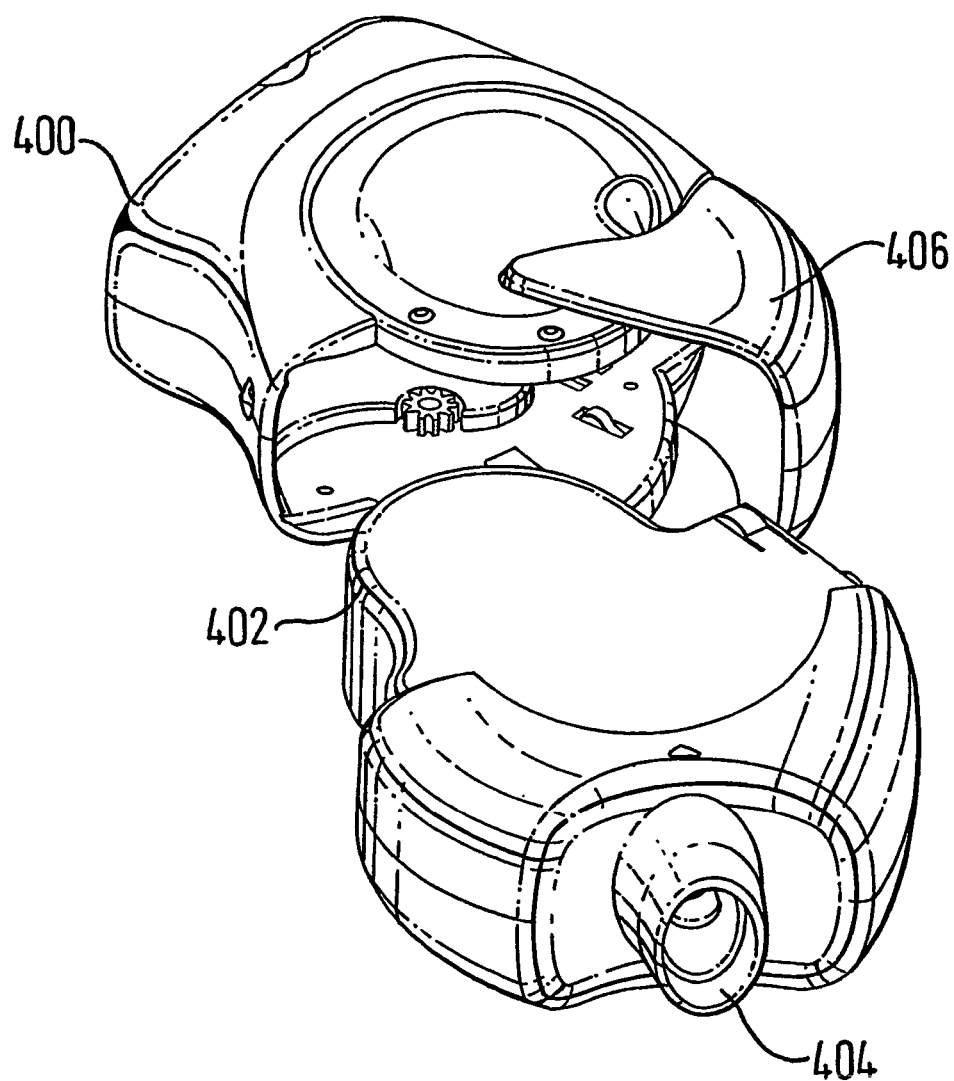
FIG. 4a shows a perspective view of a medicament dispenser, in the form of a holder/body and a refill cassette, according to the invention with the cassette removed from the holder/body.
Figure 4C:
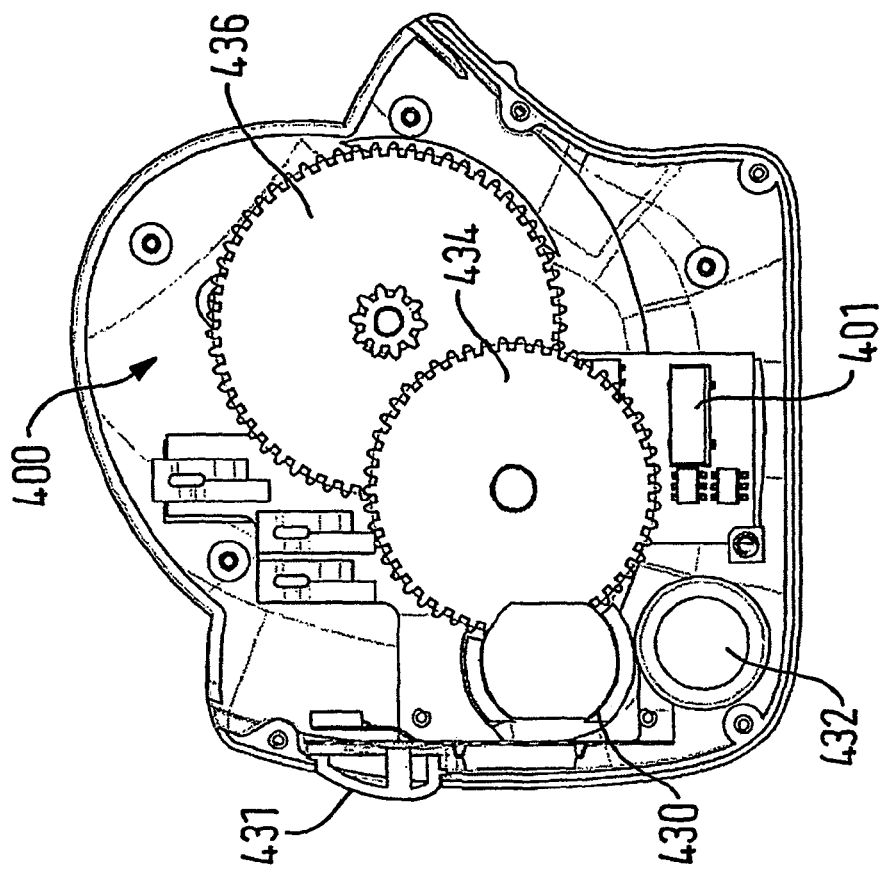
Figure 4B:
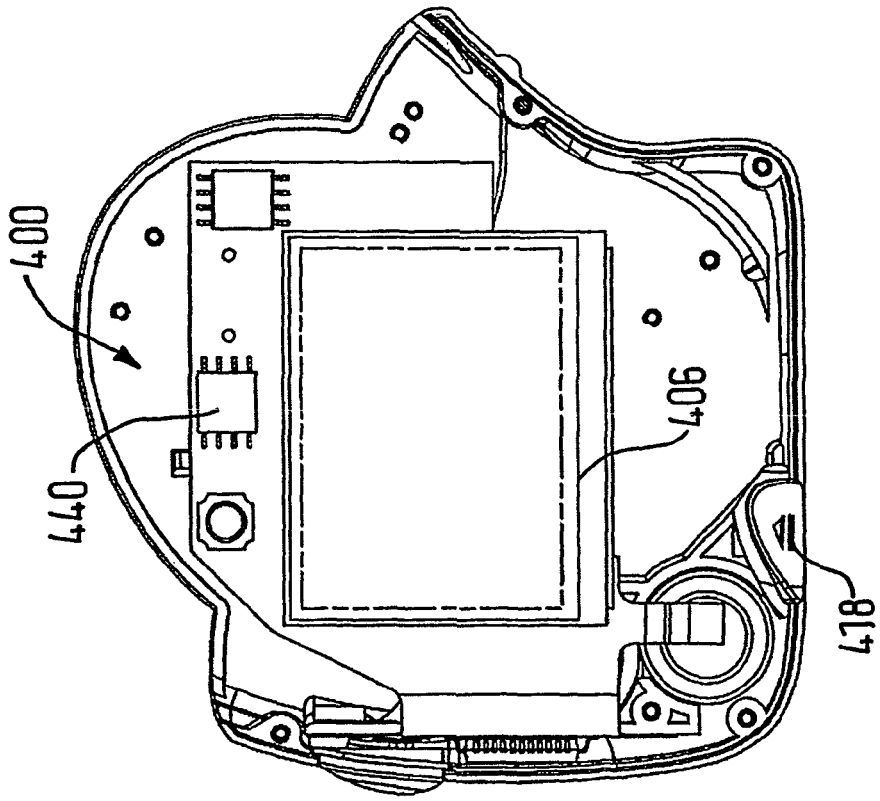

FIGS. 4b and 4c show a split-shell view of the holder 400 body shell. The body 400 is provided with DC motor 430 powered by battery 432, responsive to actuator switch 431. In use, the motor 430 drives gear wheels 434, 436, wherein gear wheel 436 drives foil spool 416 of the cassette 402 to advance medicament dose portions. The body 400 is also provided with cassette release button 418 that releases a reversible catch mechanism (not shown) to enable mechanical release of a cassette 402 from the holder body 400. Circuitry 440, 441 controls the DC motor 430 and is responsive to the actuator switch 431. There is also provided an LCD screen 406 for display of information to the user.

FIGS. 4d and 4e show the cassette 402 in more detail. In use, plural medicament strips (not shown for clarity) are positioned one on top of each other in chamber 403 of the cassette unit 402. Each strip is pre-fed through a guide member 404 within the manifold component and engaged in a multi-pocket index wheel 406. The first pocket of each strip is positioned one pocket away from the opening station 408. The lid foil and base foil of each strip are separable about a beak 410. The resulting empty base foil is coiled about a base take-up spindle 412 in the base take-up chamber 414. The used lid foil is fed over the beak 410 and coiled about a lid take-up spindle 416 in the lid take-up chamber 418.

The dispenser of FIGS. 4a to 4e is actuated by pressing the actuator button 431 on the side of the dispenser which is linked to circuitry 440 which controls DC motor 430 to index the internal mechanism by one pocket of medicament. The DC motor 430 thus indexes each strip and coils up the waste foils.

Initially, the gearing between the index wheel 406 and the lid take-up foil spindle 416 is one-to-one. However, as the lid take up spindle 416 winds on more foil, its effective winding diameter increases. An increase in diameter would cause the lid take-up spindle 416 to pull more strip than the index wheel 406 releases. Thus, in this particular example, compensation is provided for the increase in lid spool 416 diameter by adjusting the amount the lid spool 416 rotates over time.

Figure 5:
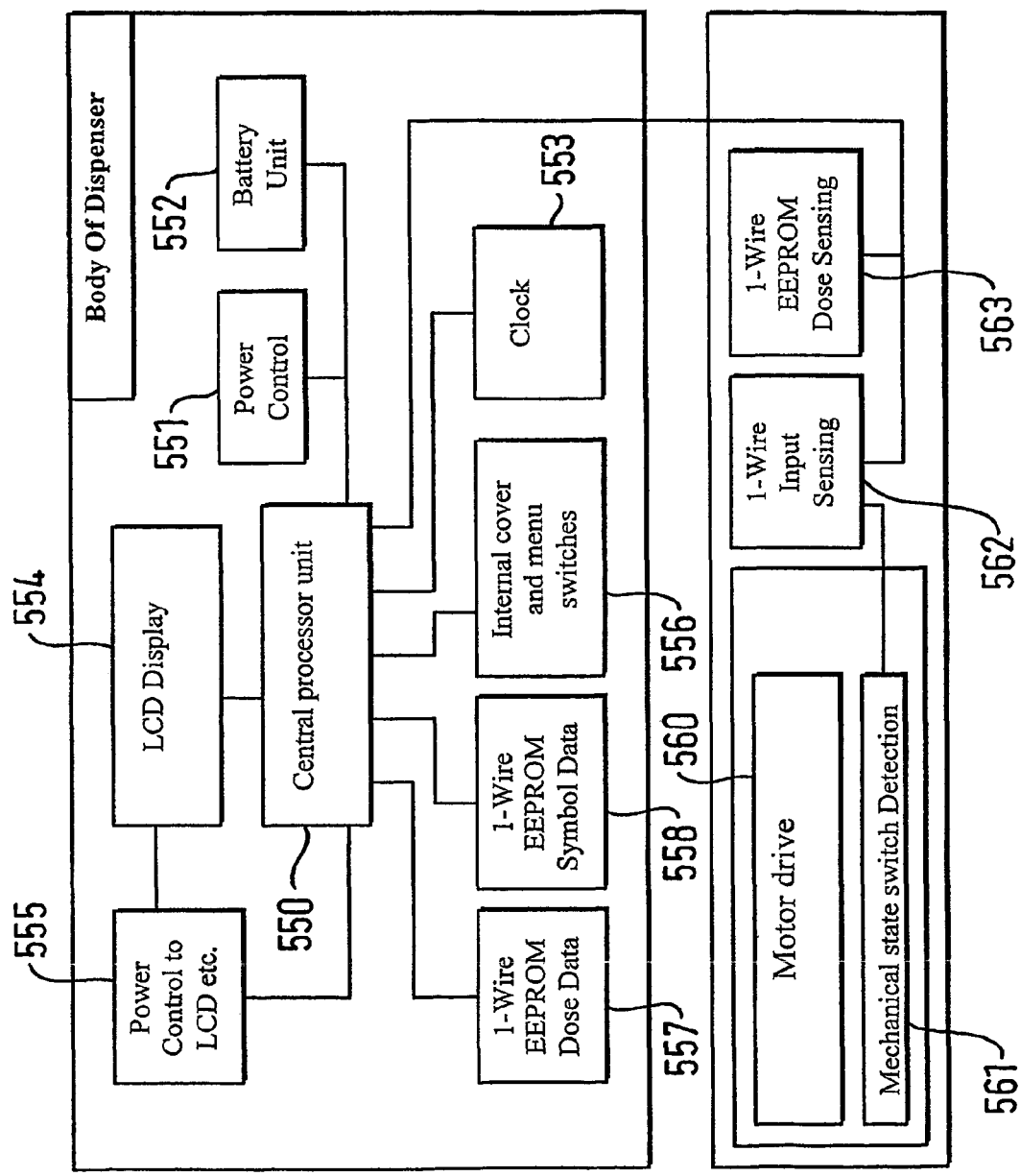
FIG. 5 shows a block diagram of an electronic drive system suitable for use in medicament dispensers herein.

FIG. 5 shows a schematic view of an electronic system suitable for use in a medicament dispenser herein. The electronic components of the system are typically located in the body/holder of a refillable medicament dispenser (e.g. as shown in FIGS. 4a to 4e). Central processor unit (CPU) 550 communicates with power control 551; battery 552; and clock 553. The CPU 550 also communicates with various user input/output functions which in combination comprise a man machine interface (MMI). In more detail, the MMI comprises an LCD display 554; power control for the LCD 555; and menu/switch inputs 556. Various memories including EEPROM dose data memory 557 and EEPROM symbol data memory 558 also communicate with the CPU 550.

The system 550 also communicates with the motor drive 560 and switch actuator 561 therefor. Sensors are provided to detect user input 562 (e.g. manual actuation of the dispenser) and release of dose 563 from the dispenser. In embodiments, the dispenser is provided with a power management system enabling various power saving modes such as 'sleep' and 'powered down' modes.

Figure 6B:
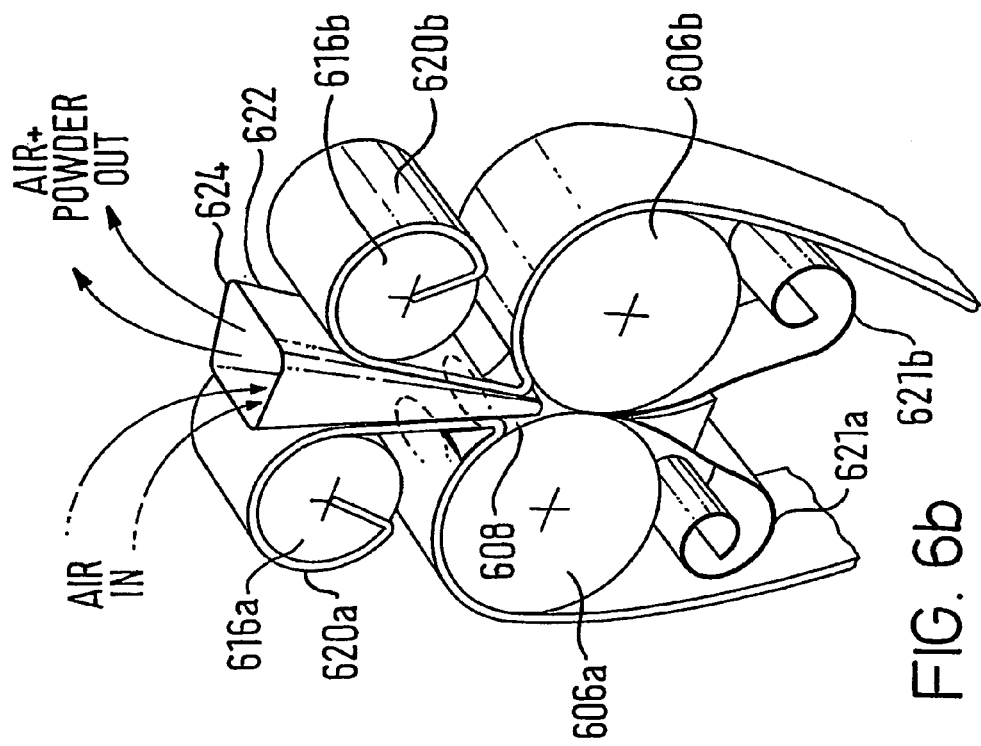
Figure 6A:
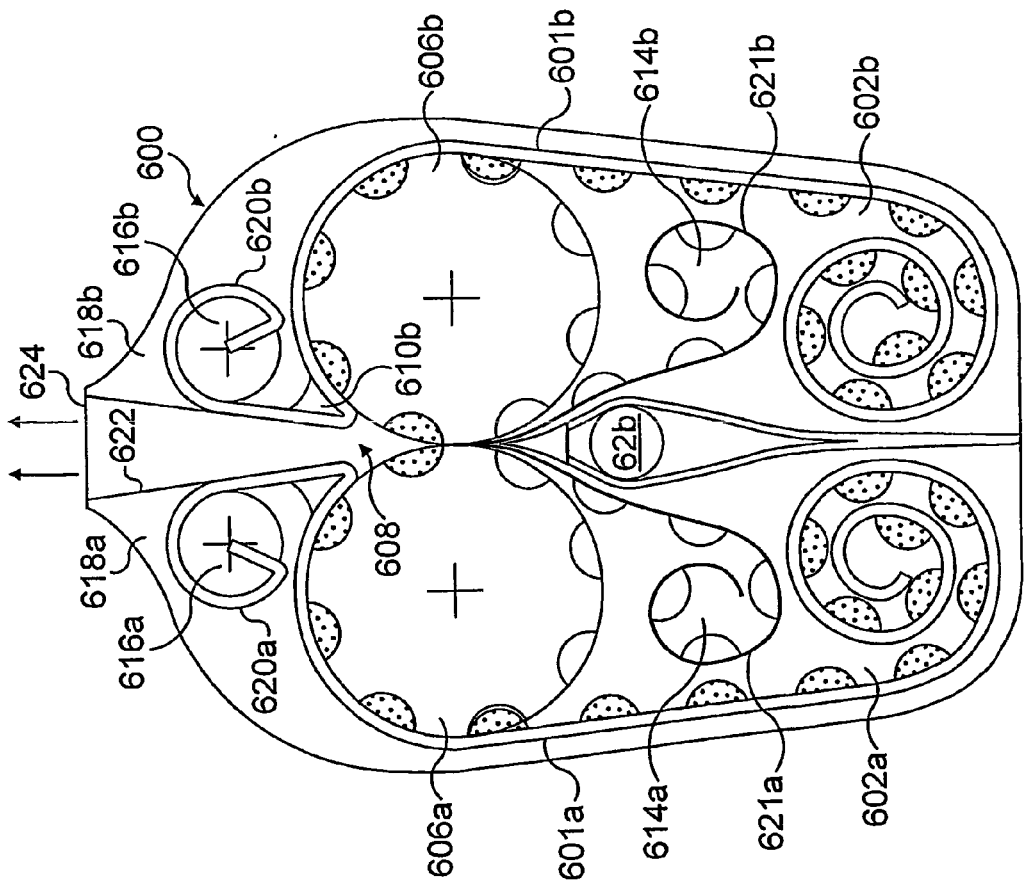
FIG. 6a shows a sectional plan view of a further medicament dispenser in accord with the invention.

FIG. 6a illustrates the base unit 600 of a medicament dispenser according to the invention. In use, a cover (not shown) would be provided to the base unit 600. First and second medicament-containing blister strips 601a, 601b are positioned within respective left and right chambers 602a, 602b of the base unit 600. Each blister strip 601a, 601b engages a respective multi-pocket index wheel 606a, 606b, and successive pockets are thereby guided towards a commonly located opening station 608. The rotation of the index wheels 606a, 606b is coupled. At the opening station 608, the lid foil 620a, 620b and base foil 621a, 621b parts of each strip 601a, 601b are peelably separable about a beak 610a, 610b. The resulting empty base foil 621a, 621b coils up in respective base take-up chambers 614a, 614b. The used lid foil 620a, 620b is fed over its respective beak 610a, 610b and coiled about a lid take-up spindle 616a, 616b in the lid take-up chamber 618a, 618b.

Released powder form medicament from both the first 601a and second 601b strips is channelled via common manifold 622 to a single outlet 624 for inhalation by the patient. Importantly, the dispenser thereby enables different medicament types to be stored separately in each of the strips 601a, 601b but the release and delivery thereof to the patient as a combined inhaled product.

FIG. 6b shows the release of medicament in more detail. The patient breathes in through the outlet 624 resulting in negative pressure being transmitted through manifold 622 to the opened pockets of the strips 601a, 601b at the opening station 608. This results in the creation of a venturi effect which results in the powder contained within each of the opened pockets 601a, 601b being drawn out through the common manifold 622 to the outlet 624 and hence to the patient. Mixing of each separately delivered component of the combined medicament product will thus happens during the delivery process, particularly as a result of the so created venturi effect.

The dispenser is actuated by pressing a button on the side of the dispenser (not shown) which actuates a DC motor 626 to index the internal mechanism by one pocket of medicament for each blister strip 601a, 601b. The DC motor 626, thus results in indexing of each strip 601a, 601b and coiling up of the waste foils.

An advantage of the present invention is that it allows for 'tailored' combination products to be delivered by means of 'mixing and matching' different carrier forms. Particular examples are shown in FIGS. 7 and 8, in which for clarity the carriers are shown in isolation from their associated medicament dispenser.

In FIG. 7, two elongate form blister strips 700a, 700b are arranged in 'double-decker' configuration. Each has multiple distinct blister pockets 704a/b, 706a/b, 708a/b provided in series arrangement there along. For each strip 700a, 700b, the pitch A, B defining the separation between each pocket 704a/b, 706a/b, 708a/b is constant along its length. Also, the pitch A for the first strip 700a, 700b is equal to the pitch B of the second strip. The pocket size of the pockets 704a, 706a, 708a of the first strip 700a is however, smaller in volume than that of the pockets 704b, 706b, 708b of the second strip. It may be appreciated that in use, this arrangement is suitable for the combined delivery of two medicaments, each of which requires different dosing levels but the same dose interval (e.g. both taken once a day).

In FIG. 8, two elongate form blister strips 800a, 800b are arranged in 'double-decker' configuration. Each has multiple distinct blister pockets 804a/b, 806a/b, 808a/b provided in series arrangement there along. For each strip 800a, 800b, the pitch A, B defining the separation between each pocket 804a/b, 806a/b, 808a/b is constant along its length. The pocket size of the pockets 804a, 806a, 808a of the first strip 800a is equivalent to that of the pockets 804b, 806b, 808b of the second strip. However, the pitch A of the first carrier 800a is double that of the pitch B of the second carrier 800b. It may be appreciated that in use, this arrangement is suitable for the combined delivery of two medicaments, each of which requires equivalent dosing levels but wherein the dose interval of the medicament contained in the first strip 800a (e.g. taken once a day). is double that of the dose interval of the medicament contained in the second strip 800b (e.g. taken twice a day). It may also be appreciated that when so arranged the dosing regime corresponds essentially to alternate doses of medicament from the first strip 800a (only) followed by a combination dose from both first 800a and 800b second strips.

In an alternative embodiment, the 'once a day/twice a day' coupled dosing regime provided by the arrangement of FIG. 8 could also be provided using two strips of equivalent pitch, but wherein the medicament dispenser is provided with a 'slip mechanism' such that the first strip only advances (i.e. pocket opens) every other actuation, whereas the second strip is advanced by each actuating action.

Figure 9:
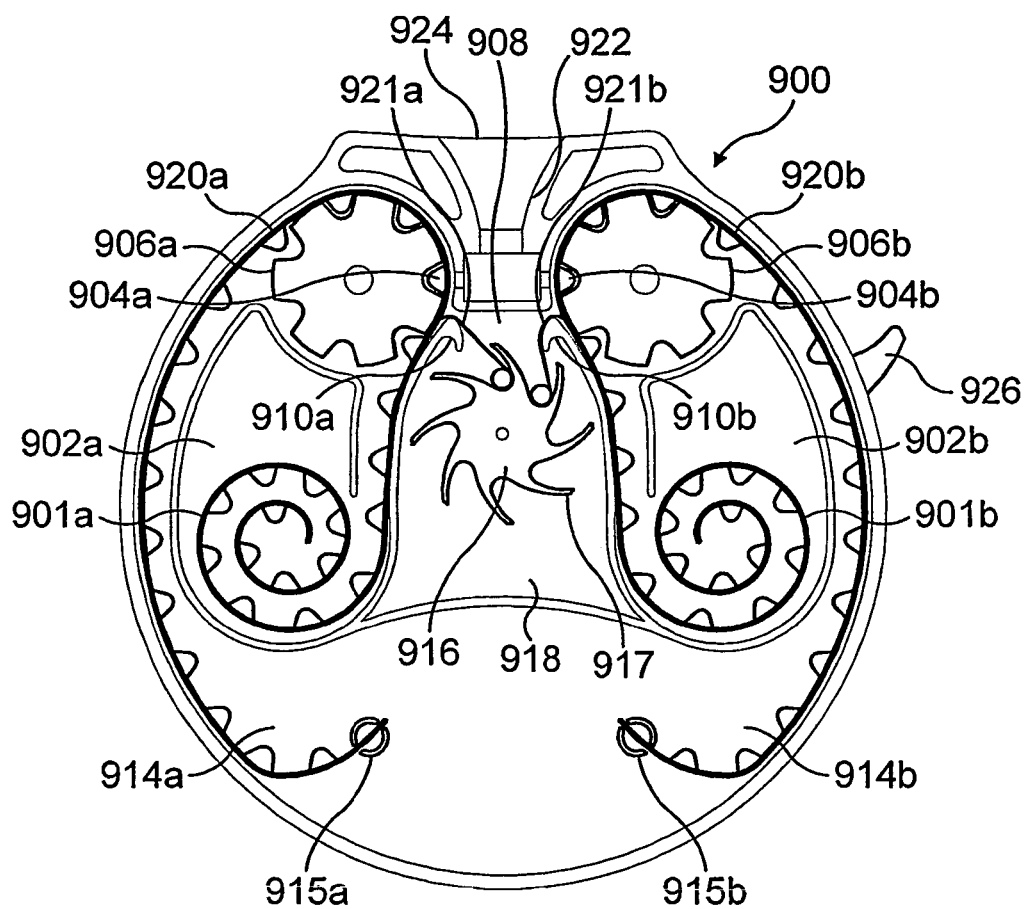
FIGS. 9 to 11 show sectional plan views of further medicament dispensers in accord with the invention.

FIG. 9 illustrates a sectional view of base unit 900 of a medicament dispenser according to the invention. In use, a protective cover (not shown) would be provided to the base unit 900. First and second medicament-containing blister strips 901a, 901b are positioned within respective left and right chambers 902a, 902b of the base unit 900. Each blister strip 901a, 901b engages in respective multi-pocket index wheel 906a, 906b, and successive pockets are thereby guided towards a central opening station 908. The rotation of the index wheels 906a, 906b is optionally coupled together. At the opening station 908, the lid foil 920a, 920b and base foil 921a, 921b parts of each strip 901a, 901b are peelably separable about beak 910a, 910b. The resulting empty base foil 921a, 921b coils up in respective base take-up chambers 914a, 914b. A base foil anchor 915a, 915b anchors the end of each respective base foil 921a, 921b in its chamber 914a, 914b. The used lid foil 920a, 920b feeds over its respective beak 910a, 910b and coils about common lid take-up spindle 916 in the common lid take-up chamber 918.

It will be noted that common lid take-up spindle 916 comprises plural arms 917 that splay out radially from the centre to give it an overall 'collapsible wheel' form. In use, as lid-foil 920a, 920b wraps around the spindle 916, the arms 917 collapse inwardly hereby reducing the diameter of the spindle 916 itself but acting to maintain a roughly constant effective winding diameter as defined by the diameter of the spindle 916 in combination with the used lid foil 920a, 920b wrapped there around. The maintenance of this constant effective winding diameter ensures uniform indexing of each strip 901a, 901b over the entire strip length.

In use, the dispenser is primed by actuating lever 926 located on the side of the dispenser to drivably actuate the lid-take up spindle 916 to advance each blister strip 901a, 901b, thereby causing the leading pocket 904a, 904b thereof to be peeled open. To access the contents of the opened pockets 904a, 904b, the patient then breathes in through the outlet 924. This results in negative pressure being transmitted through manifold 922 to the opened leading pocket 904a, 904b of each strip 901a, 901b at the opening station 908. This in turn, results in the medicament powder contained within each of the opened pockets 904a, 904b being drawn out through the common manifold 922 to the outlet 924 and hence to the patient as an inhaled combination medicament dose. It be appreciated that, mixing of each separately delivered component of the combined medicament product happens as the powder is transported from each opened pocket 904a, 904b to the outlet 924.

Importantly, the dispenser of FIG. 9 enables different medicament types to be stored separately in each of the strips 901a, 901b but allows for the release and delivery thereof to the patient via the single outlet 924 as a combined inhaled product.

Figure 10:
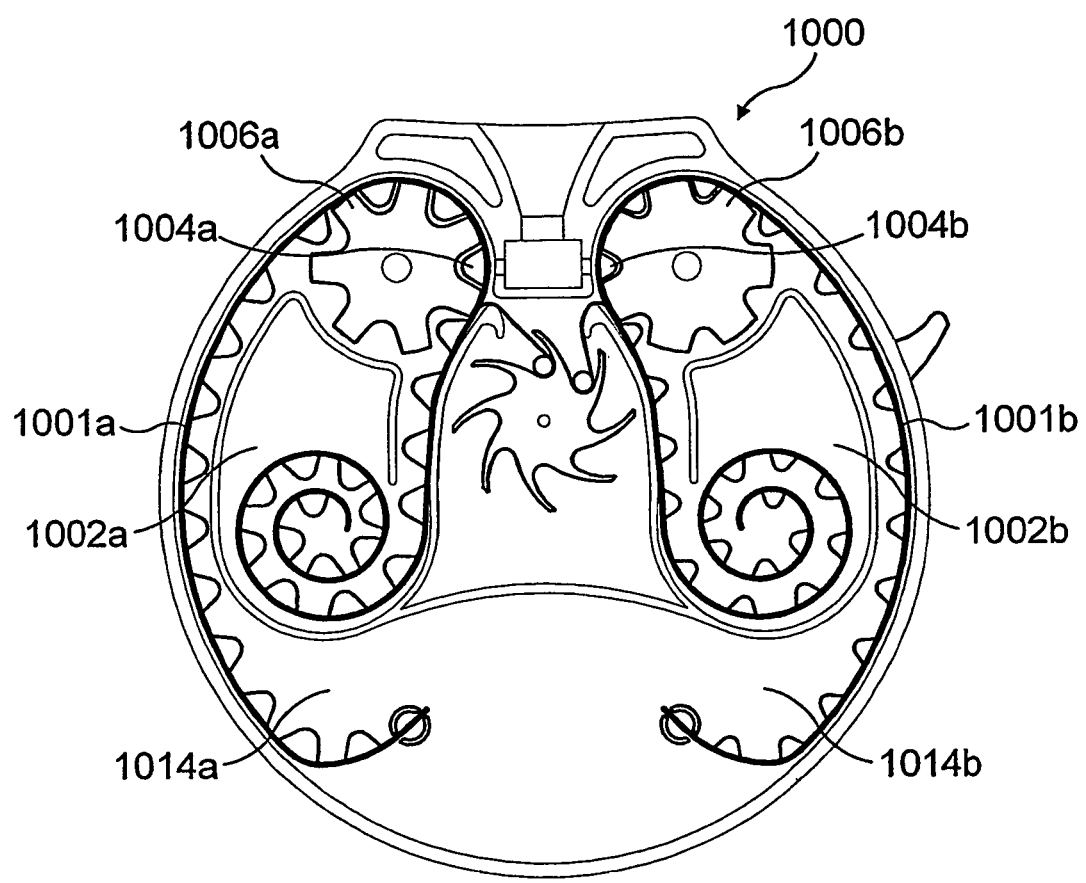

FIG. 10 shows a dispenser comprising a base unit 1000 whose mechanism (not described in detail) is identical in principle, to that of FIG. 9. In a variation of the dispenser of FIG. 9 however, the dispenser is charged with non-identical strip form medicament carriers 1001a, 1001b. The first strip 1001a has larger pockets 1004a than that of those pockets 1004b of the second strip 1001b. As in the strip arrangement of FIG. 7 however, the pocket spacing (i.e. pitch) of the two strips is equal. Since the pocket size of each strip 1001a, 1001b is non-equivalent, the form and shape of the respective index wheels 1006a, 1006b is different. In particular, the first index wheel 1006a is sized and shaped to accommodate the larger pockets of the first strip 1001a.

Whilst in the embodiment illustrated in FIG. 10, the respective strip feed chambers 1002a, 1002b and empty base-foil receiving chambers 1014a, 1014b are of equivalent size and shape, variations may be envisaged in which the sizing and shaping of each respective chamber is arranged to be non-equivalent (e.g. arranged to reflect the size/volume of the relevant non-equivalent strips 1001a, 1001b).

Figure 11:
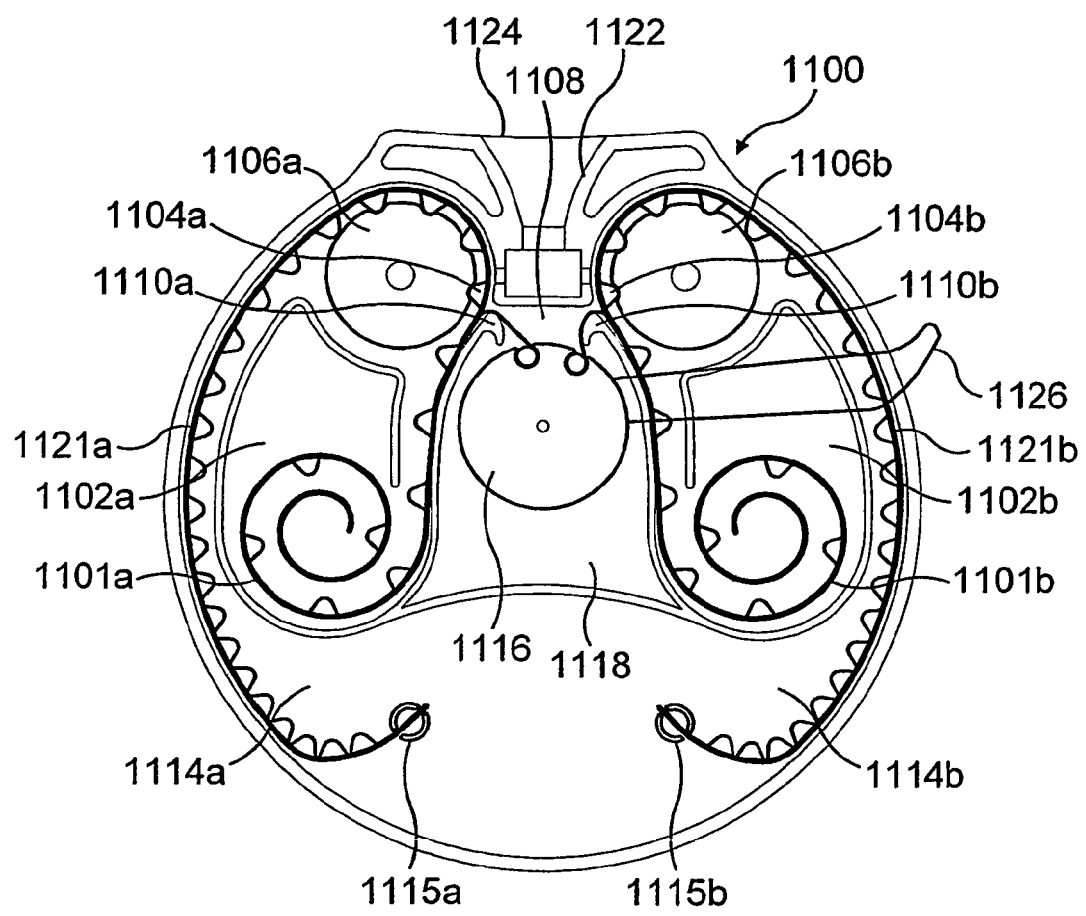

FIG. 11 illustrates a sectional view of base unit 1100 of a medicament dispenser according to the invention. In use, a protective cover (not shown) would be provided to the base unit 1100. First and second medicament-containing blister strips 1101a, 1101b are positioned within respective left and right chambers 1102a, 1102b of the base unit 1100. Each blister strip 1101a, 1101b engages in respective multi-pocket index wheel 1106a, 1106b, and successive pockets are thereby guided towards a central opening station 1108. The rotation of the index wheels 1106a, 1106b may be coupled together. At the opening station 1108, the lid foil 1120a, 1120b and base foil 1121a, 1121b parts of each strip 1101a, 1101b are peelably separable about beak 1110a, 1110b. The resulting empty base foil 1121a, 1121b coils up in respective base take-up chambers 1114a, 1114b. A base foil anchor 1115a, 1115b anchors the end of each respective base foil 1121a, 1121b in its chamber 1114a, 1114b. The used lid foil

1120*a*, 1120*b* feeds over its respective beak 1110*a*, 1110*b* and coils about a common lid take-up spindle 1116 in the common lid take-up chamber 1118.

It will be noted that in the dispenser of FIG. 11, common lid take-up spindle 1116 has a non-collapsible form (c.f. for example, the dispenser of FIG. 9 which has a 'collapsible wheel' spindle 916 form). In use, as lid-foil 1120*a*, 1120*b* wraps around the spindle 1116 its effective winding diameter (as defined by the spindle 1116 and used lid foil 1120*a*, 1120*b* wrapped therearound) will therefore increase. To ensure uniform indexing of each pocket 1104*a*, 1104*b* of each strip 1101*a*, 1101*b*, the spacing (i.e. pitch) between pockets of each strip 1101, 1101*b* of FIG. 11 may be seen to vary over its length. For the first-indexed pockets, the pocket spacing is relatively close. However, to compensate for the increase in effective winding diameter of the spindle 1116 as strip 1001*a*, 1101*b* becomes wrapped therearound the pocket spacing gradually increases over the strip length. Indeed, the pocket spacing for the last-indexed pockets is noted to be markedly greater than for those first-indexed.

In use, the dispenser is primed by actuating lever 1126 located on the side of the dispenser to drivably actuate the non-collapsible lid-take up spindle 1116 to advance each blister strip 1101*a*, 1101*b*, thereby causing the leading pocket 1104*a*, 1104*b* thereof to be peeled open. To access the contents of the opened pockets 1104*a*, 1104*b*, the patient then breathes in through the outlet 1124. This results in negative pressure being transmitted through manifold 1122 to the opened leading pocket 1104*a*, 1104*b* of each strip 1101*a*, 1101*b* at the opening station 1108. This in turn, results in the medicament powder contained within each of the opened pockets 1104*a*, 1104*b* being drawn out through the common manifold 1122 to the outlet 1124 and hence to the patient as an inhaled combination medicament dose. It be appreciated that, mixing of each separately delivered component of the combined medicament product happens naturally as the powder is transported from each opened pocket 1104*a*, 1104*b* to the outlet 1124.

Figure 12A:
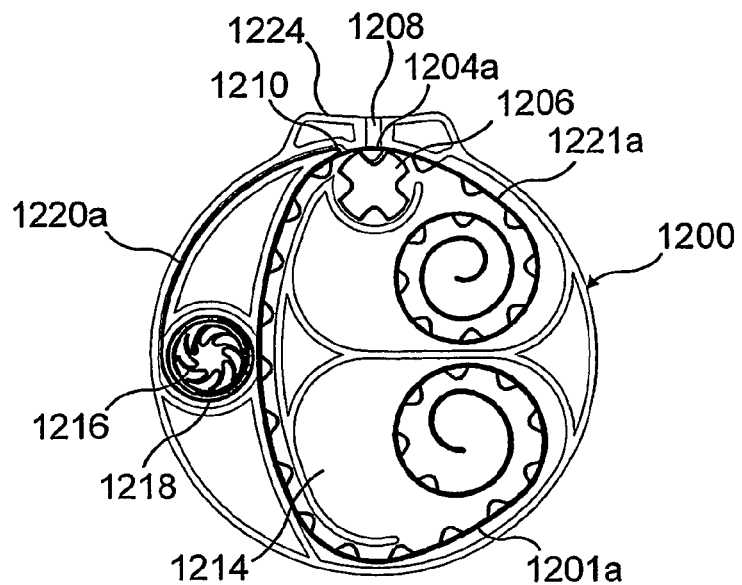
FIG. 12a shows a sectional plan view of a further medicament dispenser in accord with the invention.
Figure 12B:
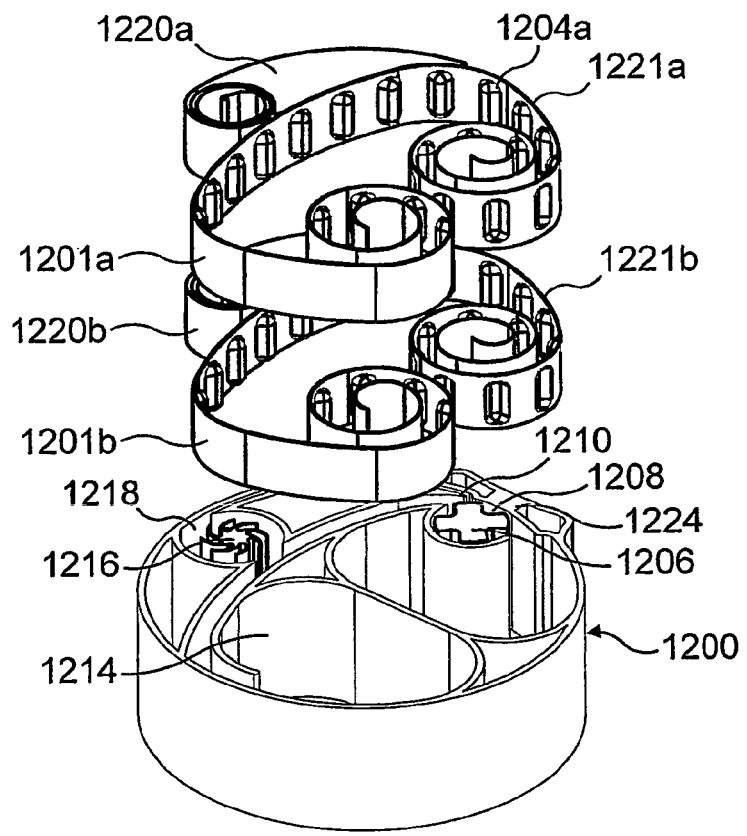
FIG. 12b shows a blown apart, perspective view of the medicament dispenser of FIG. 12a in which two medicament carrier strips associated therewith are shown removed from the dispenser.

FIGS. 12*a* and 12*b* respectively illustrate sectional and perspective views of base unit 1200 of a medicament dispenser according to the invention. In use, a protective cover (not shown) would be provided to the base unit 1200. First and second medicament-containing blister strips 1201*a*, 1201*b* are positioned one on top of the other (in 'double-decker' configuration) in the base unit 1200. In this configuration, each blister strip 1201*a*, 1201*b* shares the same internal mechanism elements (e.g. drive, index, opening) of the base unit 1200. Thus, each strip 1201*a*, 1201*b* engages shared multi-pocket index wheel 1206 and successive pockets are thereby guided towards a central opening station 1208. At the opening station 1208, the lid foil 1220*a*, 1220*b* and base foil 1221*a*, 1221*b* parts of each strip 1201*a*, 1201*b* are peelably separable about beak 1210. The resulting empty base foil 1221*a*, 1221*b* coils up in base take-up chamber 1214. The used lid foil 1220*a*, 1220*b* feeds over beak 1210 and coils about common 'collapsible wheel' form lid take-up spindle 1216 in the common lid take-up chamber 1218.

In use, the dispenser is primed by drivably actuating the lid-take up spindle 1216 to advance each blister strip 1201*a*, 1201*b*, thereby causing the leading pocket 1204*a* (leading pocket not visible on second strip) thereof to be peeled open. To access the contents of the opened pocket 1204*a* the patient then breathes in through the outlet 1224. This results in negative pressure being transmitted to the opened leading pockets 1204*a* at the opening station 1208. This in turn, results in the medicament powder contained within the opened pocket 1204*a* of each strip 1201*a*, 1201*b* being drawn out to the outlet 1224 and hence to the patient as an inhaled combination medicament dose.

Figure 13A:
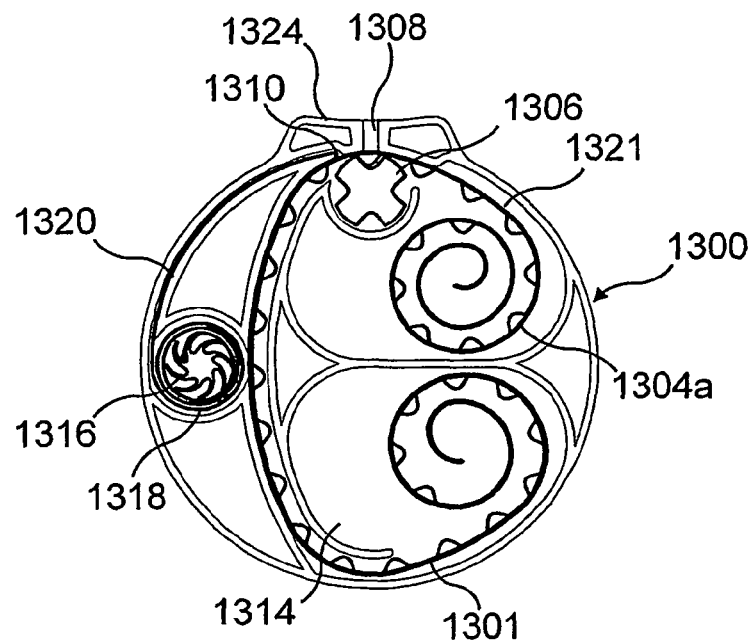
FIG. 13a shows a sectional plan view of a further medicament dispenser in accord with the invention.
Figure 13B:
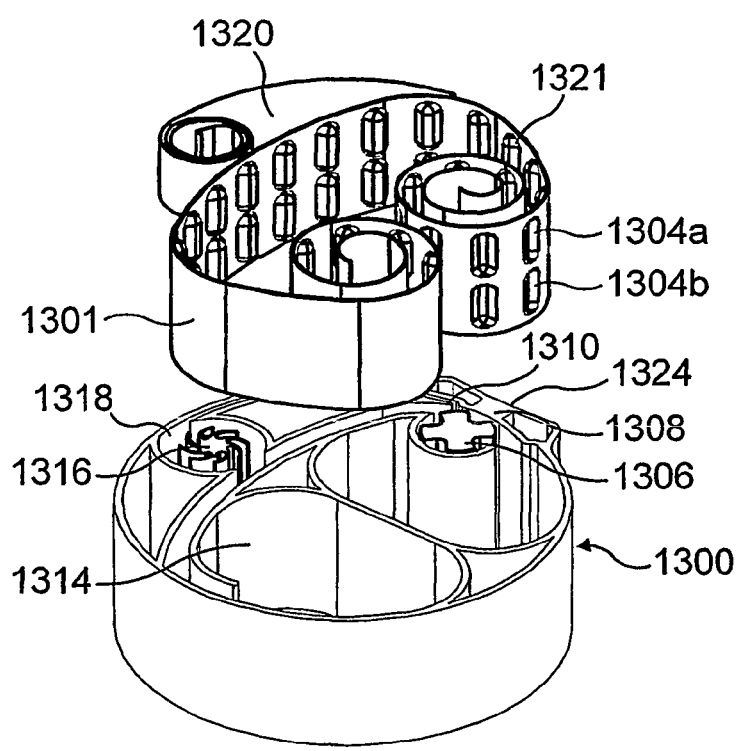
FIG. 13b shows a blown apart, perspective view of the medicament dispenser of FIG. 13a in which the strip form, dual series medicament carrier associated herewith is shown removed from the dispenser.

FIGS. 13*a* and 13*b* respectively illustrate sectional and perspective views of base unit 1300 of a medicament dispenser that may be appreciated to be a variation of the dispenser of FIG. 12. In the dispenser of FIG. 13, the 'double decker' configuration of separate strips 1201*a*, 1201*b* of FIG. 12 is replaced by a single strip 1301 comprising dual series of pockets 1304*a*, 1304*b* arranged in parallel fashion thereon for receipt by the base unit 1300.

As with the dispenser of FIG. 12, each series of blister pockets 1304*a*, 1304*b* shares the same internal mechanism elements (e.g. drive, index, opening) of the base unit 1300. Thus, the dual series strip 1301 engages multi-pocket index wheel 1306 and successive pockets of both series are thereby guided towards a central opening station 1308. At the opening station 1308, the lid foil 1320 and base foil 1321 parts of the dual series strip 1301 are peelably separable about beak 1310. The resulting empty base foil 1321 coils up in base foil take-up chamber 1314. The used lid foil 1320 feeds over beak 1310 and coils about common 'collapsible wheel' form lid take-up spindle 1316 in the common lid take-up chamber 1318.

In use, the dispenser is primed by drivably actuating the lid-take up spindle 1316 to advance the dual series blister strip 1301 thereby causing the leading pockets 1304*a*, 1304*b* of each series thereof to be peeled open. To access the contents of the opened pockets 1304*a*, 1304*b* the patient then breathes in through the outlet 1324. This results in negative pressure being transmitted to the opened leading pockets 1304*a*, 1304*b* at the opening station 1308. This in turn, results in the medicament powder contained within each of the opened pockets 1304*a*, 1304*b* being drawn out to the outlet 1324 and hence to the patient as an inhaled combination medicament dose.

As shown in FIG. 13, the pockets of each series are of equivalent size and shape. It will be appreciated, that in variations, the pockets of one series may be shaped and/or sized differently from that of another series. In other variations, further series of pockets may be employed (e.g. triple parallel series and/or quadruple parallel series of pockets).

Figure 14:
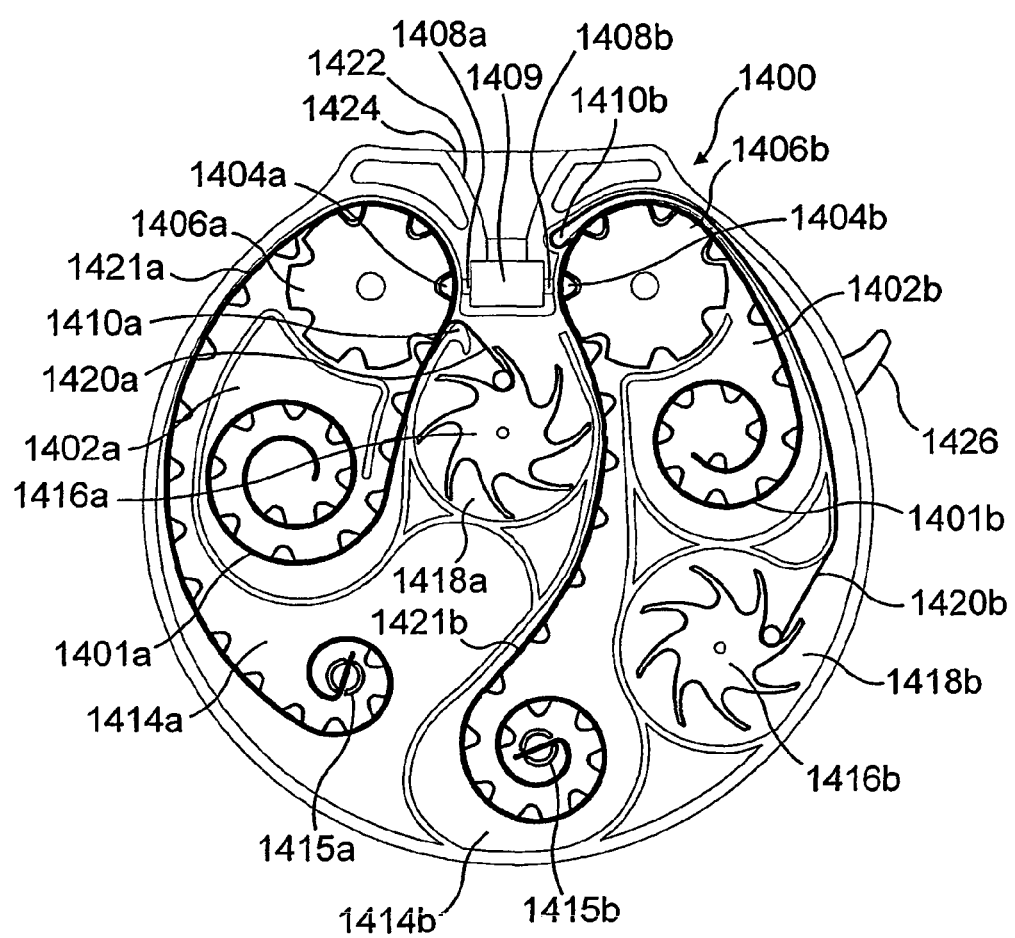
FIG. 14 shows a sectional plan view of a further medicament dispenser in accord with the invention.

FIG. 14 illustrates a sectional view of base unit 1400 of a medicament dispenser according to the invention. In use, a protective cover (not shown) would be provided to the base unit 1400. First and second medicament-containing blister strips 1401*a*, 1401*b* are positioned within respective left and right chambers 1402*a*, 1402*b* of the base unit 1400. Each blister strip 1401*a*, 1401*b* engages in respective multi-pocket index wheel 1406*a*, 1406*b*, and successive pockets are thereby guided towards respective opening stations 1408*a*, 1408*b*, each of which communicate with central powder dispensing chamber 1409. It will be noted that the respective index wheels 1406*a*, 1406*b* are rotated counter to each other to achieve the desired indexing. That is to say, the first index wheel 1406*a* is rotated anti-clockwise, whereas the second index wheel 1406*b* is rotated clockwise.

At the respective opening stations 1408*a*, 1408*b*, the lid foil 1420*a*, 1420*b* and base foil 1421*a*, 1421*b* parts of each strip 1401*a*, 1401*b* are peelably separable about beak 1410*a*, 1410*b*. The resulting empty base foil 1421*a*, 1421*b* coils up in respective base take-up chambers 1414*a*, 1414*b*. A base foil anchor 1415*a*, 1415*b* anchors the end of each respective base foil 1421*a*, 1421*b* in its chamber 1414*a*, 1414*b*. The used lid foil 1420*a*, 1420*b* feeds over its respective beak 1410*a*, 1410*b* and coils about its respective 'collapsible wheel' form lid take-up spindle 1416*a*, 1416*b* in its lid take-up chamber 1418*a*, 1418*b*.

In use, the dispenser is primed by common actuating lever 1426 located on the side of the dispenser to drivably actuate each lid-take up spindle 1416*a*, 1416*b* to advance each blister strip 1401*a*, 1401*b*, thereby causing the leading pocket 1404*a*, 1404*b* thereof to be peeled open. To access the contents of the opened pockets 1404*a*, 1404*b*, the patient then breathes in through the outlet 1424. This results in negative pressure being transmitted through manifold 1422 to the dispensing chamber 1409 and opened leading pocket 1404*a*, 1404*b* of each strip 1401*a*, 1401*b*. This in turn, results in the medicament powder contained within each of the opened pockets 1404*a*, 1404*b* being drawn out through the common manifold 1422 to the outlet 1424 and hence to the patient as an inhaled combination medicament dose. It be appreciated that, mixing of each separately delivered component of the combined medicament product happens as the powder is transported from each opened pocket 1404*a*, 1404*b* to the outlet 1424.

Figure 15A:
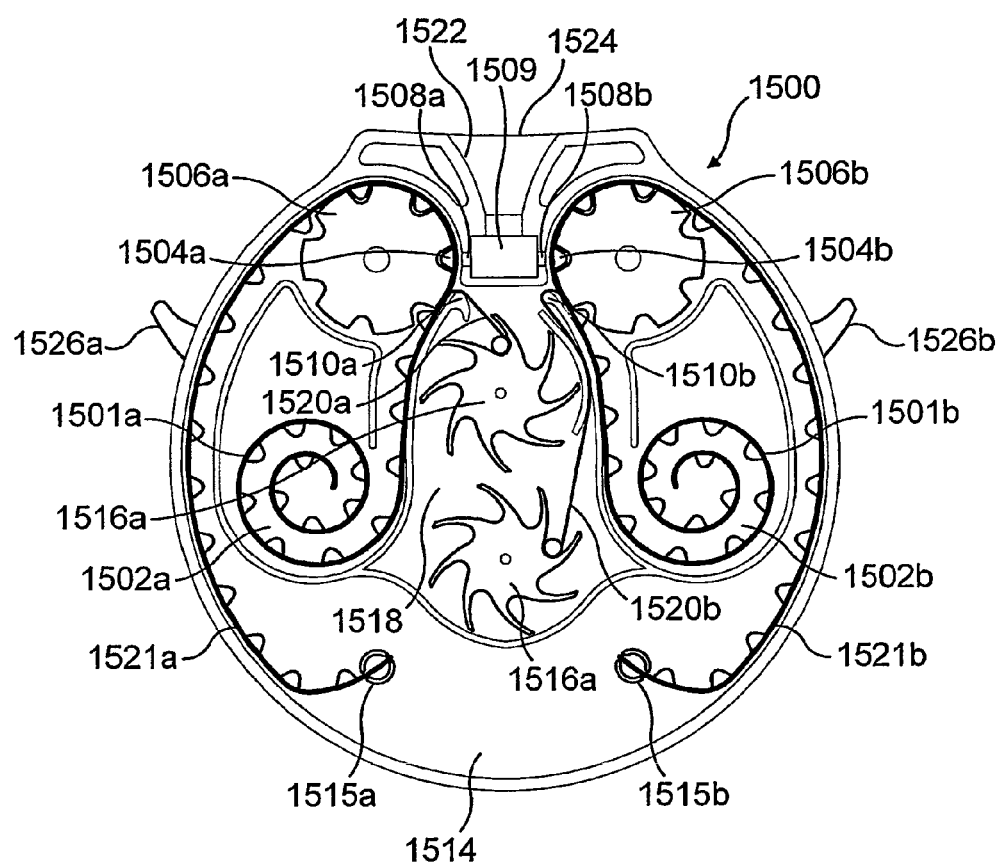
FIGS. 15a and 15b respectively show sectional plan and sectional plan with part cut-away views of a further medicament dispenser in accord with the invention.
Figure 15B:
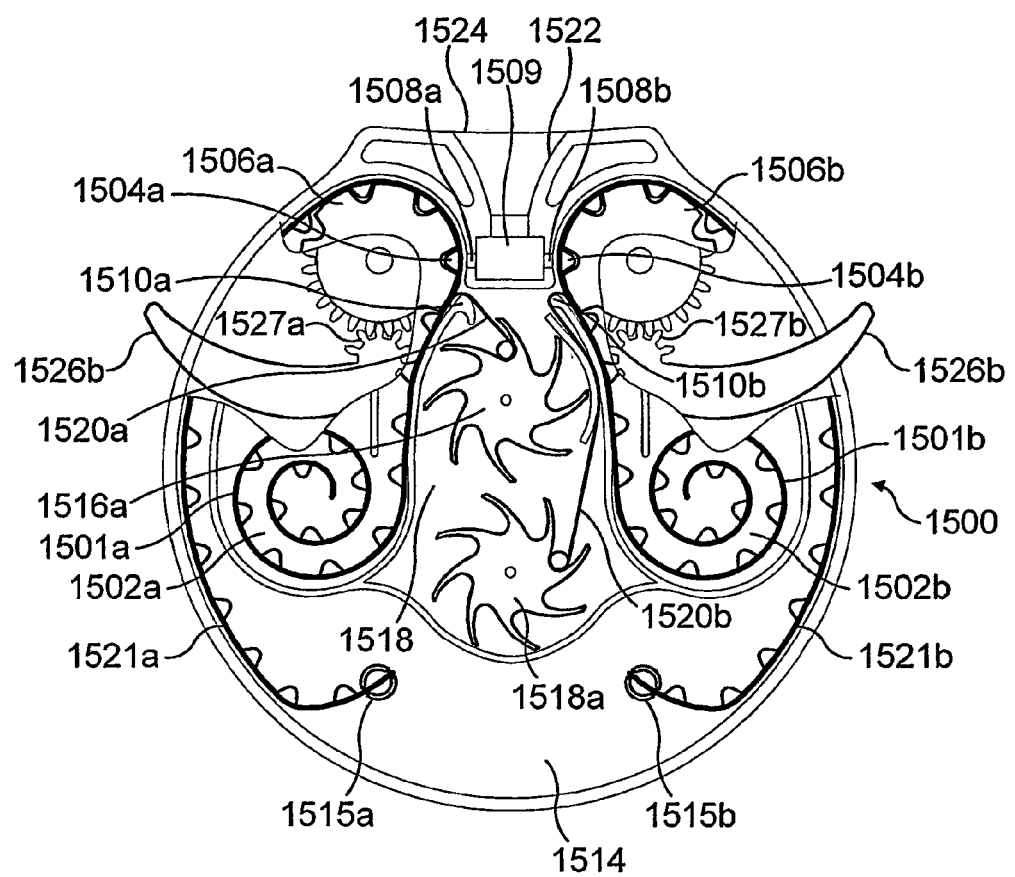

FIGS. 15*a* and 15*b* illustrate sectional and sectional with part cut-away views of base unit 1500 of a medicament dispenser that may be appreciated to be a variation of the dispenser of FIG. 14. What the dispenser of FIGS. 15*a* and 15*b* provides above and beyond the dispenser of FIG. 14 is the capability to separately actuate each lid spindle drive 1516*a*, 1516*b* and hence to separately (and hence, selectively) open a leading pocket 1504*a*, 1504*b* of each strip 1501*a*, 1501*b*. Thus, either single medicament or combined medicament doses are deliverable.

First and second medicament-containing blister strips 1501*a*, 1501*b* are positioned within respective left and right chambers 1502*a*, 1502*b* of the base unit 1500. Each blister strip 1501*a*, 1501*b* engages in respective multi-pocket index wheel 1506*a*, 1506*b*, and successive pockets are thereby guided towards respective opening stations 1508*a*, 1508*b*, each of which communicate with central powder dispensing chamber 1509.

At the respective opening stations 1508*a*, 1508*b*, the lid foil 1520*a*, 1520*b* and base foil 1521*a*, 1521*b* parts of each strip 1501*a*, 1501*b* are peelably separable about beak 1510*a*, 1510*b*. The resulting empty base foil 1521*a*, 1521*b* coils up in shared base take-up chamber 1514. A base foil anchor 1515*a*, 1515*b* anchors the end of each respective base foil 1521*a*, 1521*b* in the chamber 1514. The used lid foil 1520*a*, 1520*b* feeds over its respective beak 1510*a*, 1510*b* and coils about its respective 'collapsible wheel' form lid take-up spindle 1516*a*, 1516*b* in shared lid take-up chamber 1518.

In use, each strip 1501*a*, 1501*b* is separately primable by its own actuating lever 1526*a*, 1526*b* located on either side of the dispenser to drivably actuate each index wheel 1506*a*, 1506*b* to advance each blister strip 1501*a*, 1501*b*, thereby causing the leading pocket 1504*a*, 1504*b* thereof to be peeled open. It will be seen in FIG. 15*b* that each actuating lever 1526*a*, 1526*b* is in separate geared relationship (through interlocking gear teeth 1527*a*, 1527*b*) with each respective index wheel 1506*a*, 1506*b*.

To access the contents of the opened pocket or pockets (depending on whether either one or both strips 1501*a*, 1501*b* has been primed) 1504*a*, 1504*b*, the patient then breathes in through the outlet 1524. This results in negative pressure being transmitted through manifold 1522 to the dispensing chamber 1509 and opened leading pocket(s) 1504*a*, 1504*b*. This in turn, results in the medicament powder contained within the opened pocket(s) 1504*a*, 1504*b* being drawn out through the common manifold 1522 to the outlet 1524 and hence to the patient as an inhaled (combination) medicament dose.

Figure 16A:
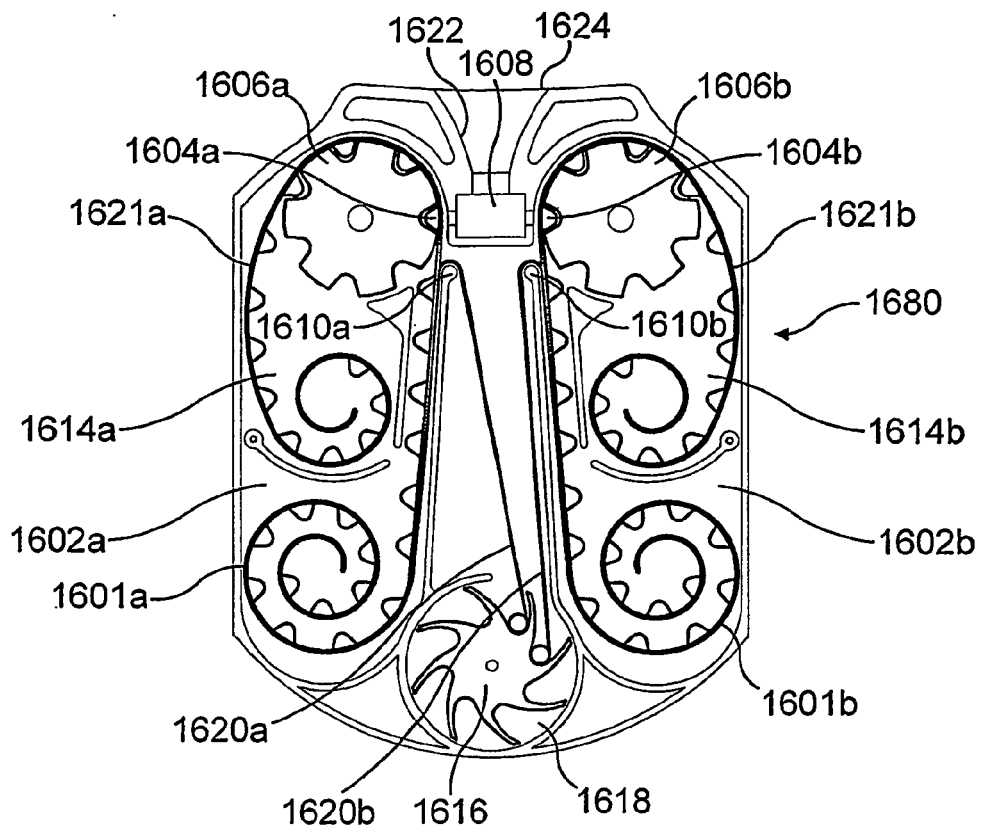
FIG. 16c shows a perspective view of a medicament dispenser, in the form of a holder/body (shown in FIG. 16b) and a refill cassette (shown in FIG. 16a), according to the invention with the cassette received in the holder/body.
Figure 16B:
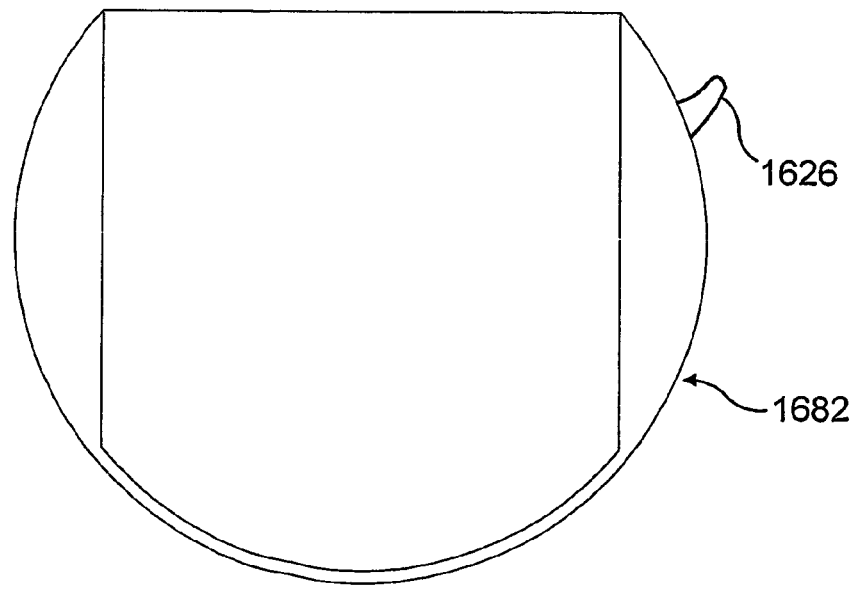
Figure 16C:
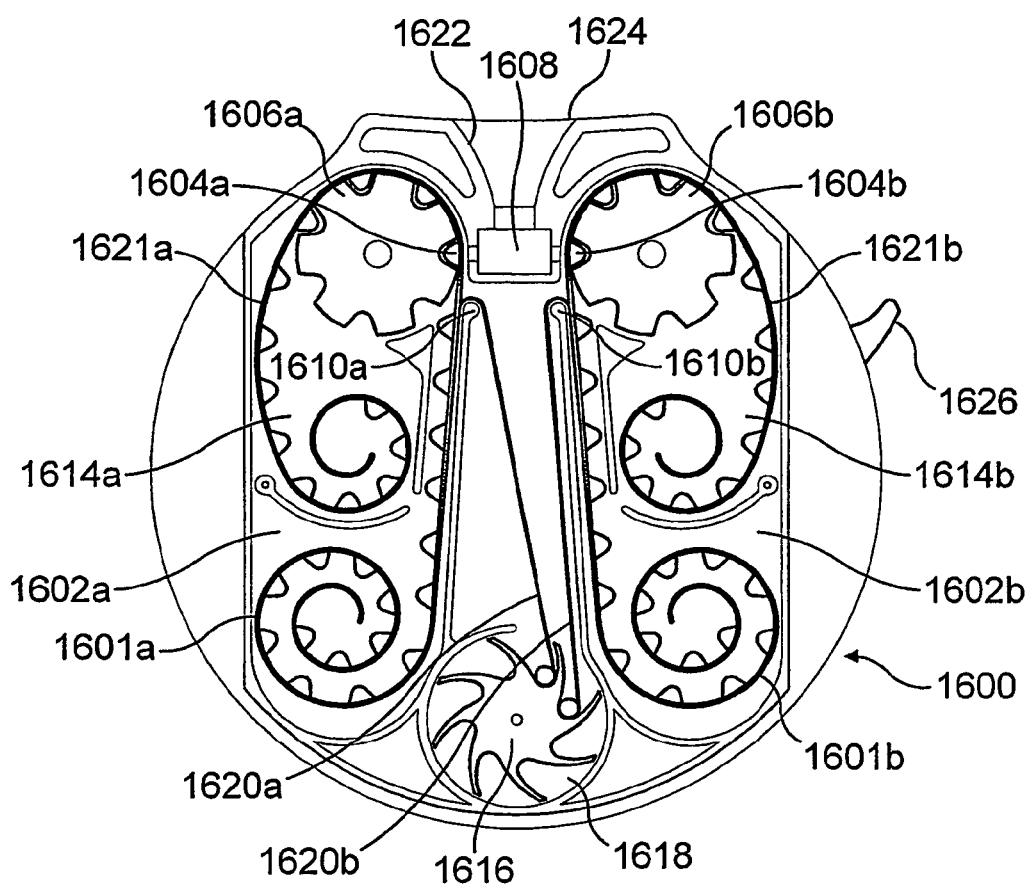

FIG. 16*c* shows a medicament dispenser 1600 in reloadable form. The dispenser separately comprises a holder/body 1682 (shown in FIG. 16*b*) and a refill cassette 1680 (shown in FIG. 16*a*) snugly receivable thereby.

The medicament carrier strip 1601*a*, 1601*b* indexing and access mechanism of the dispenser of FIGS. 16*a* to 16*c* is primarily located in the refill cassette and may be appreciated to be a variation of the mechanism of the dispenser of FIG. 9. In more detail, first and second medicament-containing blister strips 1601*a*, 1601*b* are positioned within respective left and right chambers 1602*a*, 1602*b* of the refill cassette 1680. Each blister strip 1601*a*, 1601*b* engages in respective multi-pocket index wheel 1606*a*, 1606*b*, and successive pockets are thereby guided towards a central opening station 1608. The rotation of the index wheels 1606*a*, 1606*b* is optionally coupled together (e.g. by a coupling rod). At the opening station 1608, the lid foil 1620*a*, 1620*b* and base foil 1621*a*, 1621*b* parts of each strip 1601*a*, 1601*b* are peelably separable about beak 1610*a*, 1610*b*. The resulting empty base foil 1621*a*, 1621*b* coils up in respective base take-up chambers 1614*a*, 1614*b*. The used lid foil 1620*a*, 1620*b* feeds over its respective beak 1610*a*, 1610*b* and coils about common lid take-up spindle 1616 in the common lid take-up chamber 1618. It will be noted that common lid take-up spindle 1616 has the 'collapsible wheel' form as described in more detail for the dispenser of FIG. 9.

In use, the dispenser is primed by actuating lever 1626 located on the side of the holder/body 1682 to drivably actuate the index wheels 1606*a*, 1606*b* to advance each blister strip 1601*a*. 1601*b*, thereby causing the leading pocket 1604*a*, 1604*b* thereof to be peeled open. To access the contents of the opened pockets 1604*a*, 1604*b*, the patient then breathes in through the outlet 1624. This results in negative pressure being transmitted through manifold 1622 to the opened leading pocket 1604*a*, 1604*b* of each strip 1601*a*, 1601*b* at the opening station 1608. This in turn, results in the medicament powder contained within each of the opened pockets 1604*a*, 1604*b* being drawn out through the common manifold 1622 to the outlet 1624 and hence to the patient as an inhaled combination medicament dose. Mixing of each separately delivered component of the combined medicament product happens as the powder is transported from each opened pocket 1604*a*, 1604*b* to the outlet 1624.

The dispenser of FIG. 16 enables different medicament types to be stored separately in each of the strips 1601*a*, 1601*b* of the cassette 1680 but allows for the release and delivery thereof to the patient via the single outlet 1624 as a combined inhaled product.

Figure 17:
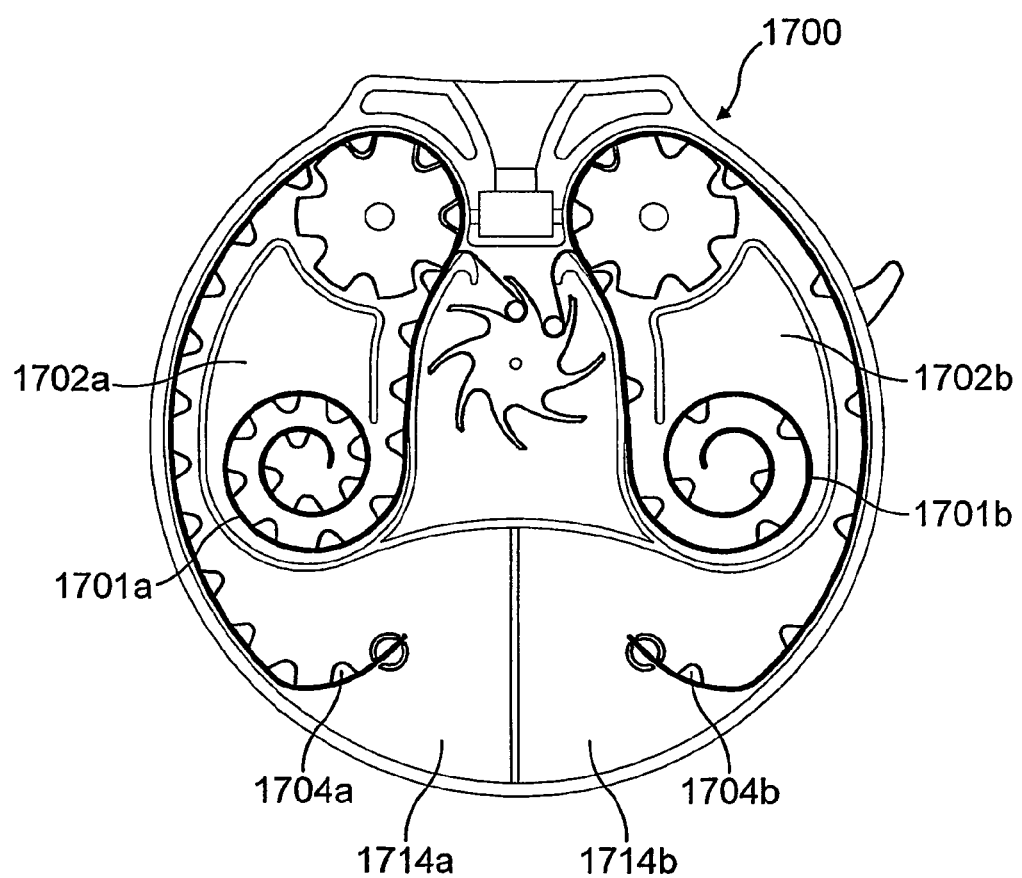
FIGS. 17 to 24 show sectional plan views of further medicament dispensers in accord with the invention.

FIG. 17 shows a dispenser comprising a base unit 1700 whose mechanism (not therefore described in detail) is identical in principle, to that of FIG. 9. In a variation of the dispenser of FIG. 9 however, the dispenser is charged with non-identical strip form medicament carriers 1701*a*, 1701*b*. The second strip 1701*b* has pockets 1704*a* double-spaced (i.e. twice the pitch) of those pockets 1704*a* of the first strip 1001*b*.

The dispenser of FIG. 17 may therefore be appreciated to basically employ the dual strip arrangement of FIG. 8. In use, the dispenser is thus suitable for the combined delivery of two medicaments, each of which requires equivalent dosing levels but wherein the dose interval of the medicament contained in the second strip 1701*b* (e.g. taken once a day) is double that of the dose interval of the medicament contained in the first strip 1701*a* (e.g. taken twice a day). It may also be appreciated that when so arranged the dosing regime corresponds essentially to alternate doses of medicament from the first strip 1701a (only) followed by a combination dose from both first 1701a and 1701b second strips.

Whilst in the embodiment illustrated in FIG. 17, the respective strip feed chambers 1702a, 1702b and empty base-foil receiving chambers 1714a, 1714b are of equivalent size and shape, variations may be envisaged in which the sizing and shaping of each respective chamber is arranged to be non-equivalent (e.g. arranged to reflect the numbers of pockets and hence coiled sizing of the relevant non-equivalent strips 1701a, 1701b).

Figure 18:
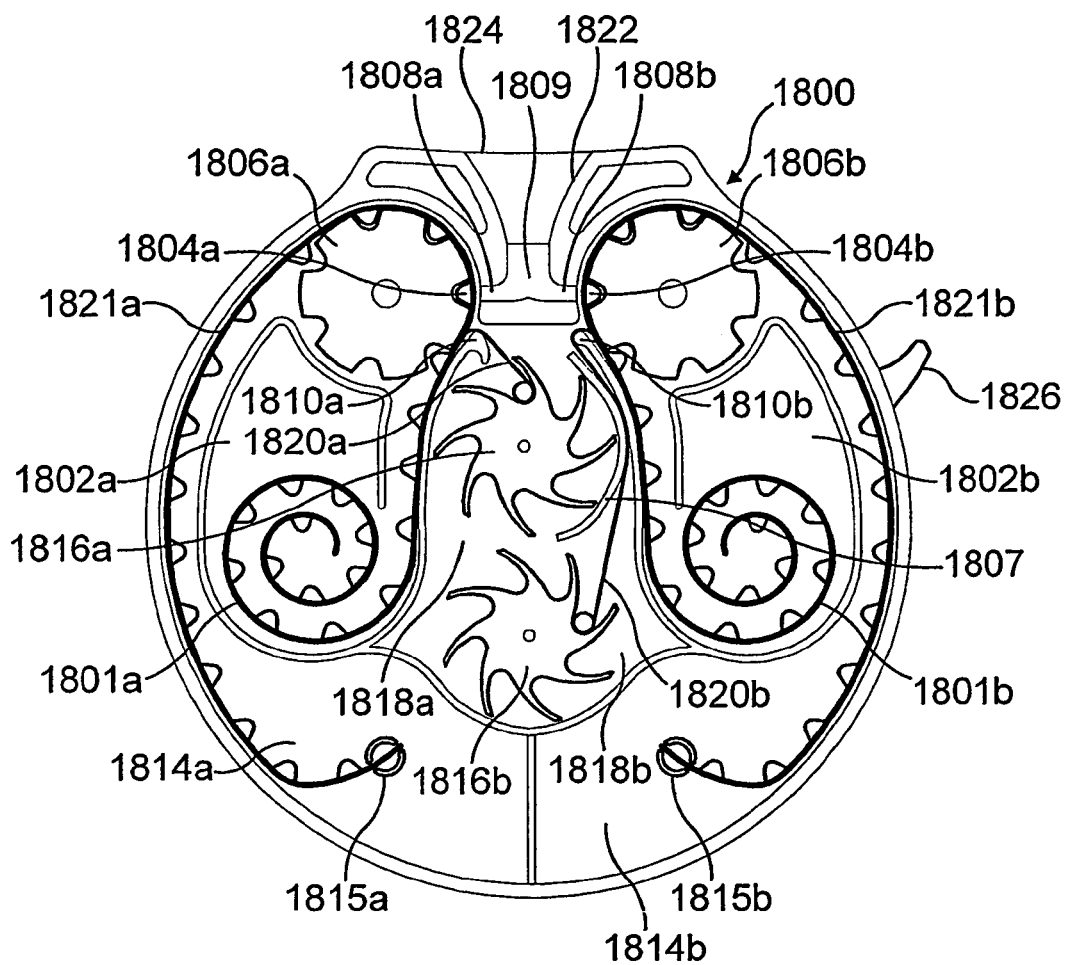

FIG. 18 illustrates a sectional view of base unit 1800 of a medicament dispenser according to the invention. In use, a protective cover (not shown) would be provided to the base unit 1800. First and second medicament-containing blister strips 1801a, 1801b are positioned within respective left and right chambers 1802a, 1802b of the base unit 1800. Each blister strip 1801a, 1801b engages in respective multi-pocket index wheel 1806a, 1806b, and successive pockets are thereby guided towards respective opening stations 1808a, 1808b, each of which communicate with central powder dispensing chamber 1809.

At the respective opening stations 1808a, 1808b, the lid foil 1820a, 1820b and base foil 1821a, 1821b parts of each strip 1801a, 1801b are peelably separable about beak 1810a, 1810b. The resulting empty base foil 1821a, 1821b coils up in respective base take-up chambers 1814a, 1814b. Base foil anchor 1815a, 1815b anchors the end of each respective base foil 1821a, 1821b in its chamber 1814a, 1814b. The used lid foil 1820a, 1820b feeds over its respective beak 1810a, 1810b and coils about its respective 'collapsible wheel' form lid take-up spindle 1816a, 1816b in its lid foil take-up chamber 1818a, 1818b. Guide wall 1807 guides the used lid foil 1820b of the second strip 1801b away from the first lid take-up spindle 1816a and towards its respective take up spindle 1816b and chamber 1818b.

In use, the dispenser is primed by common actuating lever 1826 located on the side of the dispenser to drivably actuate each lid-take up spindle 1816a, 1816b to advance each blister strip 1801a, 1801b, thereby causing the leading pocket 1804a, 1804b thereof to be peeled open. To access the contents of the opened pockets 1804a, 1804b, the patient then breathes in through the outlet 1824. This results in negative pressure being transmitted through manifold 1822 to the dispensing chamber 1809 and opened leading pocket 1804a, 1804b of each strip 1801a, 1801b. This in turn, results in the medicament powder contained within each of the opened pockets 1804a, 1804b being drawn out through the common manifold 1822 to the outlet 1824 and hence to the patient as an inhaled combination medicament dose. It be appreciated that, mixing of each separately delivered component of the combined medicament product happens as the powder is transported from each opened pocket 1804a, 1804b to the outlet 1824.

Figure 19:
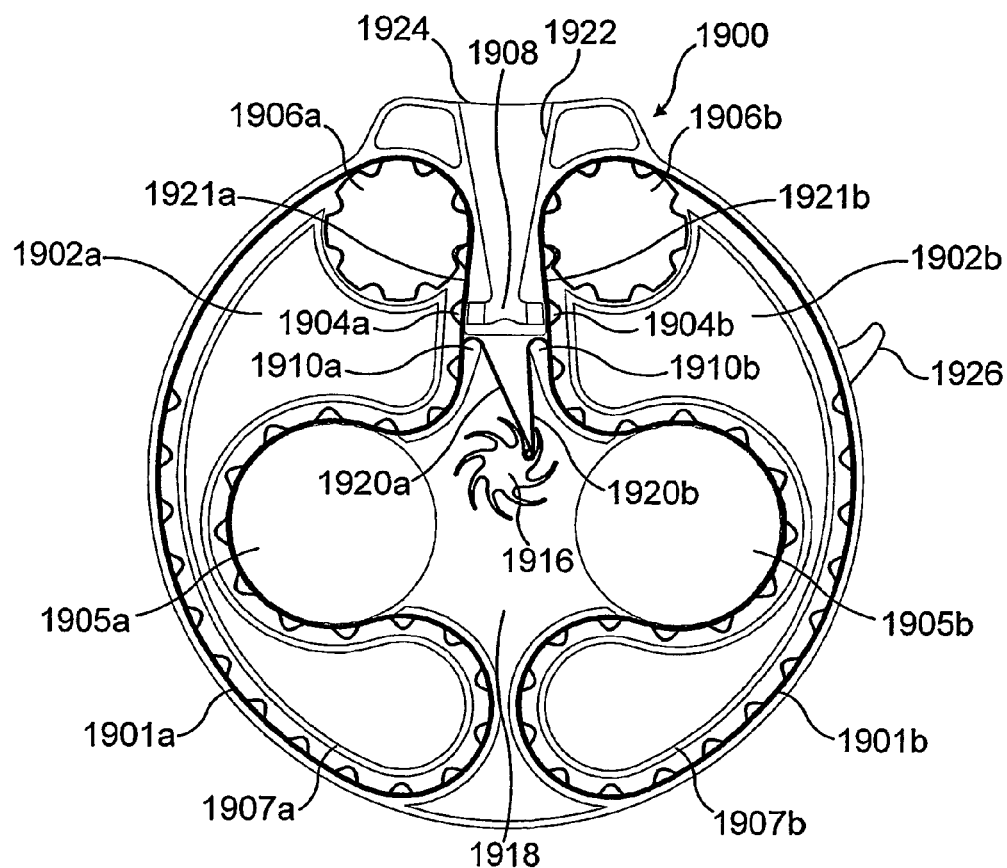

FIG. 19 illustrates a sectional view of base unit 1900 of a medicament dispenser according to the invention. In use, a protective cover (not shown) would be provided to the base unit 1900. First and second medicament-containing blister strips 1901a, 1901b are positioned about left and right lobes 1902a, 1902b of the base unit 1900. Each blister strip 1901a, 1901b has a continuous loop form. That is to say, each strip comprises a continuous loop of base foil 1921a, 1921b having pockets 1904a, 1904b for containing medicament arranged along the majority of its length; and a strip of lid foil 1920a, 1920b provided to the base foil 1921a, 1921b to initially seal at least all of the pockets 1904a, 1904b. Within the dispenser the strip 1901a, 1901b snakes around hub 1905a, 1905b and guiding wall 1907a, 1907b that generally act to define the shape of each loop 1901a, 1901b when housed in the dispenser unit 1900.

Each blister strip 1901a, 1901b engages in respective multi-pocket index wheel 1906a, 1906b, and successive pockets are thereby guided towards a central opening station 1908. The rotation of the index wheels 1906a, 1906b is optionally coupled together. At the opening station 1908, the lid foil 1920a, 1920b and base foil 1921a, 1921b parts of each strip 1901a, 1901b are peelably separable about beak 1910a, 1910b. In contrast to the embodiment of FIG. 9 (for example), the resulting empty base foil 1921a, 1921b is not coiled up. Rather, because it is joined (in 'continuous loop' fashion) to the tail-end of the strip 1901a, 1901b it continues to be transported through the dispenser as the strip 1901a, 1901b is further advanced. The need for any distinct base foil take-up chamber (e.g. see chambers 914a, 914b of FIG. 9) is thereby avoided. More conventionally, the used lid foil 1920a, 1920b feeds over its respective beak 1910a, 1910b and coils about 'collapsible wheel' form common lid take-up spindle 1916 in the common lid take-up chamber 1918.

In use, the dispenser is primed by actuating lever 1926 located on the side of the dispenser to drivably actuate the index wheels 1906a, 1906b to advance each blister strip 1901a, 1901b, thereby causing the leading pocket 1904a, 1904b thereof to be peeled open. To access the contents of the opened pockets 1904a, 1904b, the patient then breathes in through the outlet 1924. This results in negative pressure being transmitted through manifold 1922 to the opened leading pocket 1904a, 1904b of each strip 1901a, 1901b at the opening station 1908. This in turn, results in the medicament powder contained within each of the opened pockets 1904a, 1904b being drawn out through the common manifold 1922 to the outlet 1924 and hence to the patient as an inhaled combination medicament dose. It be appreciated that, mixing of each separately delivered component of the combined medicament product happens as the powder is transported from each opened pocket 1904a, 1904b to the outlet 1924.

Figure 20:
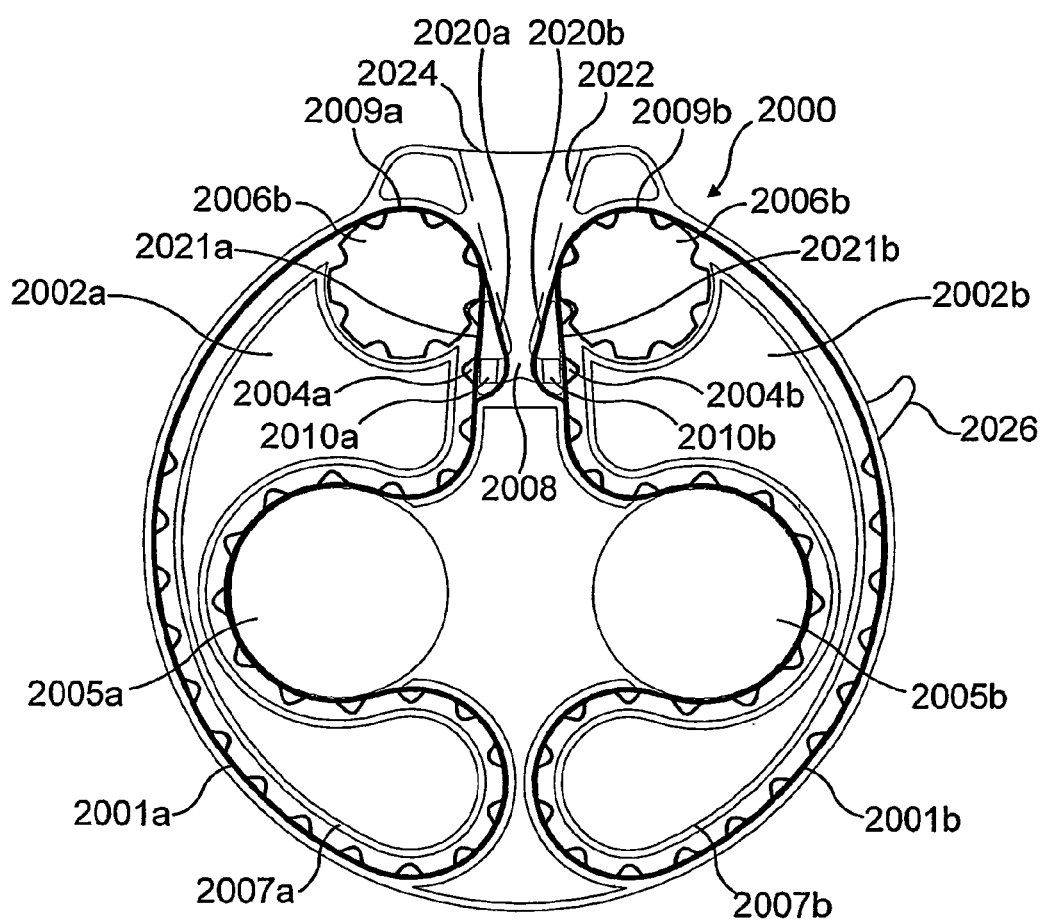

FIG. 20 illustrates a sectional view of base unit 2000 of a medicament dispenser that employs a development of the continuous loop concept of the dispenser of FIG. 19. In particular, each blister strip 2001a, 2001b thereof has a continuous loop form comprising both a continuous loop of base foil 2021a, 2021b having pockets 2004a, 2004b for containing medicament arranged along the majority of its length; and a corresponding continuous loop of lid foil 2020a, 2020b provided to the looped base foil 2021a, 2021b to seal all of the pockets 2004a, 2004b thereof. As will be appreciated from the more detailed description provided below, the means for accessing the medicament contained within the pockets 2004a, 2004b is also subtly different in that opened pockets 2004a, 2004b are generally resealable once medicament has been accessed therefrom.

In use, a protective cover (not shown) would be provided to the base unit 2000 of the dispenser of FIG. 20. First and second continuous loop form medicament-containing blister strips 2001a, 2001b are positioned about left and right lobes 2002a, 2002b of the base unit 2000. Within the dispenser each strip 2001a, 2001b snakes around hub 2005a, 2005b and guiding wall 2007a, 2007b which generally define the shape of each looped carrier 2001a, 2001b when housed in the dispenser unit 2000.

Each blister strip 2001a, 2001b engages in respective multi-pocket index wheel 2006a, 2006b, and successive pockets are thereby guided towards a central opening station 2008. The rotation of the index wheels 2006a, 2006b is generally coupled together by suitable coupling means (not visible). At the opening station 2008, the lid foil 2020a, 2020b and base foil 2021a, 2021b parts of each strip 2001a, 2001b are peelably separable about separation wedge 2010a, 2010b. It will be noted that the wedge 2010a, 2010b locates between the respective lid 2020a, 2020b and base foils 2021a, 2021b to wedge one apart from the other. The resulting empty base foil 2021a, 2021b and lid foil 2020a, 2020b associated therewith are not coiled up. Rather, because both are joined (in 'continuous loop' fashion) to the tail-end of the strip 2001a, 2001b they continue to be transported through the dispenser as the strip 2001a, 2001b is further advanced. As such further advancement draws these component parts of the strip 2001a, 2001b into contact with the respective index wheels 2006a, 2006b the lid foil 2020a, 2020b is pushed back into contact with the empty base foil 2021a, 2021b as it is sandwiched between index wheel 2006a, 2006b and curved wall 2009a, 2009b provided circumferentially thereto. The need for any distinct base foil take-up chamber (e.g. see chambers 914a, 914b of FIG. 9) and lid take-up spindle and take up chamber (e.g. see spindle 916 and chamber 918 of FIG. 9) is thereby avoided.

In use, the dispenser is primed by actuating lever 2026 located on the side of the dispenser to drivably actuate the index wheels 2006a, 2006b to advance each blister strip 2001a, 2001b, thereby causing the leading pocket 2004a, 2004b thereof to be (at least, temporarily) wedged open. To access the contents of the opened pockets 2004a, 2004b, the patient then breathes in through the outlet 2024. This results in negative pressure being transmitted through manifold 2022 to the opened leading pocket 2004a, 2004b of each strip 2001a, 2001b at the opening station 2008. This in turn, results in the medicament powder contained within each of the opened pockets 2004a, 2004b being drawn out through the common manifold 2022 to the outlet 2024 and hence to the patient as an inhaled combination medicament dose. It be appreciated that, mixing of each separately delivered component of the combined medicament product happens as the powder is transported from each opened pocket 2004a, 2004b to the outlet 2024.

As will already be appreciated from earlier described examples, the need to ensure uniform indexing over the entire length of a strip form medicament carrier can necessitate the use of subtle compensating means in the design of suitable strip transport/opening mechanisms. The dispensers of FIGS. 21 and 22 both employ alternative compensating means to the 'collapsible wheel' lid spindle drive of for example, FIG. 9.

Figure 21:
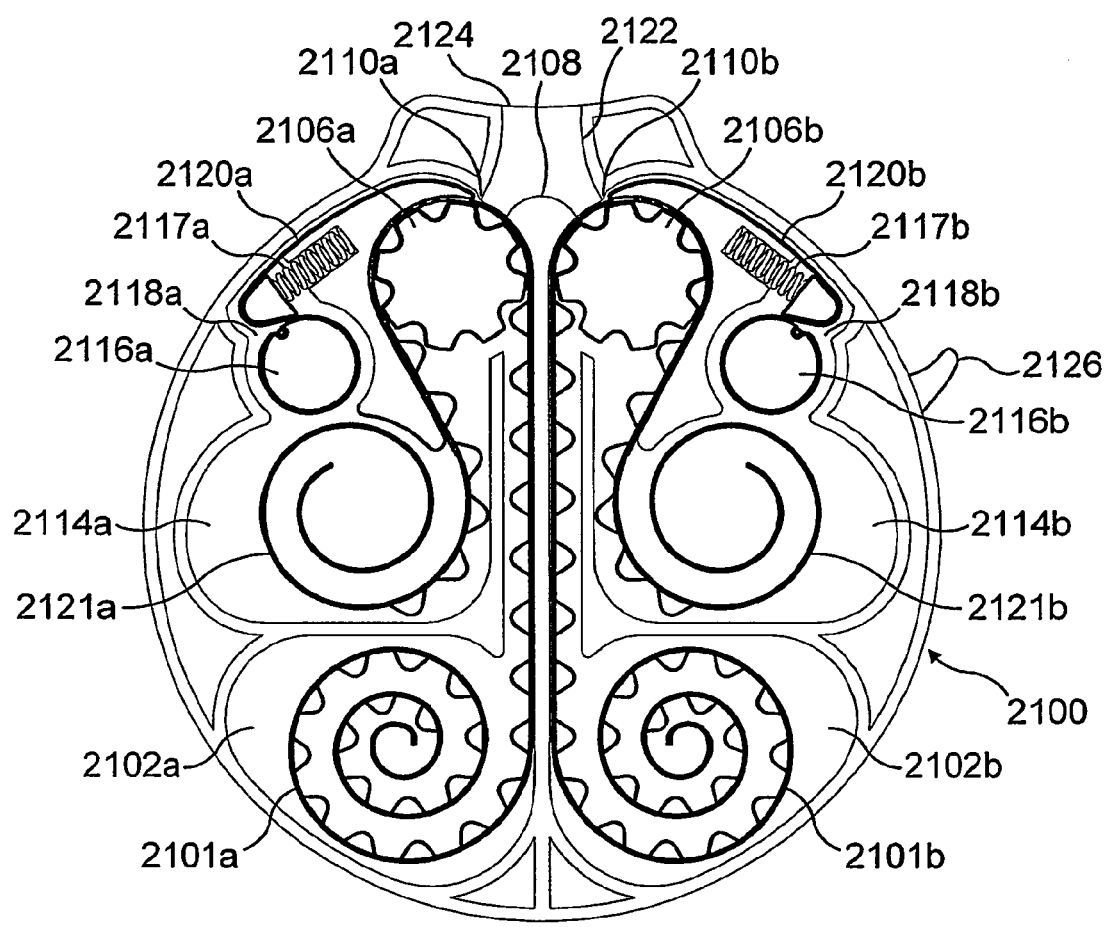

FIG. 21 illustrates a sectional view of base unit 2100 of a medicament dispenser according to the invention. In use, a protective cover (not shown) would be provided to the base unit 2100. First and second medicament-containing blister strips 2101a, 2101b are positioned within respective left and right chambers 2102a, 2102b of the base unit 2100. Each blister strip 2101a, 2101b engages in respective multi-pocket index wheel 2106a, 2106b, and successive pockets are thereby guided towards a central, double-lobed opening station 2108. The rotation of the index wheels 2106a, 2106b is optionally coupled together. At the opening station 2108, the lid foil 2120a, 2120b and base foil 2121a, 2121b parts of each strip 2101a, 2101b are peelably separable about beak 2110a, 2110b. The resulting empty base foil 2121a, 2121b coils up in respective base take-up chambers 2114a, 2114b. The used lid foil 2120a, 2120b feeds over its respective beak 2110a, 2110b and coils about lid take-up spindle 2116a, 2116b in its respective lid take-up chamber 2118a, 2118b.

Located between each respective beak 2110a, 2110b and lid take-up spindle 2116a, 2116b is a spring-loaded tensioner 2117a, 2117b. The function of the tensioner is to ensure a roughly constant driving tension is providable to strip 2101a, 2101b by its lid take-up spindle 2116a, 2116b over the course of an entire strip length. In particular, the tensioner acts to compensate for the variation in drive tension associated with the increase in the effective winding diameter of each spindle 2116a, 2116b as used lid foil 2120a, 2120b gradually becomes wrapped there around. Thus, uniform indexing of each strip 2101a, 2101b may be maintained over the entire strip length.

In use, the dispenser is primed by actuating lever 2126 located on the side of the dispenser to drivably actuate each lid-take up spindle 2116a, 2116b to advance each blister strip 2101a, 2101b, thereby causing the leading pocket 2104a, 2104b thereof to be peeled open. The respective spring-loaded tensioners 2117a, 2117b provide any necessary drive compensation, as described above. To access the contents of the opened pockets 2104a, 2104b, the patient then breathes in through the outlet 2124. This results in negative pressure being transmitted through manifold 2122 to the opened leading pocket 2164a, 2104b of each strip 2101a, 2101b at the opening station 2108. This in turn, results in the medicament powder contained within each of the opened pockets 2104a, 2104b being drawn out through the common manifold 2122 to the outlet 2124 and hence to the patient as an inhaled combination medicament dose. It be appreciated that, mixing of each separately delivered component of the combined medicament product happens as the powder is transported from each opened pocket 2104a, 2104b to the outlet 2124.

Figure 22:
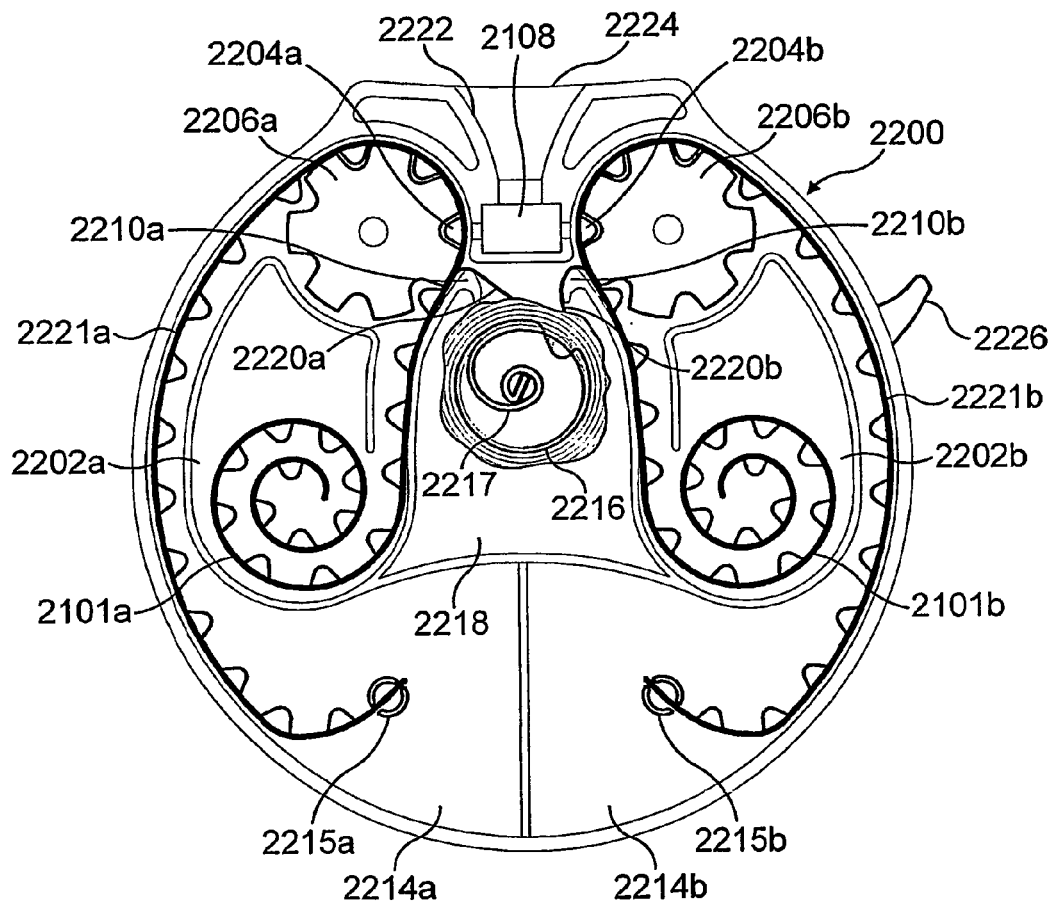

FIG. 22 illustrates a sectional view of base unit 2200 of a medicament dispenser according to the invention. In use, a protective cover (not shown) would be provided to the base unit 2200. First and second medicament-containing blister strips 2201a, 2201b are positioned within respective left and right chambers 2202a, 2202b of the base unit 2200. Each blister strip 2201a, 2201b engages in respective multi-pocket index wheel 2206a, 2206b, and successive pockets are thereby guided towards a central opening station 2208. The rotation of the index wheels 2206a, 2206b is optionally coupled together (e.g. via a suitable gear train). At the opening station 2208, the lid foil 2220a, 2220b and base foil 2221a, 2221b parts of each strip 2201a, 2201b are peelably separable about beak 2210a, 2210b. The resulting empty base foil 2221a, 2221b coils up in respective base take-up chambers 2214a, 2214b. A base foil anchor 2215a, 2215b anchors the end of each respective base foil 2221a, 2221b in its chamber 2214a, 2214b. The used lid foil 2220a, 2220b feeds over its respective beak 2210a, 2210b and coils about common lid take-up spindle 2216 in lid take-up chamber 2218.

The lid take-up spindle 2216 is provided with a centrally-located torsion spring 2217. The function of the torsion spring 2217 is to ensure a roughly constant driving tension is providable to each strip 2201a, 2201b by the lid take-up spindle 2216 over the course of each entire strip length. In particular, the torsion spring 2217 acts to compensate for the variation in drive tension associated with the increase in the effective winding diameter of the lid take-up spindle 2216 as used lid foils 2220a, 2220b gradually becomes wrapped there around. Thus, uniform indexing of each strip 2201a, 2201b may be maintained over the entire strip length.

In use, the dispenser is primed by actuating lever 2226 located on the side of the dispenser to drivably actuate the lid-take up spindle 2216 to advance each blister strip 2201a, 2201b, thereby causing the leading pocket 2204a, 2204b thereof to be peeled open. The torsion spring acts to provide any necessary drive compensation, as described above. To access the contents of the opened pockets 2204a, 2204b, the patient then breathes in through the outlet 2224. This results in negative pressure being transmitted through manifold 2222 to the opened leading pocket 2204*a*, 2204*b* of each strip 2201*a*, 2201*b* at the opening station 2208. This in turn, results in the medicament powder contained within each of the opened pockets 2204*a*, 2204*b* being drawn out through the common manifold 2222 to the outlet 2224 and hence to the patient as an inhaled combination medicament dose. It be appreciated that, mixing of each separately delivered component of the combined medicament product happens as the powder is transported from each opened pocket 2204*a*, 2204*b* to the outlet 2224.

Figure 23:
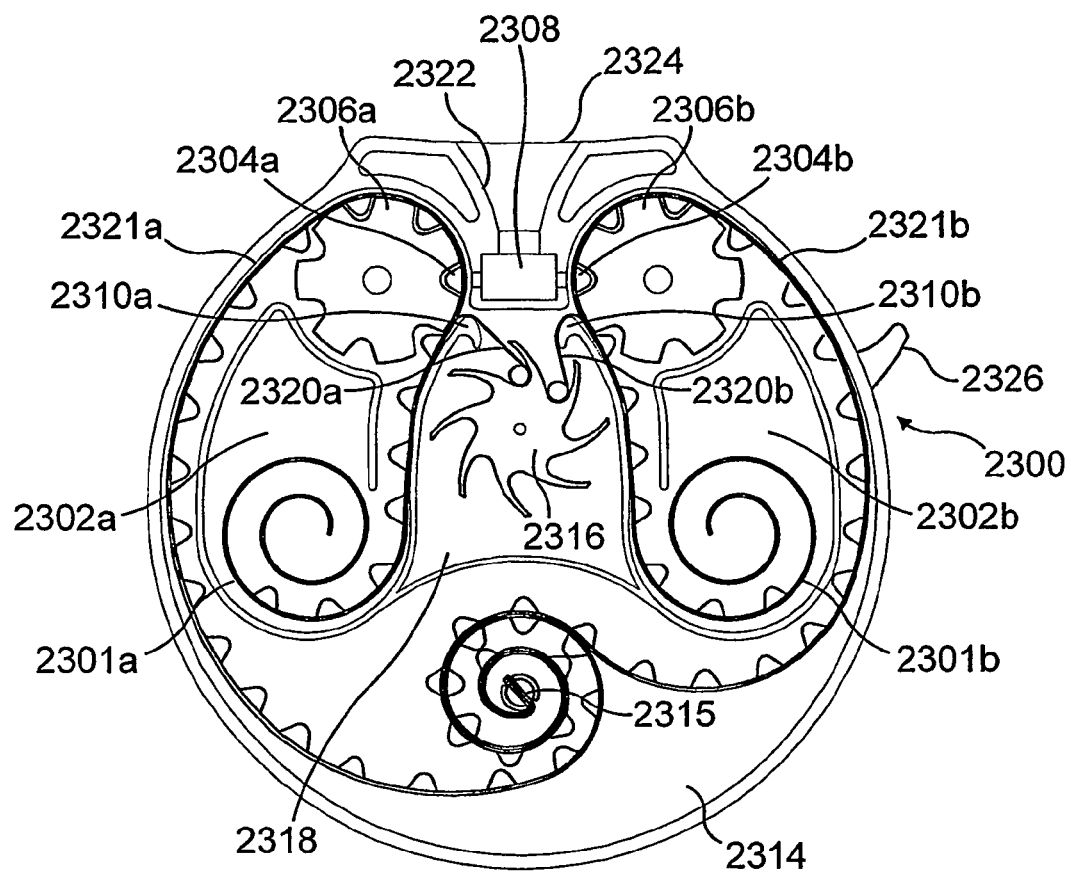

FIG. 23 illustrates a sectional view of base unit 2300 of a medicament dispenser according to the invention. In use, a protective cover (not shown) would be provided to the base unit 2300. First and second medicament-containing blister strips 2301*a*, 2301*b* are positioned within respective left and right chambers 2302*a*, 2302*b* of the base unit 2300. Each blister strip 2301*a*, 2301*b* engages in respective multi-pocket index wheel 2306*a*, 2306*b*, and successive pockets are thereby guided towards a central opening station 2308. The rotation of the index wheels 2306*a*, 2306*b* is optionally coupled together. At the opening station 2308, the lid foil 2320*a*, 2320*b* and base foil 2321*a*, 2321*b* parts of each strip 2301*a*, 2301*b* are peelably separable about beak 2310*a*, 2310*b*. The resulting empty base foil 2321*a*, 2321*b* coils up in common base take-up chamber 2314 about common base foil anchor 2315. The used lid foil 2320*a*, 2320*b* feeds over its respective beak 2310*a*, 2310*b* and coils about common 'collapsible wheel' form lid take-up spindle 2316 in the common lid take-up chamber 2318.

In use, the dispenser is primed by actuating lever 2326 located on the side of the dispenser to drivably actuate the lid-take up spindle 2316 to advance each blister strip 2301*a*, 2301*b*, thereby causing the leading pocket 2304*a*, 2304*b* thereof to be peeled open. To access the contents of the opened pockets 2304*a*, 2304*b*, the patient then breathes in through the outlet 2324. This results in negative pressure being transmitted through manifold 2322 to the opened leading pocket 2304*a*, 2304*b* of each strip 2301*a*, 2301*b* at the opening station 2308. This in turn, results in the medicament powder contained within each of the opened pockets 2304*a*, 2304*b* being drawn out through the common manifold 2322 to the outlet 2324 and hence to the patient as an inhaled combination medicament dose. Mixing of each separately delivered component of the combined medicament product happens as the powder is transported from each opened pocket 2304*a*, 2304*b* to the outlet 2324.

Figure 24:
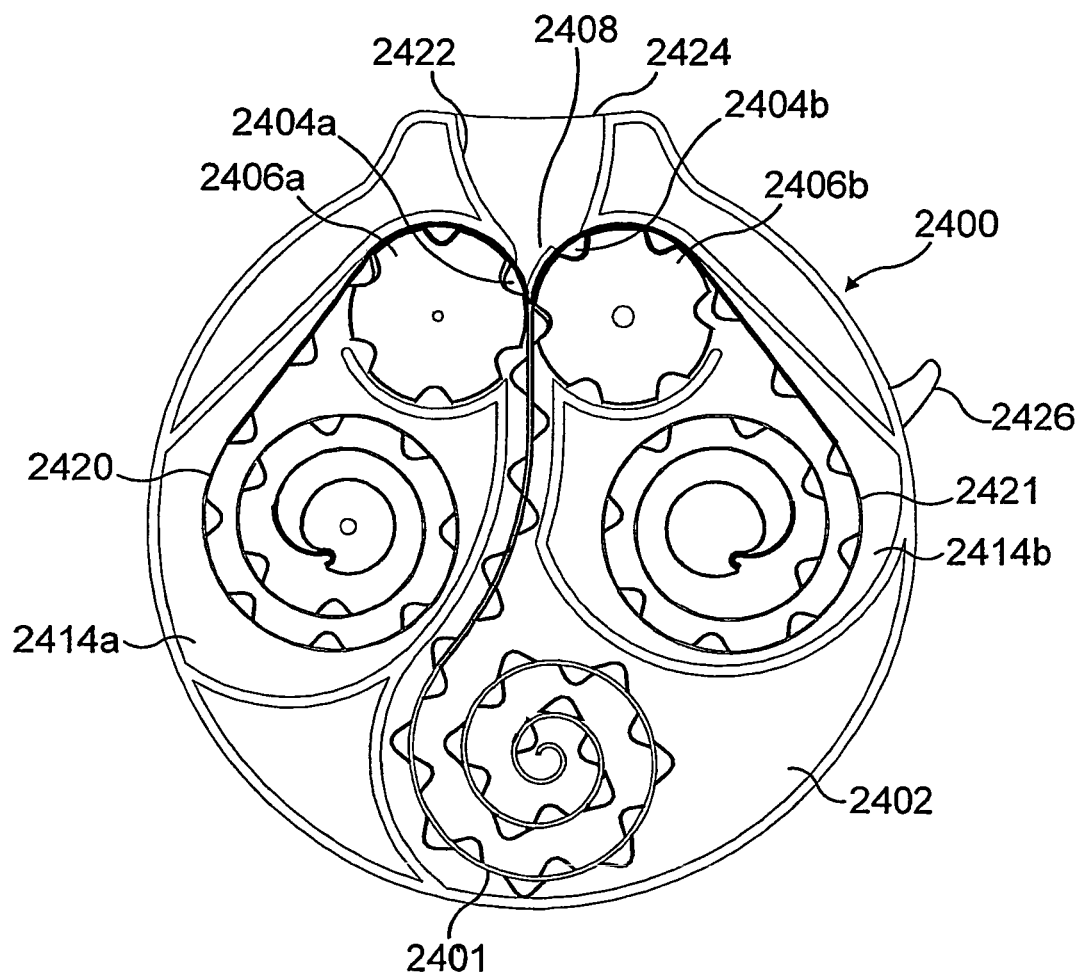

FIG. 24 illustrates a sectional view of base unit 2400 of a medicament dispenser according to the invention. In use, a protective cover (not shown) would be provided to the base unit 2400. The dispenser is provided with a single combination strip 2401 which is comprised of two foils 2420, 2421 applied to each other in a 'back-to-back' configuration and having pockets 2404*a*, 2404*b* arranged to alternate—one on the first side, then on the other side. It will be noted that both foils have pockets 2404*a*, 2404*b* for carrying medicament provided along their length and that when mating together one effectively acts as a 'lid foil' for the other. In use, the component foils 2420, 2421 are each loaded with different medicament types.

The dual medicament-containing blister strip 2401 is positioned within load chamber 2402 of the base unit 2400. Each foil component 2420, 2421 of the blister strip 2401 engages in respective multi-pocket index wheel 2406*a*, 2406*b*, and successive pockets are thereby guided towards a central opening station 2408. It will be noted that the index wheels 2406*a*, 2406*b* are arranged side-by-side and almost touching one another, In a subtle aspect, the index wheels 2406*a*, 2406*b* are also arranged to be slightly out of registration with each other to accommodate the (opening of the) alternating pockets 2404*a*, 2464*b* of the strip 2401. At the opening station 2408, the first 2420 and second 2421 foil component parts of the strip 2401 are peelably separable one from the other. The resulting empty foils 2420, 2421 coil up in respective take-up chambers 2414*a*, 2414*b*.

In use, the dispenser is primed by actuating lever 2426 located on the side of the dispenser to drivably actuate both index wheels 2406*a*, 2406*b* to advance each foil component 2420, 2421 of blister strip 2401 thereby causing the leading pocket 2404*a*, 2404*b* of each to be peeled open. To access the contents of the opened pockets 2404*a*, 2404*b*, the patient then breathes in through the outlet 2424. This results in negative pressure being transmitted through manifold 2422 to the opened leading pocket 2404*a*, 2404*b* of each foil 2420, 2421 at the opening station 2408. This in turn, results in the medicament powder contained within each of the opened pockets 2404*a*, 2404*b* being drawn out through the common manifold 2422 to the outlet 2424 and hence to the patient as an inhaled combination medicament dose. It be appreciated that, mixing of each separately delivered component of the combined medicament product happens as the powder is transported from each opened pocket 2404*a*, 2404*b* to the outlet 2424.

Figure 25A:
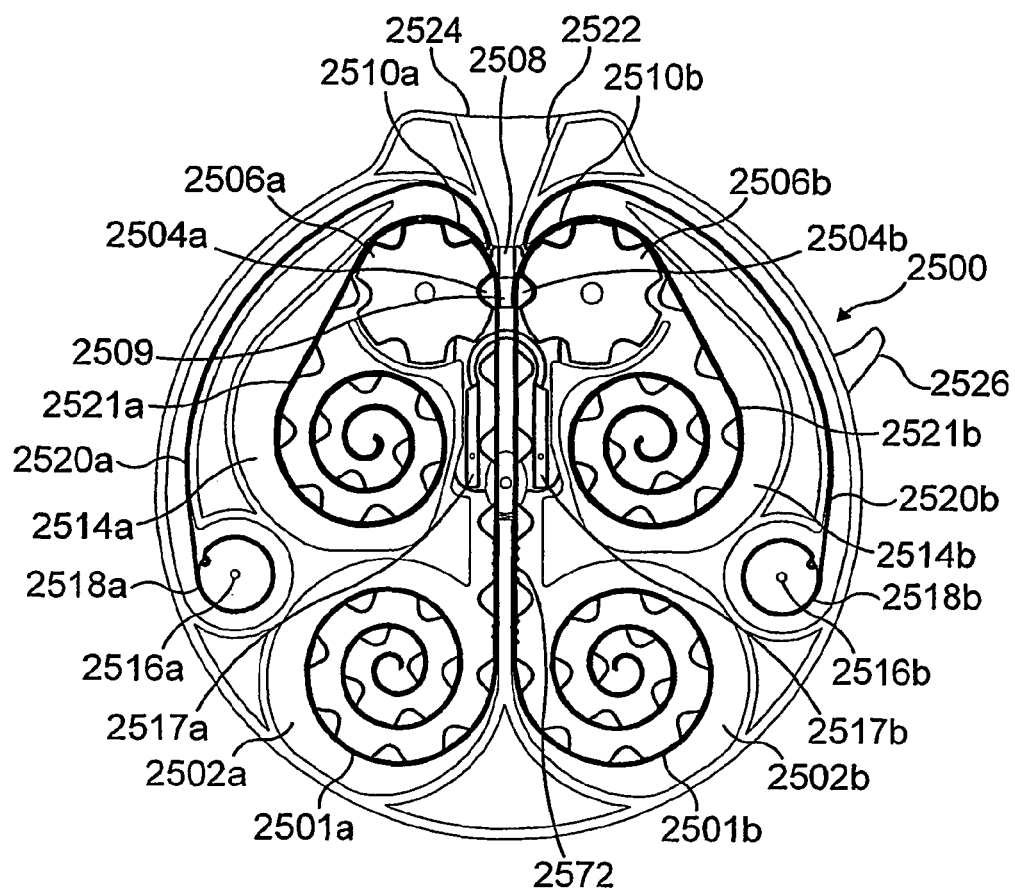

FIG. 25*a* illustrates a sectional view of base unit 2500 of a medicament dispenser according to the invention. In use, a protective cover (not shown) would be provided to the base unit 2500. The dispenser of FIG. 25*a* incorporates a 'variable position' opening station 2508 (shown in detail in FIG. 25*b*) to act as a compensating means to ensure uniform accessing of pockets 2504*a*, 2504*b* over the entire length of a strip form medicament carrier 2501*a*, 2501*b*. Such compensating means provides an alternative to the earlier described 'collapsible wheel' (e.g. lid take up spindle 916 of FIG. 9) or 'spring tension' (e.g. spring-loaded tensioner 2117*a*, 2117*b* of FIG. 21 or torsion hub 2217 of FIG. 22) approaches.

First and second medicament-containing blister strips 2501*a*, 2501*b* are positioned within respective left and right chambers 2502*a*, 2502*b* of the base unit 2500. Each blister strip 2501*a*, 2501*b* engages in respective multi-pocket index wheel 2506*a*, 2506*b*, and successive pockets are thereby guided towards 'variable position' opening station 2508.

Figure 25B:
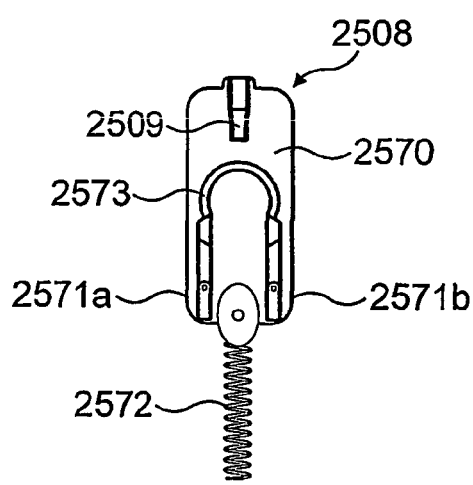

Turning to FIG. 25*b*, the opening station 2508 may be seen to comprise cruciform chamber 2509 which in use, locates adjacent opened leading pockets 2504*a*, 2504*b* of each strip 2501*a*, 2501*b*. The cruciform chamber 2509 is provided to bi-pronged 2571*a*, 2571*b* carrier bob 2570 which is spring 2572 mounted within the dispenser unit 2500 such as to be movable along its sprung axis. Arc element 2573 abuts the index wheels 2506*a*, 2506*b* to assist registration of the cruciform 2509 with the opened leading pockets 2504*a*, 2504*b*.

At opening station 2508 the lid foil 2520*a*, 2520*b* and base foil 2521*a*, 2521*b* parts of each strip 2501*a*, 2501*b* are peelably separable about beak 2510*a*, 2510*b*. The resulting empty base foil 2521*a*, 2521*b* coils up in respective base take-up chambers 2514*a*, 2514*b*. The used lid foil 2520*a*, 2520*b* feeds over its respective beak 2510*a*, 2510*b* and coils about its respective lid take-up spindle 2516*a*, 2516*b* in its lid take-up chamber 2518*a*, 2518*b*.

In use, the dispenser is primed by common actuating lever 2526 located on the side of the dispenser to drivably actuate each (non-collapsible, hub form) lid-take up spindle 2516*a*, 2516*b* to advance each blister strip 2501*a*, 2501*b*, thereby causing the leading pocket 2504*a*, 2504*b* thereof to be peeled open. On actuation, lid-foil 2520*a*, 2520*b* wraps around each spindle 2516*a*, 2516*b*. The effective winding diameter of each spindle 2516*a*, 2516*b*—defined by the diameter of the spindle 2516*a*, 2516*b* in combination with the used lid foil 2520*a*, 2520*b* wrapped there around—therefore increases with each actuation. As a consequence of this increase, each strip 2501*a*, 2501*b* will be advanced slightly further on each subsequent actuation and the effective location of the opened pockets 2504*a*, 2504*b* is consequently moved. To compensate for this movement the 'variable position' opening station 2508 also moves. In more detail, the carrier bob 2570 moves progressively along its sprung 2572 axis to ensure that position of the cruciform chamber 2509 always matches that of the opened pockets 2504*a*, 2504*b*.

To access the contents of the opened pockets 2504*a*, 2504*b* the patient breathes in through the outlet 2524. This results in negative pressure being transmitted through manifold 2522 to the cruciform chamber 2509 and opened leading pocket 2504*a*, 2504*b* of each strip 2501*a*, 2501*b*. This in turn, results in the medicament powder contained within each of the opened pockets 2504*a*, 2504*b* being drawn out through the common manifold 2522 to the outlet 2524 and hence to the patient as an inhaled combination medicament dose. It be appreciated that, mixing of each separately delivered component of the combined medicament product happens as the powder is transported from each opened pocket 2504*a*, 2504*b* to the outlet 2524.

It may be appreciated that any of the parts of the dispenser or cassette that contact the medicament suspension may be coated with materials such as fluoropolymer materials (e.g. PTFE or FEP) which reduce the tendency of medicament to adhere thereto. Any movable parts may also have coatings applied thereto which enhance their desired movement characteristics. Frictional coatings may therefore be applied to enhance frictional contact and lubricants (e.g. silicone oil) used to reduce frictional contact as necessary.

The medicament dispenser of the invention is suitable for dispensing medicament combinations, particularly for the treatment of respiratory disorders such as asthma and chronic obstructive pulmonary disease (COPD), bronchitis and chest infections.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy -androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl] amino]ethyl-2(3H) -benzothiazolone; adenosine 2a agonists, e.g. 2R,3R,4S,5R)-2-[6-Amino-2-(1S -hydroxymethyl-2-phenyl-ethylamino)-purin-9-yl]-5-(2-ethyl-2H-tetrazol-5-yl) -tetrahydro-furan-3,4-diol (e.g. as maleate); α$_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred components of the combinations comprise medicaments selected from albuterol, salmeterol, fluticasone propionate and beclomethasone dipropionate and salts or solvates thereof, e.g., the sulphate of albuterol and the xinafoate of salmeterol.

Preferred components of combinations of active ingredients contain a bronchodilator in combination with an anti-inflammatory. The bronchodilator is suitably a beta-agonist, particularly a long-acting beta-agonist (LABA). Suitable bronchodilators include salbutamol (e.g., as the free base or the sulphate salt), salmeterol (e.g., as the xinafoate salt) and formoterol (eg as the fumarate salt). The anti-inflammatory is suitably an anti-inflammatory steroid. Suitably anti-inflammatory compounds include a beclomethasone ester (e.g., the dipropionate), a fluticasone ester (e.g., the propionate) or budesonide or any salt or solvate thereof. One preferred combination of components comprises fluticasone propionate and salmeterol, or any salt or solvate thereof (particularly the xinafoate salt). A further combination of components of particular interest is budesonide and formoterol or any salt or solvate thereof (e.g. formoterol as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

It will be understood that the present disclosure is for the purpose of illustration only and the Invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. An inhalation device comprising:
   two elongate form medicament carriers, each carrier having multiple distinct medicament dose portions in powder form carried thereby, the medicament dose portions of one carrier containing a medicament active, or a mixture of medicament actives, which is different from that in the medicament dose portions of the other carrier,
   an actuating member for actuating the inhalation device,
   a dispensing mechanism which is adapted to operate, upon each actuation of the actuating member, to act upon each medicament carrier together to dispense a single distinct medicament dose portion carried by each medicament carrier, said mechanism comprising,
   a) at least one receiving station for receiving the medicament carriers;
   b) a release for releasing in combination a distinct medicament dose portion from each of the medicament carriers on receipt thereof by said at least one receiving station; and
   c) an indexer for each medicament carrier for individually indexing the distinct medicament dose portions thereof, the indexers being mutually coupled; and
   an outlet, positioned to be in communication with the combination of distinct medicament dose portions releasable by said release and which a user is able to inhale thereat for simultaneous inhalation of the distinct medicament dose portions releasable by said release.

2. The device according to claim 1, wherein a common receiving station receives each of the plural medicament carriers.

3. The device according to claim 1, comprising two distinct receiving stations, each receiving one of the medicament carriers.

4. The device according to claim 1, wherein said release comprises means to access medicament carried by said medicament carrier by a rupturing, puncturing, tearing or peeling action.

5. The device according to claim 1, wherein said medicament carriers are blister strips which are openable by a peeling action and wherein said release comprises at least one peeler for peeling apart said medicament carriers.

6. The device according to claim 1, wherein said outlet is a single common outlet, which communicates with the combination of distinct medicament dose portions on their release.

7. The device according to claim 6, wherein said common outlet is shaped to encourage mixing of said released medicament dose portions.

8. A method of dispensing a combination product, comprising:
   (a) providing the device according to claim 1, and;
   (b) dispensing a combination medicament product therefrom.

9. A method of treating one or more respiratory disorder(s) in a patient in need thereof comprising:
   (a) providing the device of claim 1;
   (b) dispensing medicament therefrom, and
   (c) delivering the dispensed medicament to the patient.

10. The method of treating one or more respiratory disorder(s) of claim 9, wherein the respiratory disorder comprises asthma.

11. The method of treating one or more respiratory disorder(s) of claim 9, wherein the respiratory disorder comprises COPD.

12. The device according to claim 1, wherein the carriers are blister strip form medicament carriers, each having multiple distinct pockets containing the medicament dose portions, wherein said pockets are spaced along the length of and defined between base and lid sheets which are peelably secured to each other, said dispensing mechanism comprising,
    a) an opening station for receiving a pocket of each of said medicament carriers;
    b) at least one peeler positioned to engage the base sheet and the lid sheet of a pocket of each carrier which has been received in said opening station for peeling apart the base sheet and lid sheet, to open the pocket of each carrier;
    wherein the outlet is positioned to be in communication with the opened pockets for a user to access the medicament dose portions from the opened pockets through the outlet; and
    the indexers are able to individually index the distinct pockets of each of the plural medicament carriers.

13. The device according to claim 12, wherein a common opening station receives each of the blister strips.

14. The device according to claim 12, comprising plural distinct opening stations each for receiving a single blister strip.

15. The device according to claim 12, wherein said opening station is movable within the dispenser.

16. The device according to claim 15, wherein said at least one opening station comprises a chamber that in use, moves to locate adjacent said opened pocket of each blister strip.

17. The device according to claim 16, wherein said chamber is provided to a carrier that is movably mountable along a sprung axis.

18. The device according to claim 12, wherein each blister strip is acted on by common peeler.

19. The device according to claim 12, wherein each blister strip is acted on by a distinct peeler.

20. The device according to claim 12, wherein said at least one peeler includes a lid driver for pulling apart said lid sheet and said base sheet of a pocket that has been received at the at least one opening station.

21. The device according to claim 20, wherein the lid driver comprises a wheel on which the lid sheet is wound up, said wheel being arranged to progressively collapse as the lid sheet becomes wound around it to provide an overall approximately constant effective winding diameter.

22. The device according to claim 20, additionally comprising control means to control the movement of said lid driver, in order to control the length of blister strip peeled thereby.

23. The device according to claim 22, wherein said control means comprises a clutch.

24. The device according to claim 20, additionally comprising compensating means to compensate for any variation in the pulling tension of the lid driver.

25. The device according to claim 24, wherein said compensating means has the form of a flexible member positioned between said at least one opening station and said lid driver.

26. The device according to claim 25, wherein said flexible member comprises a variable length spring.

27. The device according to claim 24, wherein the compensating means comprises a torsion spring mountable at the lid driver.

28. The device according to claim 12, additionally comprising a guide for guiding the lid sheet and base sheet along separate paths subsequent to their peeling apart.

29. The device according to claim 12, wherein each indexer comprises a rotatable index wheel having plural blister pocket-engaging recesses provided thereto.

30. The device according to claim 12, additionally comprising chambers for housing said plural medicament carriers prior to opening, and the lid sheet and base sheet components thereof subsequent to opening.

31. The device according to claim 1, wherein each medicament carrier has the form of a continuous loop.

32. The device according to claim 31, wherein the medicament carrier is in the form of a peelable strip comprising a base sheet and a lid sheet peelably secured thereto, and the base sheet is formed as a continuous loop.

33. The device according to claim 32, wherein the lid sheet is in the form of a continuous loop.

34. The device according to claim 32, wherein the lid sheet is in the form of a strip.

35. The device according to claim 1, wherein each medicament dose portion of each medicament carrier comprises a single active medicament component.

36. The device according to claim 35, wherein said single active medicament components are selected from the group consisting of anti-inflammatories, bronchodilators, and anticholinergics.

37. The device according to claim 36, wherein the anti-inflammatory is a fluticasone ester.

38. The device according to claim 1, wherein said multiple distinct dose portions are arranged in series progression on the carrier such that each dose portion is separately accessible.

39. The device according to claim 38, wherein each medicament carrier is in the form of a strip or tape.

40. The device according to claim 38, wherein each medicament carrier is in the form of a blister pack.

41. The device according to claim 40, wherein said blister pack form medicament carrier comprises a peelable blister strip.

42. The device according to claim 41, wherein said peelable blister strip comprises a base sheet in which blisters are formed to define pockets therein containing the distinct medicament dose portions and a lid sheet that is hermetically sealed to the base sheet except in the region of the blisters in such a manner that the lid sheet and the base sheet can be peeled apart.

43. The device according to claim 42, wherein said lid sheet comprises at least the following successive layers: (a) paper;
adhesively bonded to (b) polyester; adhesively bonded to (c) aluminium foil; that is coated with a heat seal lacquer for bonding to the base sheet.

44. The device according to claim 42, wherein the base sheet comprises at least the following successive layers: (a) oriented polyamide (OPA); adhesively bonded to (b) aluminium foil; adhesively bonded to (c) a third layer comprising a polymeric material.

45. The device according to claim 38, wherein each medicament carrier is sized and shaped to carry equivalent dose portions.

46. The device according to claim 38, wherein each medicament carrier is sized and shaped to carry non-equivalent dose portions.

47. The device according to claim 38, wherein the multiple distinct dose portions of each medicament carrier are uniformly spaced.

48. The device according to claim 38, wherein the multiple distinct dose portions of each medicament carrier are arranged such that the spacing between each dose portion progressively increases.

49. The device according to claim 38, wherein the spacing of the multiple distinct dose portions is equivalent for each medicament carrier.

50. The device according to claim 38, wherein the medicament carriers are arranged in the dispenser in 'side-by-side' configuration.

51. The device according to claim 38, wherein the medicament carriers are arranged in the dispenser in 'double-decker' configuration.

52. The device according to claim 38, wherein the medicament carriers are arranged in the dispenser in 'back-to-back' configuration.

53. The device according to claim 35, wherein said single active medicament components are selected from the group consisting of albuterol, salmeterol, fluticasone propionate, formoterol, budesonide and beclomethasone dipropionate and salts or solvates thereof.

54. The device according to claim 35, wherein each medicament dose portion of a first one of the two medicament carriers comprises a bronchodilator as the active medicament component and each medicament dose portion of the other medicament carrier comprises an anti-inflammatory as the active medicament component.

55. The device according to claim 54, wherein said bronchodilator is a beta-agonist and said anti-inflammatory is a steroid.

56. The device according to claim 1, wherein each medicament dose portion of at least one medicament carrier comprises plural active medicament components.

57. The device according to claim 56, wherein each medicament dose portion of a first one of the two medicament carriers comprises a single active medicament component and each medicament dose portion of the other medicament carrier comprises plural active medicament components.

58. The device according to claim 57, wherein said plural active medicaments comprise a bronchodilator and an anti-inflammatory.

59. The device according to claim 58, wherein said bronchodilator is a beta-agonist and said anti-inflammatory is a steroid.

60. A method of treating one or more respiratory disorder(s) in a patient in need thereof comprising:
(a) providing the device of claim 36;
(b) dispensing medicament therefrom, and
(c) delivering the dispensed medicament to the patient.

61. The method of treating one or more respiratory disorder(s) of claim 60, wherein the anti-inflammatory is a fluticasone ester.

62. The device according to claim 1, wherein the indexers are mutually coupled through a gear train.

63. An inhalation device comprising:
plural elongate form medicament carriers, each carrier having multiple distinct medicament dose portions in powder form carried thereby, the medicament dose portions of each carrier containing a medicament active, or a mixture of medicament actives, which is different from that in the medicament dose portions of the other carriers;

an actuating member for actuating the inhalation device;

a dispensing mechanism which is adapted to operate, upon each actuation of the actuating member, to act upon each medicament carrier together to release a single distinct medicament dose portion carried by each medicament carrier, said mechanism comprising an indexer for each medicament carrier for individually indexing the distinct medicament dose portions thereof, said indexers being mutually coupled; and an outlet, positioned to be in communication with the combination of distinct medicament dose portions when released by said dispensing mechanism and which a user is able to inhale thereat for simultaneous inhalation of the distinct medicament dose portions released by said dispensing mechanism.

64. The device according to claim 63, wherein the indexers are mutually coupled through a gear train.

65. The device according to claim 63, wherein said medicament carriers are blister strips which have blister pockets which contain the distinct medicament dose portions.

66. The device according to claim 53, wherein each indexer comprises a rotatable index wheel having plural blister pocket-engaging recesses provided thereto.

67. The device according to 64, wherein said medicament carriers are blister strips which have blister pockets which contain the distinct medicament dose portions and wherein each indexer comprises a rotatable index wheel having plural blister pocket- engaging recesses provided thereto.

68. The device according to claim 53, wherein the blister strips are openable by a peeling action and wherein said dispensing mechanism comprises at least one peeler for peeling apart said medicament carriers.

69. The device according to claim 67, wherein the blister strips are openable by a peeling action and wherein said dispensing mechanism comprises at least one peeler for peeling apart said medicament carriers.

70. The device according to claim 63, wherein each medicament dose portion of each medicament carrier comprises a single active medicament component.

71. The device according to claim 70, wherein each medicament dose portion of a first one of the two medicament carriers comprises a bronchodilator as the active medicament component and each medicament dose portion of the other medicament carrier comprises an anti-inflammatory as the active medicament component.

72. The device according to claim 71, wherein said bronchodilator is a beta-agonist and said anti-inflammatory is a steroid.

73. The device according to claim 70, wherein said single active medicament components are selected from the group consisting of antiinflammatories, bronchodilators, and anticholinergics.

74. The device according to claim 73, wherein the antiinflammatory is a fluticasone ester.

* * * * *

UNITED STATES PATENT AND TRADEMARK OFFICE
CERTIFICATE OF CORRECTION

| | | |
|---|---|---|
| PATENT NO. | : 8,511,304 B2 | Page 1 of 1 |
| APPLICATION NO. | : 10/502519 | |
| DATED | : August 20, 2013 | |
| INVENTOR(S) | : Anderson et al. | |

It is certified that error appears in the above-identified patent and that said Letters Patent is hereby corrected as shown below:

In the Claims:

Claim 63 (Column 43, Lines 1-3) should read as follows:

a mixture of medicament actives, which is different from
that in the medicament dose portions of the other carrier(s);

Signed and Sealed this
Twenty-second Day of October, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,511,304 B2 | Page 1 of 1 |
| APPLICATION NO. | : 10/502519 | |
| DATED | : August 20, 2013 | |
| INVENTOR(S) | : Anderson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1604 days.

Signed and Sealed this
Twelfth Day of May, 2015

Michelle K. Lee
*Director of the United States Patent and Trademark Office*